(12) United States Patent
Boersen

(10) Patent No.: US 9,981,971 B2
(45) Date of Patent: May 29, 2018

(54) SOLID FORMS OF 1-ETHYL-7-(2-METHYL-6-(1H-1,2,4-TRIAZOL-3-YL)PYRIDIN-3-YL)-3,4-DIHYDROPYRAZINO[2,3-B]PYRAZIN-2(1H)-ONE AS TOR KINASE INHIBITORS

(71) Applicant: Signal Pharmaceuticals, LLC, San Diego, CA (US)

(72) Inventor: Nathan Boersen, Summit, NJ (US)

(73) Assignee: Signal Pharmaceuticals, LLC, San Diego, CA (US)

(*) Notice: Subject to any disclaimer, the term of this patent is extended or adjusted under 35 U.S.C. 154(b) by 0 days. days.

(21) Appl. No.: 15/205,114

(22) Filed: Jul. 8, 2016

(65) Prior Publication Data

US 2016/0318940 A1 Nov. 3, 2016

Related U.S. Application Data

(63) Continuation of application No. 14/686,879, filed on Apr. 15, 2015, now Pat. No. 9,416,134.

(60) Provisional application No. 62/003,173, filed on May 27, 2014, provisional application No. 61/980,108, filed on Apr. 16, 2014.

(51) Int. Cl.
C07D 487/04 (2006.01)

(52) U.S. Cl.
CPC .................. C07D 487/04 (2013.01)

(58) Field of Classification Search
CPC .................................................. C07D 487/04
USPC ................ 544/350; 546/272.4; 548/266.4
See application file for complete search history.

(56) References Cited

U.S. PATENT DOCUMENTS

| | | | |
|---|---|---|---|
| 3,507,866 A | 4/1970 | Jones et al. |
| 3,567,725 A | 3/1971 | Grabowski et al. |
| 4,294,836 A | 10/1981 | Lesher et al. |
| 4,294,837 A | 10/1981 | Lesher et al. |
| 4,309,537 A | 1/1982 | Lesher et al. |
| 4,317,909 A | 3/1982 | Lesher et al. |
| 4,898,872 A | 2/1990 | Campbell et al. |
| 4,963,561 A | 10/1990 | Lesher et al. |
| 5,424,311 A | 6/1995 | Billhardt-Troughton |
| 5,869,659 A | 2/1999 | Stolle et al. |
| 6,031,105 A | 2/2000 | Wright |
| 6,093,728 A | 7/2000 | McMahon et al. |
| 6,372,740 B1 | 4/2002 | Murata et al. |
| 6,566,367 B2 | 5/2003 | Bakthayatchalam et al. |
| 6,791,006 B2 | 9/2004 | Nezu et al. |
| 6,800,436 B1 | 10/2004 | Jenne et al. |
| 6,825,184 B2 | 11/2004 | Cirillo et al. |
| 6,855,723 B2 | 2/2005 | McMahon et al. |
| 7,199,119 B2 | 4/2007 | Burkitt et al. |
| 7,247,621 B2 | 7/2007 | Hong et al. |
| 7,429,572 B2 | 9/2008 | Clark |
| 7,476,665 B2 | 1/2009 | Burgey |
| 7,608,622 B2 | 10/2009 | Liu et al. |
| 7,700,594 B2 | 4/2010 | Chen et al. |
| 7,767,687 B2 | 8/2010 | Oslob et al. |
| 7,902,187 B2 | 3/2011 | Neagu et al. |
| 7,919,490 B2 | 4/2011 | Neagu et al. |
| 7,968,556 B2 | 6/2011 | Mortensen et al. |
| 7,981,893 B2 | 7/2011 | Mortensen et al. |
| 8,034,948 B2 | 10/2011 | Coquerel et al. |
| 8,110,578 B2 | 2/2012 | Perin-Ninkovic et al. |
| 8,268,809 B2 | 9/2012 | Kalman |
| 8,372,976 B2 | 2/2013 | Mortensen et al. |
| 8,383,634 B2 | 2/2013 | Mortensen et al. |
| 8,492,381 B2 | 7/2013 | Perrin-Ninkovic et al. |
| 8,569,494 B2 | 10/2013 | Harris et al. |
| 8,642,660 B2 | 2/2014 | Goldfard |
| 2004/0063658 A1 | 4/2004 | Roberts et al. |
| 2006/0004014 A1 | 1/2006 | Hoffmann et al. |
| 2006/0142269 A1 | 6/2006 | Dykes |
| 2007/0036793 A1 | 2/2007 | Hardie et al. |
| 2008/0194019 A1 | 8/2008 | Cantley et al. |
| 2009/0181963 A1 | 7/2009 | Wyeth |
| 2009/0281075 A1 | 11/2009 | Roughton et al. |
| 2010/0144738 A1 | 6/2010 | Bommann et al. |
| 2011/0257167 A1 | 10/2011 | Chopra et al. |
| 2011/0318336 A1 | 12/2011 | Petricoin, III et al. |

(Continued)

FOREIGN PATENT DOCUMENTS

| | | |
|---|---|---|
| CA | 2 458 699 | 3/2003 |
| DE | 262 026 | 11/1988 |

(Continued)

OTHER PUBLICATIONS

Jordan, V. C. Nature Reviews: Drug Discovery, 2, 2003, 205.*

(Continued)

Primary Examiner — Douglas M Willis
(74) Attorney, Agent, or Firm — Jones Day

(57) ABSTRACT

Provided herein are formulations, processes, solid forms and methods of use relating to the Compound for formula 1:

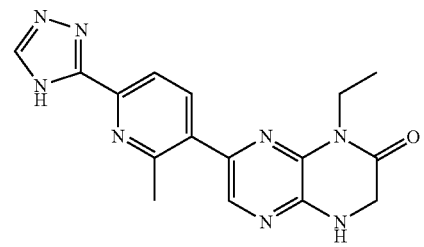

having the name 1-ethyl-7-(2-methyl-6-(1H-1,2,4-triazol-3-yl)pyridin-3-yl)-3,4-dihydropyrazino[2,3-b]pyrazin-2(1H)-one and tautomers thereof.

6 Claims, 32 Drawing Sheets

(56) References Cited

U.S. PATENT DOCUMENTS

| | | |
|---|---|---|
| 2012/0028972 A1 | 2/2012 | Wong et al. |
| 2012/0046457 A1 | 2/2012 | Kolla et al. |
| 2013/0102613 A1 | 4/2013 | Xu et al. |
| 2013/0142873 A1 | 6/2013 | Assaf et al. |
| 2013/0158023 A1 | 6/2013 | Ning et al. |
| 2013/0225518 A1 | 8/2013 | Xu et al. |
| 2013/0245026 A1 | 9/2013 | Xu et al. |
| 2013/0245027 A1 | 9/2013 | Xu et al. |
| 2013/0245028 A1 | 9/2013 | Xu et al. |
| 2013/0245029 A1 | 9/2013 | Xu et al. |
| 2013/0245254 A1 | 9/2013 | Harris et al. |
| 2014/0046057 A1 | 2/2014 | Cohen et al. |
| 2014/0113905 A1 | 4/2014 | Xu et al. |
| 2014/0314673 A1 | 10/2014 | Raymon et al. |
| 2014/0314674 A1 | 10/2014 | Raymon et al. |
| 2014/0314751 A1 | 10/2014 | Hege et al. |
| 2014/0314752 A1 | 10/2014 | Lopez-Girona et al. |
| 2014/0314753 A1 | 10/2014 | Hege et al. |
| 2014/0315848 A1 | 10/2014 | Raymon et al. |
| 2014/0315900 A1 | 10/2014 | Raymon et al. |
| 2014/0315907 A1 | 10/2014 | Raymon et al. |
| 2014/0315908 A1 | 10/2014 | Menon et al. |

FOREIGN PATENT DOCUMENTS

| | | |
|---|---|---|
| EP | 0 385 850 | 9/1990 |
| JP | 63275582 | 5/1987 |
| JP | 2001048882 | 2/2001 |
| JP | 2002100363 | 4/2002 |
| JP | 2002167387 | 6/2002 |
| WO | WO 03/032989 | 4/1903 |
| WO | WO 04/042002 | 5/1904 |
| WO | WO 99/16438 | 4/1999 |
| WO | WO 99/28320 | 6/1999 |
| WO | WO 99/28459 | 6/1999 |
| WO | WO 00/73306 | 12/2000 |
| WO | WO 02/048152 | 6/2002 |
| WO | WO 02/076954 | 10/2002 |
| WO | WO 03/032989 | 4/2003 |
| WO | WO 03/072557 | 9/2003 |
| WO | WO 03/093290 | 11/2003 |
| WO | WO 04/042002 | 5/2004 |
| WO | WO 04/048365 | 6/2004 |
| WO | WO 04/065378 | 8/2004 |
| WO | WO 04/076454 | 9/2004 |
| WO | WO 04/078754 | 9/2004 |
| WO | WO 04/085409 | 10/2004 |
| WO | WO 04/096797 | 11/2004 |
| WO | WO 05/003147 | 1/2005 |
| WO | WO 05/021519 | 3/2005 |
| WO | WO 05/120511 | 12/2005 |
| WO | WO 06/001266 | 1/2006 |
| WO | WO 06/018182 | 2/2006 |
| WO | WO 06/030031 | 3/2006 |
| WO | WO 06/036883 | 4/2006 |
| WO | WO 06/045828 | 5/2006 |
| WO | WO 06/046031 | 5/2006 |
| WO | WO 06/050076 | 5/2006 |
| WO | WO 06/065703 | 6/2006 |
| WO | WO 06/087530 | 8/2006 |
| WO | WO 06/090167 | 8/2006 |
| WO | WO 06/090169 | 8/2006 |
| WO | WO 06/091737 | 8/2006 |
| WO | WO 06/108103 | 10/2006 |
| WO | WO 07/044698 | 4/2007 |
| WO | WO 07/044729 | 4/2007 |
| WO | WO 07/044813 | 4/2007 |
| WO | WO 2007/047754 | 4/2007 |
| WO | WO 07/060404 | 5/2007 |
| WO | WO 07/066099 | 6/2007 |
| WO | WO 07/066102 | 6/2007 |
| WO | WO 07/080382 | 7/2007 |
| WO | WO 07/125321 | 11/2007 |
| WO | WO 07/129044 | 11/2007 |
| WO | WO 07/129052 | 11/2007 |
| WO | WO 07/129161 | 11/2007 |
| WO | WO 07/135398 | 11/2007 |
| WO | WO 08/016669 | 2/2008 |
| WO | WO 08/023161 | 2/2008 |
| WO | WO 08/032027 | 3/2008 |
| WO | WO 08/032028 | 3/2008 |
| WO | WO 08/032033 | 3/2008 |
| WO | WO 08/032036 | 3/2008 |
| WO | WO 08/032060 | 3/2008 |
| WO | WO 08/032064 | 3/2008 |
| WO | WO 08/032072 | 3/2008 |
| WO | WO 08/032077 | 3/2008 |
| WO | WO 08/032089 | 3/2008 |
| WO | WO 08/032091 | 3/2008 |
| WO | WO 08/051493 | 5/2008 |
| WO | WO 08/064093 | 5/2008 |
| WO | WO 08/115974 | 9/2008 |
| WO | WO 08/140947 | 11/2008 |
| WO | WO 09/007748 | 1/2009 |
| WO | WO 09/007750 | 1/2009 |
| WO | WO 09/007751 | 1/2009 |
| WO | WO 09/052145 | 4/2009 |
| WO | WO 09/102986 | 8/2009 |
| WO | WO 10/006072 | 1/2010 |
| WO | WO 10/062571 | 6/2010 |
| WO | WO 10/068483 | 6/2010 |
| WO | WO 11/031965 | 3/2011 |
| WO | WO 2011/053518 A1 | 5/2011 |
| WO | WO 11/079114 | 6/2011 |
| WO | WO 2011/097333 | 8/2011 |

OTHER PUBLICATIONS

Hackam, et al. JAMA, 296(14), 2006, 1731-1732.*
Barlin 1982, "Purine analogs as amplifiers of phleomycin. VII. Some 1H-inidazo[4,5-b]pyrazines and related compound," Australian Journal of Chemistry, vol. 35:2299-2306.
Beresnev et al., 2000, "Interaction of 5-methoxy-1,2,4-traizines with uras as a new route to 6-azapurines," Medeleev Commu., vol. 2:58-59.
Bergmann et al., 1963, "2-Phenylpurines, their chemical and enzumological reactivity," J. Chem Org. , pp. 3729-3735.
Booth et al., 1992, "Synthesis of 9-Hydroxyalkyl-substituted purines from the corresponding 4-(C-Cyanoformimidoyl)imidazole-5-amines," J, Chem Society, Perkin Transactions 1: Organic and Bio-Organic Chemstry, vol. 2119-26.
Booth et al., 1995, "Synthesis of [1α, 2β,3α-2,3-bis(benzyloxymethyl)cyclobutl]imidazol-5-amines: important precursors to cyclobut-A derivatives," J. Chem Society, Perkin Tranactions 1: Organic and Bio-Organic Chemistry, vol. 6, pp. 669-675.
Booth et al., 2001, "The Reactions of Diaminomaleonitrile with Isocyanates and Either Aldehydes or Ketones Revisited," J. Org Chem, vol. 66:8436-8441.
Booth, et al., 1994, "Synthesis of 4- and 5-Disubstituted 1-Benzylimidazoles, Important Precursors of Purine Analogs," J. of Heterocyclic of Chemistry, vol. 31(2):345-50.
Caira et al., 1998, "Crystalline Polymorphism of Organic Compounds," *Topics in Current Chemistry*, Jan. 1, 1998, pp. 163-208, vol. 198, Springer, Berlin, DE.
Carretero et al. 2010, "Integrative Genomic and Proteomic Analyses Indentity Targets for Lkb1-Deficient Metastatic Lung Tumors," Cancer Cell, vol. 17(6): 547-559.
Chupakhin et al., 2001, "A simple one pot synthesis of condensed 1,2,4-triazines by using the tandem $A_N$—$S_N$ipso and $S_N^H$—$S_N$ipso reactions," J. of Heterocyclic Chemistry, vol. 38(4):901-907.
Cohen, 2005, *Protein Kinase Inhibitors for the Treatment of Disease: The Promise and the Problems*, Handbook of Experimental Pharmacology, Springer Berlin Heidelberg, 167:1-7.
Cohen, P. 2001, "The role of protein phosphorylation in human health and disease," Eur. J. Biochem,vol. 268:5001-5010.
Cohen, P. 2002, "Protein kinases—the major drug targets of the twenty-first century?" Nature Reviews/Drug Discovery, vol. 1:309-315.
Coish, et al., 2006, "Small molecule inhibitors of IKK kinase activity," Expert Opin. Ther. Patents, vol. 16(1):1-12.

(56) References Cited

OTHER PUBLICATIONS

Crofts et al., 1997 "Metabolism of 2-amino-1-methyl-6-phenylimidazo [4,5-b]pyridine (PhIP) by human cytochrome P4501B1," Carcinogenesis, vol. 18(9):1793-1798.
Dang et al., 1999, "Efficient synthesis of purines and purine nucelosides via an inverse electron demand diels—alder reaction," J. Am Chem Soc., vol. 121(24):5833-5834.
Database Caplus Online Chemical Abstracts Service, Columbus, Ohio, Database Accession No. 1951:49974 (XP-002472261) (1951).
Database Caplus Online Chemical Abstracts Service, Columbus, Ohio, Database Accession No. 1978:433195 (XP-002472262) (1978).
Database Caplus Online Chemical Abstracts Service, Columbus, Ohio, Database Accession No. 1966:26849 (XP-002472263) (1965).
Dornow et al., 1957, "Synthese von2-Oxy-imidazolo-(5',4':2,3)-pyridinen)," Arch Pharm. vol. 290, pp. 20-31 (w/English language abstract).
Dzierba et al., 2004, "Synthesis, structure-activity relationships, and in vivo properties of 3,4-dihydro-1H-pyrido[2,3-b]pyrazin-2-ones as corticotropin-releasing factor-1 receptor antagonists," J of Medicinal Chemistry, vol. 47, pp. 5783-5790.
Fabbro et al., 2002, "Protein kinases as targets for anticancer agents: from inhibitors to useful drugs," Pharmacol Ther., 93(2-3):79-98.
Farhadi et al., 2006, "The role of protein kinase C isoforms in modulating injury and repair of the intestinal barrier," J. Pharm Exp. Ther., vol. 316(1):1-7.
Frandsen et al., 1992, "Reaction of the N2-acetoxy derivative of 2-amino-1-methyl-6-phenylimidazo[4,5,b] pyridine . . . ," Carcinogenesis, vol. 13(4):629-635.
Furniss et al., 1989, "Vogel's Textbook of Practical Organic Chemistry Fifth Edition," 1989, p. 132-136, Longman.
Gao et al. , 2010, "LKB1 inhibits lung cancer progression through lysyl oxidase and extracellular matrix remodeling," Proceedings of the National Academy of Sciences, vol. 107(44): 18892-18897.
Gao et al.: 2011, "LKB1 in lung cancerigenesis: a serine/threonine kinase as tumor suppressor," Protein & Cell, Gaodeng Jiaoyu Chubanshe, China, vol. 2(2): 99-107.
Georgakis and Younes, 2006, "From rapi nui to rapamycin: targeting PI3K/Akt/mTOR for cancer therapy," Expert Rev. Anticancer Ther., vol. 6(1):131-140.
Gini et al., 2013, "The mTOR Kinase Inhibitors, CC214-1 and CC214-2, Preferentially Block the Growth of EGFRvIII-Activated Glioblastomas," Clin Cancer Res 2013;19:5722-5732.
Grimmiger et al., 2010, "Targeting non-malignant disorders with tyrosine kinase inhibitors," Nat. Rev. Drug Disc., 9(12):956-970.
Hamad, 2001, "A new synthesis of 4-cyano-1,3-dihydro-2-oxo-2H-imidazole-5-($N^1$-tosyl)carboxamide: Reactive precursor for thiopurine analogues," J of Heterocyclic Chemistry, vol. 38(4):939-944.
Hernan et al., "De novo germline mutation in the serine-threonine kinase STK11/LKB1 gene associated with Peutz-Jeghers syndrome," Clin Genet., 66(1):58-62.
Huang et al., 2010, "Genetic and epigenetic silencing of SCARA5 may contribute to human hepatocellular carcinoma by activating FAK signaling," Journal of Clinical Investigation, American Society for Clinical investigation, vol. 120(1): 223-241.
Inge et al., 2009, "Expression of LKB1 tumor suppressor in non-small cell lung cancer determines sensitivity to 2-deoxyglucose," Journal of Thoracic and Cardiovascular Surgery, vol. 137(3): 580-586.
Irie et al., 2005, "Toward the development of new medicinal leads with selectivity for protein kinase C isozymes," The Chemical Record, vol. 5:185-195.
Itoh et al., 2004, "A novel practical synthesis of C-2-arylpurines," Advanced Synthesis & Catalysis, vol. 346:1859-1867.
Ji et al., 2007, "LKB1 modulates lung cancer differentiation and metastasis," Nature, 448(7155):807-810.
Jones et al., 1973, "6-Substituted-5-chloro-1,3-dihydro-2H-imidazo(4,5-b)pyrazin-2-ones with hypotensive activity," J. Med. Chem., vol. 16(5):537-542.
Kazaoka et al., 2003, "Synthesis of 6-substituted 9-benzyl-8-hydroxypurines with potential interferon-indcuing activity," Chemical & Pharmaceutical Bulletin, vol. 51(5):608-611.
Killday et al., 2001, "Microxine, a new cdc2 kinase inhibitor from the Australian marine sponge Microxina species," J. of Natural Products, vol. 64(4):525-526.
Mahoney et al., 2009, "LKB1/KRAS mutant lung cancers constitute a genetic subset of NSCLC with increased sensitivity to MAPK and mTOR signalling inhibition," Br J Cancer, 100(2):370-375.
Minehan et al., 2000, "Molecular recognition of DNA by Hoechst Benzimidazoles: Exploring beyond theopyrrole-imidazole-hydroxypyrrole polyamide-pairing code," Helvitica Chima Acta, vol. 83(9):2197-2213.
Nagashima et al., 2004, "Solution-Phase parallel synthesis of an N-Alkylated dihydropteridinone library from fluorous amino acids," J of Comb. Chemistry, vol. 6(6):942-949.
Park et al., 2000, "A novel mechanism of TRAF signaling revealed by structural and functional analyses of the TRADD-TRAF2 interaction," Cell, vol. 101:777-787.
Patani et al., 1998, "Bioisosterim: A rational approach in dmg design," Chemical Reviews, vol. 96:3147-3176.
PCT Annex Communication Relating to the Results of the Partial International Search issued in connection with PCT/US2012/049281,filed Aug. 2, 2012.
PCT International Search Report issued in connection with PCT/US2012/049281, filed Aug. 2, 2012.
PCT Written Opinion of the International Searching Authority issued in connection with PCT/US2012/049281, filed Aug. 2, 2012.
Registry File Document for RN 863501-03-5, 863502-39-0 and others (Sep. 20, 2005).
Seela et al., 2004, "Product Class 17: Purines," Science of Synthesis, vol. 16, pp. 945-1108.
Shaw et al., 2004, "The LKB1 tumor suppressor negativiely regulates mTOR signaling," Cancer Cell, vol. 6(1):91-99.
Shaw et al. 2009, "LKB1 and AMP—activated protein kinase control of mTOR signalling and growth," Acta. Physiol (Oxf.) 196(1):65-80.
Shoji et al. 2012, "Genotype-dependent efficacy of a dual PI3K/mTOR inhibitor, NVP-BEZ235, and an mTOR inhibitor, RAD001, in endometrial carcinomas." *PloS one* 7.5, 2012, e37431.
Singh et al., 1994, "Novel cAMP PDE III Inhibitors: Imidazo[4,5-b]pyridin-2(3H)-ones and Thiazolo [4,5-b]pyridin-2(3h)-ones and Their Analogs," J. Med. Chem, vol. 37(2):248-54.
Sridhar et al., 2000, "Protein kinases as therapeutic targets," Pharm. Res., 17(11):1345-1353.
Wallace 2008, "Palladium-catalyzed synthesis of quinoxaline derivatives," Tetrahedron, vol. 64:9675-9684.
Wei et al., 2009, "Chemopreventive efficacy of rapamycin on Peutz-Jeghers syndrome in a mouse model," Cancer Lett., 277(2):149-154.
Westover et al., 1981, "Synthesis and antiviral activity of certain 9-β-D-Riofuranoaylpurine-6-carboxamides," J.Med. Chem., vol. 24(8):941-46.
Wingo et al., 2009, "Somatic LKB1 mutations promote cervical cancer progression," PloS One, 4(4):1-8.
Yoneda et al., 1976, "A transformationof 7-azapteridines into 6-azapurines (Imidazo [4,5-e]-as-triazines)," Heterocycles, vol. 4(9):1503-1508.
Yoneda et al., 1978, "Synthesis of imadazo[4,5-e]-as-triazine (6-Azapurine) Deriviatives," Chem & Pharm Bulletin, vol. 26(10):3154-3160.
Yuan et al., 2009, "Targeting tumorigenesis: development and use of mTOR inhibitors in cancer therapy," Journal of Hematology & Oncology, Biomed Central Ltd., London UK, vol. 2(1): 45.
Zaki et al., 2007, "The synthesis of imidazol[4,5-d]pyridines from a substituted imidazole and acyl or sulfonyl acetonitrile," Tetrahedron, vol. 63(18):3745-3753.

(56) References Cited

OTHER PUBLICATIONS

Zhong et al., 2006, "LKB1 mutation in large cell carcinoma of the lung," Cancer Lung, vol. 53(3):285-294.

* cited by examiner

FIG. 8
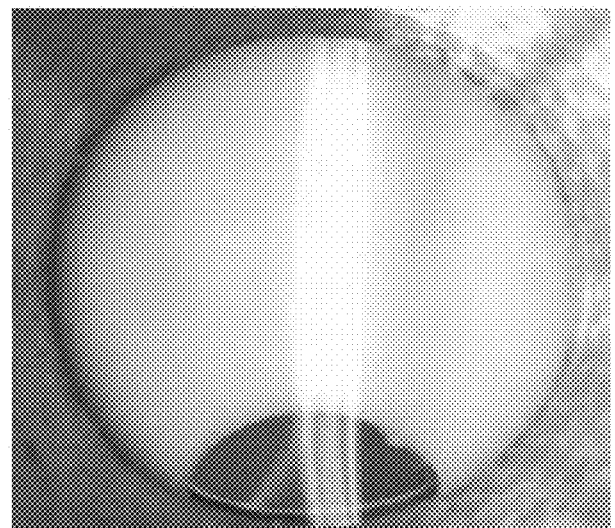
A
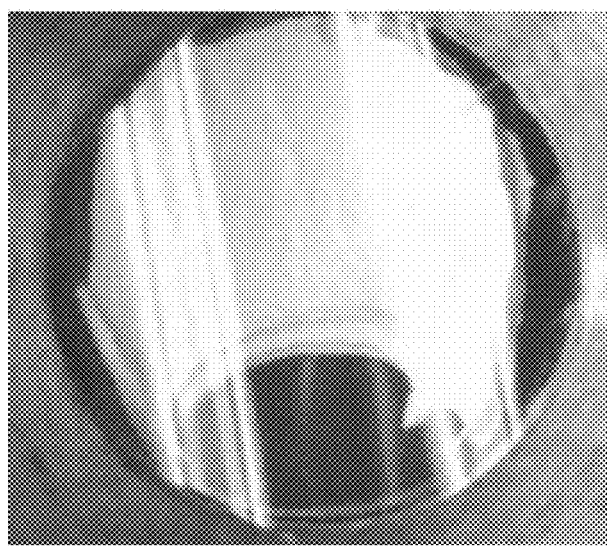
B

FIG. 11

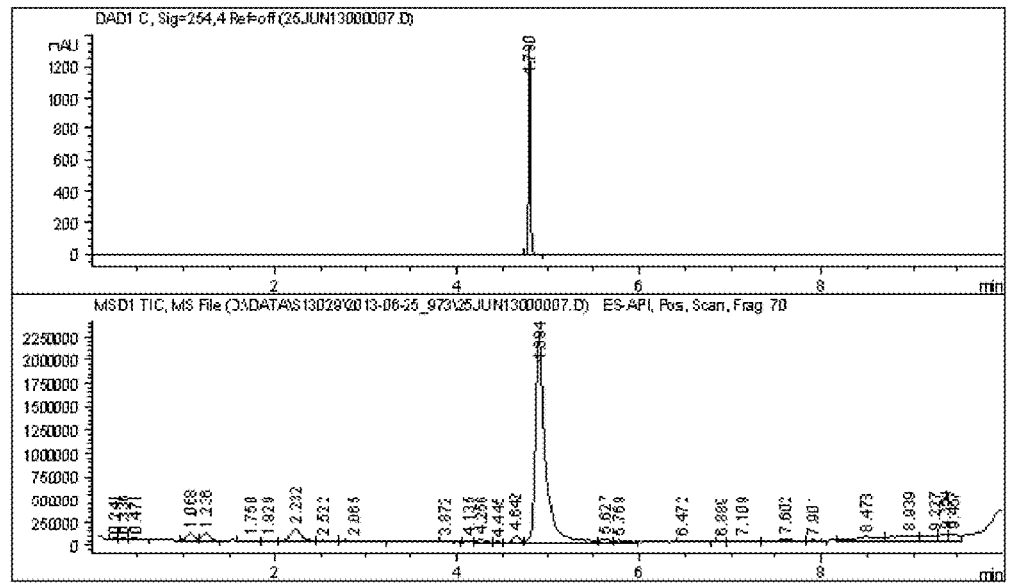

```
Method Info    : Method for Project S13029, based on Fstgr03 with optimal wavelengt at
                 254nm
```

```
============================================================================
                              Area Percent Report
============================================================================

Sorted By        :    Signal
Multiplier       :    1.0000
Dilution         :    1.0000
Use Multiplier & Dilution Factor with ISTDs Signal 1: DAD1 C, Sig=254,4 Ref=off Peak RetTime Type  Width     Area      Height     Area
 #   [min]         [min]    [mAU*s]    [mAU]       %
----|-------|----|--------|-----------|----------|--------|
 1   4.790  VB   0.0231   1955.58984 1336.78723  100.0000

Totals :                  1955.58984 1336.78723
```

FIG. 13
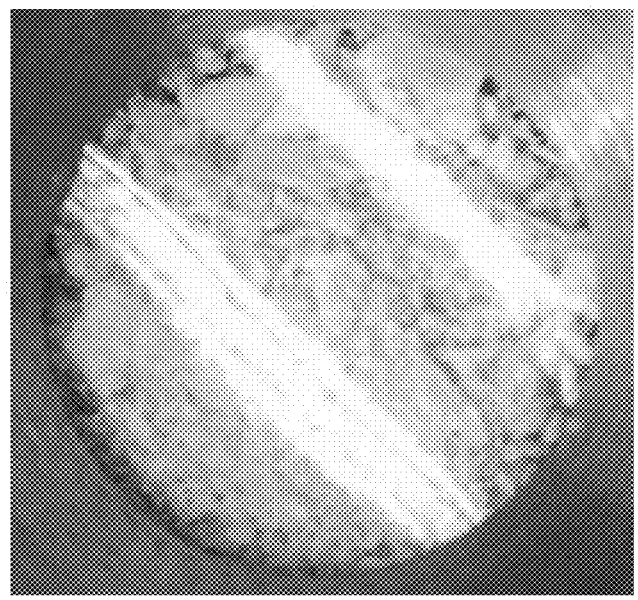
A
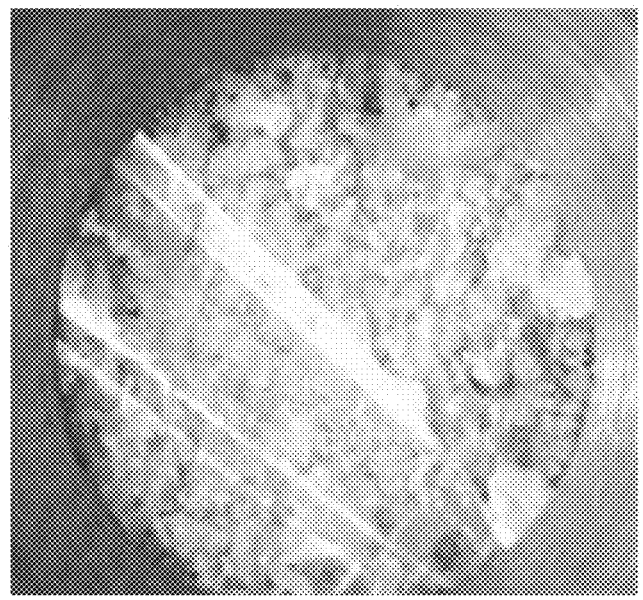
B

FIG. 18
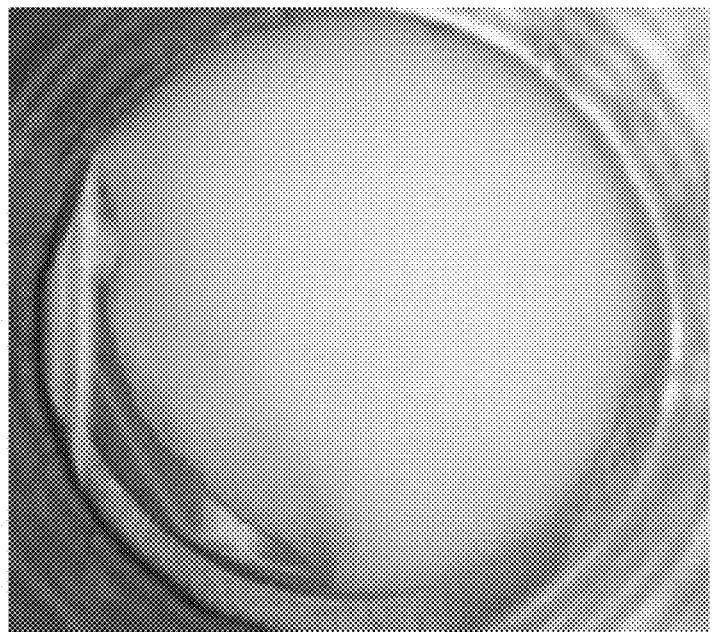
A
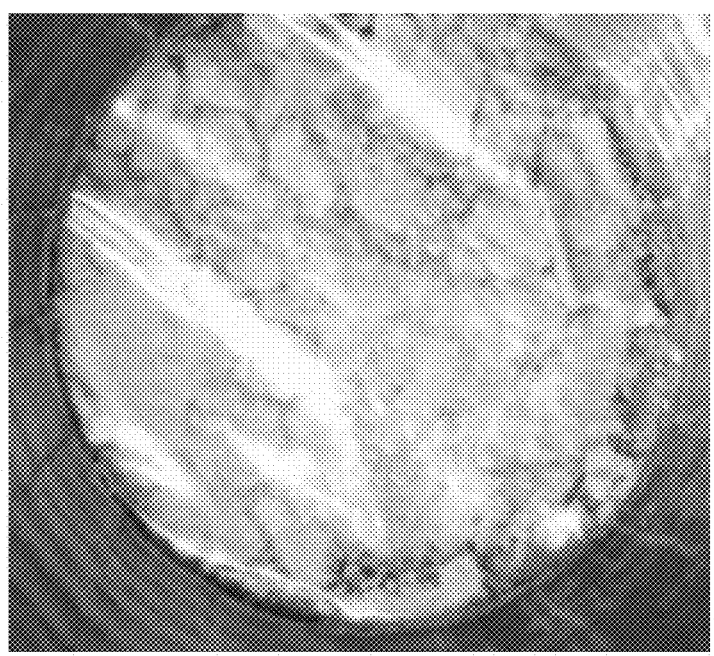
B

FIG. 23
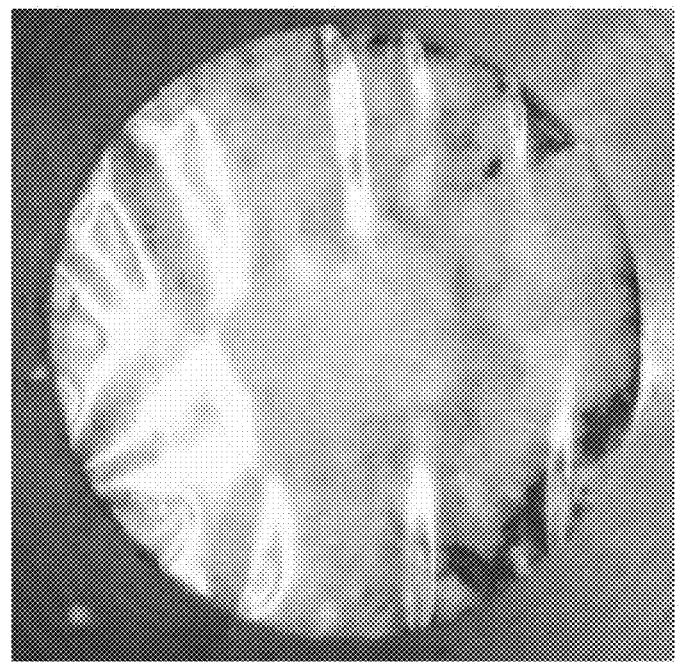
A
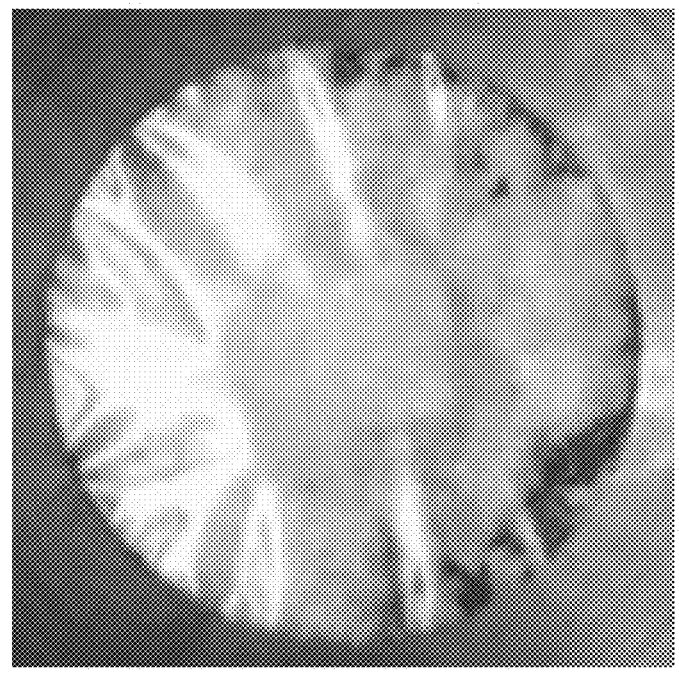
B

Raman - amorphous material at 150C

SOLID FORMS OF 1-ETHYL-7-(2-METHYL-6-(1H-1,2,4-TRIAZOL-3-YL)PYRIDIN-3-YL)-3,4-DIHYDROPYRAZINO[2,3-B]PYRAZIN-2(1H)-ONE AS TOR KINASE INHIBITORS

This application is a continuation of U.S. application Ser. No. 14/686,879, filed Apr. 15, 2015, currently allowed, which claims the benefit of U.S. Provisional Application No. 61/980,108, filed Apr. 16, 2014 and the benefit of U.S. Provisional Application No. 62/003,173, filed May 27, 2014, the entire contents of each of which are incorporated herein by reference.

1. FIELD

Provided herein are solid forms of 1-ethyl-7-(2-methyl-6-(1H-1,2,4-triazol-3-yl)pyridin-3-yl)-3,4-dihydropyrazino[2,3-b]pyrazin-2(1H)-one, compositions thereof, and methods of their use for the treatment of a disease, disorder, or condition.

2. BACKGROUND

The identification and selection of a solid form of a pharmaceutical compound is complex, given that a change in solid form may affect a variety of physical and chemical properties, which may provide benefits or drawbacks in processing, formulation, stability and bioavailability, among other important pharmaceutical characteristics. Potential pharmaceutical solids include crystalline solids and amorphous solids. Amorphous solids are characterized by a lack of long-range structural order, whereas crystalline solids are characterized by structural periodicity. The desired class of pharmaceutical solid depends upon the specific application; amorphous solids are sometimes selected on the basis of, e.g., an enhanced dissolution profile, while crystalline solids may be desirable for properties such as, e.g., physical or chemical stability (see, e.g., S. R. Vippagunta et al., *Adv. Drug. Deliv. Rev.*, (2001) 48:3-26; L. Yu, *Adv. Drug. Deliv. Rev.*, (2001) 48:27-42).

Whether crystalline or amorphous, potential solid forms of a pharmaceutical compound include single-component and multiple-component solids. Single-component solids consist essentially of the pharmaceutical compound in the absence of other compounds. Variety among single-component crystalline materials may potentially arise from the phenomenon of polymorphism, wherein multiple three-dimensional arrangements exist for a particular pharmaceutical compound (see, e.g., S. R. Byrn et al., Solid State Chemistry of Drugs, (1999) SSCI, West Lafayette). The importance of discovering polymorphs was underscored by the case of Ritonavir, an HIV protease inhibitor that was formulated as soft gelatin capsules. About two years after the product was launched, the unanticipated precipitation of a new, less soluble polymorph in the formulation necessitated the withdrawal of the product from the market until a more consistent formulation could be developed (see S. R. Chemburkar et al., *Org. Process Res. Dev.*, (2000) 4:413-417).

Additional diversity among the potential solid forms of a pharmaceutical compound may arise from the possibility of multiple-component solids. Crystalline solids comprising two or more ionic species are termed salts (see, e.g., Handbook of Pharmaceutical Salts: Properties, Selection and Use, P. H. Stahl and C. G. Wermuth, Eds., (2002), Wiley, Weinheim). Additional types of multiple-component solids that may potentially offer other property improvements for a pharmaceutical compound or salt thereof include, e.g., hydrates, solvates, co-crystals and clathrates, among others (see, e.g., S. R. Byrn et al., Solid State Chemistry of Drugs, (1999) SSCI, West Lafayette). Moreover, multiple-component crystal forms may potentially be susceptible to polymorphism, wherein a given multiple-component composition may exist in more than one three-dimensional crystalline arrangement. The discovery of solid forms is of great importance in the development of a safe, effective, stable and marketable pharmaceutical compound.

Notably, it is not possible to predict a priori if crystalline forms of a compound even exist, let alone how to successfully prepare them (see, e.g., Braga and Grepioni, 2005, "Making crystals from crystals: a green route to crystal engineering and polymorphism," *Chem. Commun.* 3635-3645 (with respect to crystal engineering, if instructions are not very precise and/or if other external factors affect the process, the result can be unpredictable); Jones et al., 2006, Pharmaceutical Cocrystals: An Emerging Approach to Physical Property Enhancement," *MRS Bulletin* 31:875-879 (At present it is not generally possible to computationally predict the number of observable polymorphs of even the simplest molecules); Price, 2004, "The computational prediction of pharmaceutical crystal structures and polymorphism," *Advanced Drug Delivery Reviews* 56:301-319 ("Price"); and Bernstein, 2004, "Crystal Structure Prediction and Polymorphism," *ACA Transactions* 39:14-23 (a great deal still needs to be learned and done before one can state with any degree of confidence the ability to predict a crystal structure, much less polymorphic forms)).

The compound chemically named 1-ethyl-7-(2-methyl-6-(1H-1,2,4-triazol-3-yl)pyridin-3-yl)-3,4-dihydropyrazino[2,3-b]pyrazin-2(1H)-one and tautomers thereof (collectively referred to herein as "Compound 1") was disclosed in U.S. patent application Ser. No. 12/605,791, filed Oct. 26, 2009, and International Pub. No. WO 2010/062571, the entireties of each of which are incorporated by reference herein. We have discovered multiple solid forms of 1-ethyl-7-(2-methyl-6-(1H-1,2,4-triazol-3-yl)pyridin-3-yl)-3,4-dihydropyrazino[2,3-b]pyrazin-2(1H)-one.

Citation or identification of any reference in Section 2 of this application is not to be construed as an admission that the reference is prior art to the present application.

3. SUMMARY

Provided herein are solid forms of the Compound for formula 1:

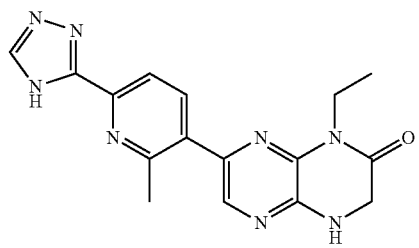

having the name 1-ethyl-7-(2-methyl-6-(1H-1,2,4-triazol-3-yl)pyridin-3-yl)-3,4-dihydropyrazino[2,3-b]pyrazin-2(1H)-one and tautomers thereof.

Also provided herein are formulations of solid forms of the Compound of formula 1 and tautomers thereof.

One crystal form provided herein has characteristic X-ray powder diffraction peaks at a two-theta angle of approximately 6.18, 21.74 and 26.7 degrees. The X-ray powder diffraction pattern can further comprise characteristic X-ray powder diffraction peaks at a two-theta angle of approximately 12.34, 22.5 and 23.42 degrees. The crystal form can have a thermogravimetric analysis thermogram comprising a total mass loss of approximately 15.5% of the total mass of the crystal form when heated from about 25° C. to about 300° C. The crystal form can have a single differential thermal analysis thermogram comprising an endotherm between about 90° C. and about 185° C. with a maximum at approximately 140° C. when heated from about 25° C. to about 300° C. The single differential thermal analysis thermogram can further comprise an endotherm between about 240° C. and about 285° C. with a maximum at approximately 264° C. The crystal form can be 1,2-ethanediol solvated. The crystal form can comprise 1 molar equivalent of 1,2-ethanediol. The crystal form can be substantially pure.

A further crystal form provided herein has characteristic X-ray powder diffraction peaks at a two-theta angle of approximately 3.5, 9.26 and 18.62 degrees. The X-ray powder diffraction pattern can further comprise characteristic X-ray powder diffraction peaks at a two-theta angle of approximately 7.06, 12.66 and 15.3 degrees. The crystal form can have a thermogravimetric analysis thermogram comprising a total mass loss of approximately 12.8% of the total mass of the crystal form when heated from about 25° C. to about 300° C. The crystal form can have a single differential thermal analysis thermogram comprising an endotherm between about 110° C. and about 175° C. with a maximum at approximately 160° C. when heated from about 25° C. to about 300° C. The single differential thermal analysis thermogram can further comprise an endotherm between about 225° C. and about 275° C. with a maximum at approximately 254° C. The crystal form can be 2,2,2-trifluoroethanol solvated. The crystal form can comprise 0.5 molar equivalents of 2,2,2-trifluoroethanol. The crystal form can be substantially pure.

Another crystal form provided herein has characteristic X-ray powder diffraction peaks at a two-theta angle of approximately 10.66, 21.94 and 26.26 degrees. The X-ray powder diffraction pattern can further comprise characteristic X-ray powder diffraction peaks at a two-theta angle of approximately 10.14, 18.1 and 22.66 degrees. The crystal form can have a thermogravimetric analysis thermogram comprising a total mass loss of approximately 16.4% of the total mass of the crystal form when heated from about 25° C. to about 300° C. The crystal form can have a single differential thermal analysis thermogram comprising an endotherm between about 100° C. and about 175° C. with a maximum at approximately 140° C. when heated from about 25° C. to about 300° C. The single differential thermal analysis thermogram can further comprise an endotherm between about 235° C. and about 275° C. with a maximum at approximately 258° C. The crystal form can be dimethylsulfoxide solvated. The crystal form can comprise 0.8 molar equivalents of dimethylsulfoxide. The crystal form can be substantially pure.

Still another crystal form provided herein has characteristic X-ray powder diffraction peaks at a two-theta angle of approximately 9.26, 11.7 and 26.18 degrees. The X-ray powder diffraction pattern can further comprise characteristic X-ray powder diffraction peaks at a two-theta angle of approximately 7.46, 24.26 and 24.94 degrees. The crystal form can have a thermogravimetric analysis thermogram comprising a total mass loss of approximately 9.4% of the total mass of the crystal form when heated from about 25° C. to about 300° C. The crystal form can have a single differential thermal analysis thermogram comprising an endotherm between about 50° C. and about 140° C. with a maximum at approximately 80° C. when heated from about 25° C. to about 300° C. The single differential thermal analysis thermogram can further comprise an exotherm between about 160° C. and about 200° C. with a maximum at approximately 181° C. The single differential thermal analysis thermogram can further comprise an endotherm between about 225° C. and about 275° C. with a maximum at approximately 251° C. The crystal form can be hydrated. The crystal form can comprise 2 molar equivalents of water. The crystal form can substantially pure.

Further provided herein is an amorphous form comprising Compound 1, or a tautomer thereof. The amorphous form has a differential scanning calorimetry thermogram comprising an endotherm between about 160° C. and about 200° C. with a maximum at approximately 188.1° C. The amorphous form has a glass transition temperature at about 120° C. The amorphous form can be substantially pure.

The solid forms provided herein can be used as a medicament. In certain embodiments, solid forms of Compound 1 and tautomers thereof are useful for treating or preventing cancer and conditions treatable or preventable by inhibition of a kinase pathway, for example, the mTOR/PI3K/Akt pathway. The solid forms provided herein can be used in methods for treating or preventing cancer, an inflammatory condition, an immunological condition, a neurodegenerative disease, diabetes, obesity, a neurological disorder, an age-related disease, a cardiovascular condition, or a conditions treatable or preventable by inhibition of a kinase pathway. The methods comprise administering an effective amount of a crystal form provided herein to a subject in need thereof. The kinase pathway is the TOR kinase pathway.

The solid forms of Compound 1 and tautomers thereof can be used in methods for achieving a Response Evaluation Criteria in Solid Tumors (RECIST 1.1) of complete response, partial response or stable disease in a subject. The methods comprise administering an effective amount of a crystal form provided herein to a subject having a solid tumor.

The solid forms of Compound 1 and tautomers thereof can be used in methods for improving International Workshop Criteria (IWC) for NHL, International Uniform Response Criteria for Multiple Myeloma (IURC), Eastern Cooperative Oncology Group Performance Status (ECOG) or Response Assessment for Neuro-Oncology (RANO) Working Group for GBM. The methods comprise administering an effective amount of a crystal form provided herein to a subject in need thereof.

The present embodiments can be understood more fully by reference to the detailed description and examples, which are intended to exemplify non-limiting embodiments.

4. BRIEF DESCRIPTION OF THE DRAWINGS

FIG. 8 depicts a digital image of Form 2 of Compound 1 (A) and a digital image of Form 2 of Compound 1 after exposure to accelerated aging conditions (B).

FIG. 11 depicts high performance liquid chromatography coupled with mass spectrometry of Form 2 of Compound 1.

FIG. 13 depicts a digital image of Form 3 of Compound 1 (A) and a digital image of Form 3 of Compound 1 after exposure to accelerated aging conditions (B).

FIG. 18 depicts a digital image of Form 4 of Compound 1 as wet solid (A) and a digital image of Form 4 of Compound 1 as dry solid (B).

FIG. 23 depicts a digital image of Form 5 of Compound 1 (A) and a digital image of Form 5 of Compound 1 after exposure to accelerated aging conditions (B).

5. DETAILED DESCRIPTION

5.1 Definitions

Figure 1:
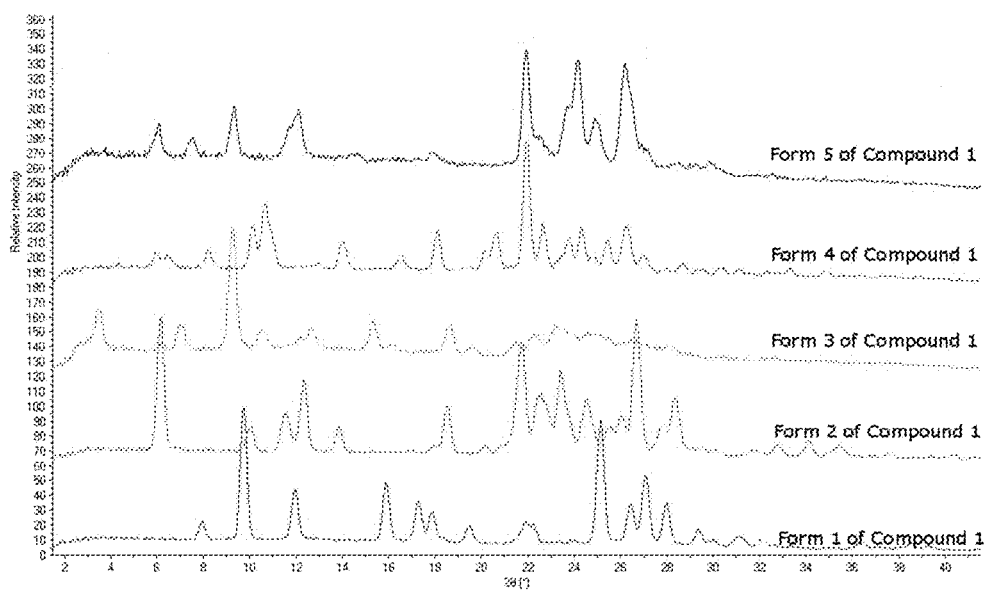
FIG. 1 depicts an X-ray powder diffractogram stack plot of Forms 1, 2, 3, 4 and 5 of Compound 1.

As used herein, the term "pharmaceutically acceptable salt(s)" refers to a salt prepared from a pharmaceutically acceptable non-toxic acid or base including an inorganic acid and base and an organic acid and base. Suitable pharmaceutically acceptable base addition salts include, but are not limited to metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine. Suitable non-toxic acids include, but are not limited to, inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, phosphoric, sulfuric, and methanesulfonic acids. Examples of specific salts thus include hydrochloride and mesylate salts. Others are well-known in the art, see for example, *Remington's Pharmaceutical Sciences*, 18$^{th}$ eds., Mack Publishing, Easton Pa. (1990) or *Remington: The Science and Practice of Pharmacy*, 19$^{th}$ eds., Mack Publishing, Easton Pa. (1995).

Pharmaceutically acceptable salts of Compound 1 can be formed by conventional and known techniques, such as by reacting Compound 1 with a suitable acid as disclosed above. Such salts are typically formed in high yields at moderate temperatures, and often are prepared by merely isolating the compound from a suitable acidic wash in the final step of the synthesis. The salt-forming acid may dissolved in an appropriate organic solvent, or aqueous organic solvent, such as an alkanol, ketone or ester. On the other hand, if Compound 1 is desired in the free base form, it may be isolated from a basic final wash step, according to known techniques. For example, a typical technique for preparing hydrochloride salt is to dissolve the free base of Compound 1 in a suitable solvent, and dry the solution thoroughly, as over molecular sieves, before bubbling hydrogen chloride gas through it.

As used herein and unless otherwise indicated, the term "stereoisomer" or "stereomerically pure" means one stereoisomer of a compound that is substantially free of other stereoisomers of that compound. For example, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, greater than about 90% by weight of one stereoisomer of the compound and less than about 10% by weight of the other stereoisomers of the compound, greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound. Compounds can have chiral centers and can occur as racemates, individual enantiomers or diastereomers, and mixtures thereof. All such isomeric forms are included within the embodiments disclosed herein, including mixtures thereof. The use of stereomerically pure forms of such compounds, as well as the use of mixtures of those forms are encompassed by the embodiments disclosed herein. For example, mixtures comprising equal or unequal amounts of the enantiomers of a particular compound may be used in methods and compositions disclosed herein. These isomers may be asymmetrically synthesized or resolved using standard techniques such as chiral columns or chiral resolving agents. See, e.g., Jacques, J., et al., *Enantiomers, Racemates and Resolutions* (Wiley-Interscience, New York, 1981); Wilen, S. H., et al., *Tetrahedron* 33:2725 (1977); Eliel, E. L., *Stereochemistry of Carbon Compounds* (McGraw-Hill, N Y, 1962); and Wilen, S. H., *Tables of Resolving Agents and Optical Resolutions* p. 268 (E. L. Eliel, Ed., Univ. of Notre Dame Press, Notre Dame, Ind., 1972).

It should also be noted the compounds can include E and Z isomers, or a mixture thereof, and cis and trans isomers or a mixture thereof. In certain embodiments, compounds are isolated as either the cis or trans isomer. In other embodiments, compounds are a mixture of the cis and trans isomers.

"Tautomers" refers to isomeric forms of a compound that are in equilibrium with each other. The concentrations of the isomeric forms will depend on the environment the compound is found in and may be different depending upon, for example, whether the compound is a solid or is in an organic or aqueous solution. For example, in aqueous solution, pyrazoles may exhibit the following isomeric forms, which are referred to as tautomers of each other:

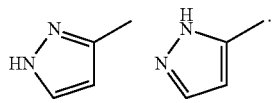

As readily understood by one skilled in the art, a wide variety of functional groups and other structures may exhibit tautomerism and all tautomers of Compound 1 are within the scope of the present invention.

It should also be noted that Compound 1 can contain unnatural proportions of atomic isotopes at one or more of the atoms. For example, Compound 1 may be radiolabeled with radioactive isotopes, such as for example tritium ($^3$H), or carbon-14 ($^{14}$C), or may be isotopically enriched, such as with deuterium ($^2$H), carbon-13 ($^{13}$C), or nitrogen-15 ($^{15}$N). As used herein, an "isotopologue" is an isotopically enriched compound. The term "isotopically enriched" refers to an atom having an isotopic composition other than the natural isotopic composition of that atom. "Isotopically enriched" may also refer to a compound containing at least one atom having an isotopic composition other than the natural isotopic composition of that atom. The term "isotopic composition" refers to the amount of each isotope present for a given atom. Radiolabeled and isotopically enriched compounds are useful as therapeutic agents, e.g., cancer and inflammation therapeutic agents, research reagents, e.g., binding assay reagents, and diagnostic agents, e.g., in vivo imaging agents. All isotopic variations of Compound 1, whether radioactive or not, are intended to be encompassed within the scope of the embodiments provided herein. In some embodiments, there are provided isotopologues of Compound 1, for example, the isotopologues are deuterium, carbon-13, or nitrogen-15 enriched Compound 1.

The term "solid form" refers to a physical form which is not predominantly in a liquid or a gaseous state. As used herein and unless otherwise specified, the term "solid form," when used herein to refer to Compound 1, refers to a physical form comprising Compound 1 which is not predominantly in a liquid or a gaseous state. A solid form may be a crystalline form, an amorphous form, or a mixture thereof. In certain embodiments, a solid form may be a liquid crystal. In certain embodiments, the term "solid forms comprising Compound 1" includes crystal forms comprising Compound 1, amorphous forms comprising Compound 1, and mixtures thereof. In certain embodiments, the solid form of Compound 1 is Form 1, Form 2, Form 3, Form 4, Form 5, amorphous or a mixture thereof.

As used herein and unless otherwise specified, the term "crystalline" when used to describe a compound, substance, modification, material, component or product, unless otherwise specified, means that the compound, substance, modification, material, component or product is substantially crystalline as determined by X-ray diffraction. See, e.g., Remington: The Science and Practice of Pharmacy, 21st edition, Lippincott, Williams and Wilkins, Baltimore, Md. (2005).; The United States Pharmacopeia, 23$^{rd}$ ed., 1843-1844 (1995).

The term "crystal form" or "crystalline form" refers to a solid form that is crystalline. In certain embodiments, crystal forms include salts. In certain embodiments, a crystal form of a substance may be substantially free of amorphous forms and/or other crystal forms. In certain embodiments, a crystal form of a substance may contain less than about 1%, less than about 2%, less than about 3%, less than about 4%, less than about 5%, less than about 6%, less than about 7%, less than about 8%, less than about 9%, less than about 10%, less than about 15%, less than about 20%, less than about 25%, less than about 30%, less than about 35%, less than about 40%, less than about 45%, or less than about 50% by weight of one or more amorphous forms and/or other crystal forms. In certain embodiments, a crystal form of a substance may be physically and/or chemically pure. In certain embodiments, a crystal form of a substance may be about 99%, about 98%, about 97%, about 96%, about 95%, about 94%, about 93%, about 92%, about 91%, or about 90% physically and/or chemically pure.

The term "amorphous" or "amorphous form" means that the substance, component, or product in question is not substantially crystalline as determined by X-ray diffraction. In particular, the term "amorphous form" describes a disordered solid form, i.e., a solid form lacking long range crystalline order. In certain embodiments, an amorphous form of a substance may be substantially free of other amorphous forms and/or crystal forms. In certain embodiments, an amorphous form of a substance may contain less than about 1%, less than about 2%, less than about 3%, less than about 4%, less than about 5%, less than about 10%, less than about 15%, less than about 20%, less than about 25%, less than about 30%, less than about 35%, less than about 40%, less than about 45%, or less than about 50% by weight of one or more other amorphous forms and/or crystal forms on a weight basis. In certain embodiments, an amorphous form of a substance may be physically and/or chemically pure. In certain embodiments, an amorphous form of a substance be about 99%, about 98%, about 97%, about 96%, about 95%, about 94%, about 93%, about 92%, about 91%, or about 90% physically and/or chemically pure.

"Treating" as used herein, means an alleviation, in whole or in part, of the disease or disorder, or symptoms associated with the disease or disorder, or slowing, or halting of further progression or worsening of the disease or disorder, or symptoms associated with the disease or disorder.

"Preventing" as used herein, means prevention of the onset, recurrence, or spread of the disease or disorder, or symptoms associated with the disorder or disease, in a patient at risk for developing the disease or disorder.

The term "effective amount" in connection with a solid form of Compound 1 means, in one embodiment, an amount capable of alleviating, in whole or in part, symptoms associated with a disorder or disease, or slowing or halting further progression or worsening of those symptoms, or, in another embodiment, an amount capable of preventing or providing prophylaxis for the disease or disorder in a subject at risk for developing the disease or disorder as disclosed herein, such as cancer. In one embodiment an effective amount of Compound 1 is an amount that inhibits a kinase in a cell, such as, for example, in vitro or in vivo. In one embodiment the kinase is mTOR, DNA-PK, PI3K or a combination thereof. In some embodiments, the effective amount of Compound 1 inhibits the kinase in a cell by 10%, 20%, 30%, 40%, 50%, 60%, 70%, 80%, 90% or 99%, compared to the activity of the kinase in an untreated cell. The effective amount of Compound 1, for example in a pharmaceutical composition, may be at a level that will exercise the desired effect; for example, about 0.005 mg/kg of a subject's body weight to about 100 mg/kg of a patient's body weight in unit dosage for both oral and parenteral administration. As will be apparent to those skilled in the art, it is to be expected that the effective amount of Compound 1 disclosed herein may vary depending on the indication being treated, e.g., the effective amount of Compound 1 would likely be different for treating patients suffering from, or at risk for, inflammatory conditions relative to the effective amount of Compound 1 for treating patients suffering from, or at risk of, a different disorder, e.g., cancer or a metabolic disorder.

The term "patient" includes an animal, including, but not limited to, an animal such as a cow, monkey, horse, sheep, pig, chicken, turkey, quail, cat, dog, mouse, rat, rabbit or guinea pig, in one embodiment a mammal, in another embodiment a human.

The term "cancer" refers to any of various malignant neoplasms characterized by the proliferation of cells that can invade surrounding tissue and metastasize to new body sites. Both benign and malignant tumors are classified according to the type of tissue in which they are found. For example, fibromas are neoplasms of fibrous connective tissue, and melanomas are abnormal growths of pigment (melanin) cells. Malignant tumors originating from epithelial tissue, e.g., in skin, bronchi, and stomach, are termed carcinomas. Malignancies of epithelial glandular tissue such as are found in the breast, prostate, and colon, are known as adenocarcinomas. Malignant growths of connective tissue, e.g., muscle, cartilage, lymph tissue, and bone, are called sarcomas. Lymphomas and leukemias are malignancies arising among white blood cells. Through the process of metastasis, tumor cell migration to other areas of the body establishes neoplasms in areas away from the site of initial appearance. Bone tissues are one of the most favored sites of metastases of malignant tumors, occurring in about 30% of all cancer cases. Among malignant tumors, cancers of the lung, breast, prostate or the like are particularly known to be likely to metastasize to bone.

In the context of neoplasm, cancer, tumor growth or tumor cell growth, inhibition may be assessed by delayed appearance of primary or secondary tumors, slowed development of primary or secondary tumors, decreased occurrence of primary or secondary tumors, slowed or decreased severity of secondary effects of disease, arrested tumor growth and regression of tumors, among others. In the extreme, complete inhibition, is referred to herein as prevention or chemoprevention. In this context, the term "prevention" includes either preventing the onset of clinically evident neoplasia altogether or preventing the onset of a preclinically evident stage of neoplasia in individuals at risk. Also intended to be encompassed by this definition is the prevention of transformation into malignant cells or to arrest or reverse the progression of premalignant cells to malignant cells. This includes prophylactic treatment of those at risk of developing the neoplasia.

In certain embodiments, the treatment of lymphoma may be assessed by the International Workshop Criteria (IWC) for non-Hodgkin lymphoma (NHL) (see Cheson B D, Pfistner B, Juweid, M E, et. al. Revised Response Criteria for Malignant Lymphoma. J. Clin. Oncol: 2007: (25) 579-586), using the response and endpoint definitions shown below:

| Response | Definition | Nodal Masses | Spleen, liver | Bone Marrow |
|---|---|---|---|---|
| CR | Disappearance of all evidence of disease | (a) FDG-avid or PET positive prior to therapy; mass of any size permitted if PET negative (b) Variably FDG-avid or PET negative; regression to normal size on CT | Not palpable, nodules disappeared | Infiltrate cleared on repeat biopsy; if indeterminate by morphology, immunohistochemistry should be negative |
| PR | Regression of measurable disease and no new sites | ≥50% decrease in SPD of up to 6 largest dominant masses; no increase in size of other nodes (a) FDG-avid or PET positive prior to therapy; one or more PET positive at previously involved site (b) Variably FDG-avid or PET negative; regression on CT | ≥50% decrease in SPD of nodules (for single nodule in greatest transverse diameter); no increase in size of liver or spleen | Irrelevant if positive prior to therapy; cell type should be specified |
| SD | Failure to attain CR/PR or PD | (a) FDG-avid or PET positive prior to therapy; PET positive at prior sites of disease and no new sites on CT or PET (b) Variably FDG-avid or PET negative; no change in size of previous lesions on CT | | |
| PD or relapsed disease | Any new lesion or increase by ≥50% of previously involved sites from nadir | Appearance of a new lesion(s) ≥1.5 cm in any axis, ≥50% increase in SPD of more than one node, or ≥50% increase in longest diameter of a previously identifed node ≥1 cm in short axis Lesions PET positive if FDG-avid lymphoma or PET positive prior to therapy | ≥50% increase from nadir in the SPD of any previous lesions | New or recurrent involvement |

Abbreviations: CR, complete remission; FDG, [18F]fluorodeoxyglucose; PET, positron emission tomography; CT, computed tomography; PR, partial remission; SPD, sum of the product of the diameters; SD, stable disease; PD, progressive disease.

| End point | Patients | Definition | Measured from |
|---|---|---|---|
| Primary | | | |
| Overall survival | All | Death as a result of any cause | Entry onto study |
| Progression-free survival | All | Disease progression or death as a result of any cause | Entry onto study |
| Secondary | | | |
| Event-free survival | All | Failure of treatment or death as result of any cause | Entry onto study |
| Time to progression | All | Time to progression or death as a result of lymphoma | Entry onto study |
| Disease-free survival | In CR | Time to relapse or death as a result of lymphoma or acute toxicity of treatment | Documentation of response |
| Response duration | In CR or PR | Time to relapse or progression | Documentation of response |
| Lymphoma-specific survival | All | Time to death as a result of lymphoma | Entry onto study |
| Time to next treatment | All | Time to new treatment | End of primary treatment |

Abbreviations: CR: complete remission; PR: partial remission.

In one embodiment, the end point for lymphoma is evidence of clinical benefit. Clinical benefit may reflect improvement in quality of life, or reduction in patient symptoms, transfusion requirements, frequent infections, or other parameters. Time to reappearance or progression of lymphoma-related symptoms can also be used in this end point.

In certain embodiments, the treatment of CLL may be assessed by the International Workshop Guidelines for CLL (see Hallek M, Cheson B D, Catovsky D, et al. Guidelines for the diagnosis and treatment of chronic lymphocytic leukemia: a report from the International Workshop on Chronic Lymphocytic Leukemia updating the National Cancer Institute-Working Group 1996 guidelines. Blood, 2008; (111) 12: 5446-5456) using the response and endpoint definitions shown therein and in particular:

| Parameter | CR | PR | PD |
|---|---|---|---|
| Group A | | | |
| Lymphadenopathy[†] | None >1.5 cm | Decrease ≥50% | Increase ≥50% |
| Hepatomegaly | None | Decrease ≥50% | Increase ≥50% |
| Splenomegaly | None | Decrease ≥50% | Increase ≥50% |
| Blood lymphocytes | <4000/μL | Decrease ≥50% from baseline | Increase ≥50% over baseline |
| Marrow[‡] | Normocellular, <30% lymphocytes, no B-lymphoid nodules. Hypocellular marrow defines CRi (5.1.6). | 50% reduction in marrow infiltrate, or B-lymphoid nodules | |
| Group B | | | |
| Platelet count | >100 000/μL | >100 000/μL or increase ≥50% over baseline | Decrease of ≥50% from baseline secondary to CLL |
| Hemoglobin | >11.0 g/dL | >11 g/dL or increase ≥50% over baseline | Decrease of >2 g/dL from baseline secondary to CLL |
| Neutrophils[‡] | >1500/μL | >1500/μL or ≥50% improvement over baseline | |

Group A criteria define the tumor load; Group B criteria define the function of the hematopoietic system (or marrow). CR (complete remission): all of the criteria have to be met, and patients have to lack disease-related constitutional symptoms; PR (partial remission): at least two of the criteria of group A plus one of the criteria of group B have to be met; SD is absence of progressive disease (PD) and failure to achieve at least a PR; PD: at least one of the above criteria of group A or group B has to be met. Sum of the products of multiple lymph nodes (as evaluated by CT scans in clinical trials, or by physical examination in general practice). These parameters are irrelevant for some response categories.

In certain embodiments, the treatment of multiple myeloma may be assessed by the International Uniform Response Criteria for Multiple Myeloma (IURC) (see Durie B G M, Harousseau J-L, Miguel J S, et al. International uniform response criteria for multiple myeloma. Leukemia, 2006; (10) 10: 1-7), using the response and endpoint definitions shown below:

| Response Subcategory | Response Criteria[a] |
|---|---|
| sCR | CR as defined below plus Normal FLC ratio and Absence of clonal cells in bone marrow[b] by immunohistochemistry or immunofluorescence[c] |
| CR | Negative immunofixation on the serum and urine and Disappearance of any soft tissue plasmacytomas and <5% plasma cells in bone marrow[b] |
| VGPR | Serum and urine M-protein detectable by immunofixation but not on electrophoresis or 90% or greater reduction in serum M-protein plus urine M-protein level <100 mg per 24 h |
| PR | ≥50% reduction of serum M-protein and reduction in 24-h urinary M-protein by ≥90% or to <200 mg per 24 h If the serum and urine M-protein are unmeasurable,[d] a ≥50% decrease in the difference between involved and uninvolved FLC levels is required in place of the M-protein criteria If serum and urine M-protein are unmeasurable, and serum free light assay is also unmeasurable, ≥50% reduction in plasma cells is required in place of M-protein, provided baseline bone marrow plasma cell percentage was ≥30% In addition to the above listed criteria, if present at baseline, a ≥50% reduction in the size of soft tissue plasmacytomas is also required |

-continued

| Response Subcategory | Response Criteria[a] |
|---|---|
| SD (not recommended for use as an indicator of response; stability of disease is best described by providing the time to progression estimates) | Not meeting criteria for CR, VGPR, PR or progressive disease |

Abbreviations: CR, complete response; FLC, free light chain; PR, partial response; SD, stable disease; sCR, stringent complete response; VGPR, very good partial response;
[a]All response categories require two consecutive assessments made at anytime before the institution of any new therapy; all categories also require no known evidence of progressive or new bone lesions if radiographic studies were performed. Radiographic studies are not required to satisfy these response requirements;
[b]Confirmation with repeat bone marrow biopsy not needed;
[c]Presence/absence of clonal cells is based upon the κ/λ ratio. An abnormal κ/λ ratio by immunohistochemistry and/or immunofluorescence requires a minimum of 100 plasma cells for analysis. An abnormal ratio reflecting presence of an abnormal clone is κ/λ of >4:1 or <1:2.
[d]Measurable disease defined by at least one of the following measurements: Bone marrow plasma cells ≥30%; Serum M-protein ≥1 g/dl (≥10 gm/l)[10 g/l]; Urine M-protein ≥200 mg/24 h; Serum FLC assay: Involved FLC level ≥10 mg/dl (≥100 mg/l); provided serum FLC ratio is abnormal.

In certain embodiments, the treatment of a cancer may be assessed by Response Evaluation Criteria in Solid Tumors (RECIST 1.1) (see Thereasse P., et al. New Guidelines to Evaluate the Response to Treatment in Solid Tumors. J. of the National Cancer Institute; 2000; (92) 205-216 and Eisenhauer E. A., Therasse P., Bogaerts J., et al. New response evaluation criteria in solid tumours: Revised RECIST guideline (version 1.1). European J. Cancer; 2009; (45) 228-247). Overall responses for all possible combinations of tumor responses in target and non-target lesions with our without the appearance of new lesions are as follows:

| Target lesions | Non-target lesions | New lesions | Overall response |
|---|---|---|---|
| CR | CR | No | CR |
| CR | Incomplete response/SD | No | PR |
| PR | Non-PD | No | PR |
| SD | Non-PD | No | SD |
| PD | Any | Yes or no | PD |
| Any | PD | Yes or no | PD |
| Any | Any | Yes | PD |

CR = complete response; PR = partial response; SD = stable disease; and PD = progressive disease.

With respect to the evaluation of target lesions, complete response (CR) is the disappearance of all target lesions, partial response (PR) is at least a 30% decrease in the sum of the longest diameter of target lesions, taking as reference the baseline sum longest diameter, progressive disease (PD) is at least a 20% increase in the sum of the longest diameter of target lesions, taking as reference the smallest sum longest diameter recorded since the treatment started or the appearance of one or more new lesions and stable disease (SD) is neither sufficient shrinkage to qualify for partial response nor sufficient increase to qualify for progressive disease, taking as reference the smallest sum longest diameter since the treatment started.

With respect to the evaluation of non-target lesions, complete response (CR) is the disappearance of all non-target lesions and normalization of tumor marker level; incomplete response/stable disease (SD) is the persistence of one or more non-target lesion(s) and/or the maintenance of tumor marker level above the normal limits, and progressive disease (PD) is the appearance of one or more new lesions and/or unequivocal progression of existing non-target lesions.

The procedures, conventions, and definitions described below provide guidance for implementing the recommendations from the Response Assessment for Neuro-Oncology (RANO) Working Group regarding response criteria for high-grade gliomas (Wen P., Macdonald, D R., Reardon, D A., et al. Updated response assessment criteria for highgrade gliomas: Response assessment in neuro-oncology working group. J Clin Oncol 2010; 28: 1963-1972). Primary modifications to the RANO criteria for Criteria for Time Point Responses (TPR) can include the addition of operational conventions for defining changes in glucocorticoid dose, and the removal of subjects' clinical deterioration component to focus on objective radiologic assessments. The baseline MRI scan is defined as the assessment performed at the end of the post-surgery rest period, prior to re-initiating compound treatment. The baseline MM is used as the reference for assessing complete response (CR) and partial response (PR). Whereas, the smallest SPD (sum of the products of perpendicular diameters) obtained either at baseline or at subsequent assessments will be designated the nadir assessment and utilized as the reference for determining progression. For the 5 days preceding any protocol-defined MM scan, subjects receive either no glucocorticoids or are on a stable dose of glucocorticoids. A stable dose is defined as the same daily dose for the 5 consecutive days preceding the MRI scan. If the prescribed glucocorticoid dose is changed in the 5 days before the baseline scan, a new baseline scan is required with glucocorticoid use meeting the criteria described above. The following definitions will be used.

Measurable Lesions: Measurable lesions are contrast-enhancing lesions that can be measured bidimensionally. A measurement is made of the maximal enhancing tumor diameter (also known as the longest diameter, LD). The greatest perpendicular diameter is measured on the same image. The cross hairs of bidimensional measurements should cross and the product of these diameters will be calculated.

Minimal Diameter: T1-weighted image in which the sections are 5 mm with 1 mm skip. The minimal LD of a measurable lesion is set as 5 mm by 5 mm. Larger diameters may be required for inclusion and/or designation as target lesions. After baseline, target lesions that become smaller than the minimum requirement for measurement or become no longer amenable to bidimensional measurement will be recorded at the default value of 5 mm for each diameter below 5 mm. Lesions that disappear will be recorded as 0 mm by 0 mm.

Multicentric Lesions: Lesions that are considered multicentric (as opposed to continuous) are lesions where there is normal intervening brain tissue between the two (or more) lesions. For multicentric lesions that are discrete foci of enhancement, the approach is to separately measure each enhancing lesion that meets the inclusion criteria. If there is no normal brain tissue between two (or more) lesions, they will be considered the same lesion.

Nonmeasurable Lesions: All lesions that do not meet the criteria for measurable disease as defined above will be considered non-measurable lesions, as well as all nonenhancing and other truly nonmeasurable lesions. Nonmeasurable lesions include foci of enhancement that are less than the specified smallest diameter (i.e., less than 5 mm by 5 mm), nonenhancing lesions (e.g., as seen on T1-weighted post-contrast, T2-weighted, or fluid-attenuated inversion recovery (FLAIR) images), hemorrhagic or predominantly cystic or necrotic lesions, and leptomeningeal tumor. Hemorrhagic lesions often have intrinsic T1-weighted hyperintensity that could be misinterpreted as enhancing tumor, and for this reason, the pre-contrast T1-weighted image may be examined to exclude baseline or interval sub-acute hemorrhage.

At baseline, lesions will be classified as follows: Target lesions: Up to 5 measurable lesions can be selected as target lesions with each measuring at least 10 mm by 5 mm, representative of the subject's disease; Non-target lesions: All other lesions, including all nonmeasurable lesions (including mass effects and T2/FLAIR findings) and any measurable lesion not selected as a target lesion. At baseline, target lesions are to be measured as described in the definition for measurable lesions and the SPD of all target lesions is to be determined. The presence of all other lesions is to be documented. At all post-treatment evaluations, the baseline classification of lesions as target and non-target lesions will be maintained and lesions will be documented and described in a consistent fashion over time (e.g., recorded in the same order on source documents and eCRFs). All measurable and nonmeasurable lesions must be assessed using the same technique as at baseline (e.g., subjects should be imaged on the same MM scanner or at least with the same magnet strength) for the duration of the study to reduce difficulties in interpreting changes. At each evaluation, target lesions will be measured and the SPD calculated. Non-target lesions will be assessed qualitatively and new lesions, if any, will be documented separately. At each evaluation, a time point response will be determined for target lesions, non-target lesions, and new lesion. Tumor progression can be established even if only a subset of lesions is assessed. However, unless progression is observed, objective status (stable disease, PR or CR) can only be determined when all lesions are assessed.

Confirmation assessments for overall time point responses of CR and PR will be performed at the next scheduled assessment, but confirmation may not occur if scans have an interval of <28 days. Best response, incorporating confirmation requirements, will be derived from the series of time points.

In certain embodiments, treatment of a cancer may be assessed by the inhibition of phosphorylation of S6RP, 4E-BP1, AKT and/or DNA-PK in circulating blood and/or tumor cells, and/or skin biopsies or tumor biopsies/aspirates, before, during and/or after treatment with a TOR kinase inhibitor. For example, the inhibition of phosphorylation of S6RP, 4E-BP1, AKT and/or DNA-PK is assessed in B-cells, T-cells and/or monocytes. In other embodiments, treatment of a cancer may be assessed by the inhibition of DNA-dependent protein kinase (DNA-PK) activity in skin samples and/or tumor biopsies/aspirates, such as by assessment of the amount of pDNA-PK S2056 as a biomarker for DNA damage pathways, before, during, and/or after TOR kinase inhibitor treatment. In one embodiment, the skin sample is irradiated by UV light.

In the extreme, complete inhibition, is referred to herein as prevention or chemoprevention. In this context, the term "prevention" includes either preventing the onset of clinically evident cancer altogether or preventing the onset of a preclinically evident stage of a cancer. Also intended to be encompassed by this definition is the prevention of transformation into malignant cells or to arrest or reverse the progression of premalignant cells to malignant cells. This includes prophylactic treatment of those at risk of developing a cancer.

As used herein and unless otherwise indicated, the term "substantially pure" when used to describe a polymorph of a compound, i.e. a crystal form or an amorphous form of a compound, means a crystal form or an amorphous form of the compound that comprises that crystal form or amorphous form and is substantially free of other polymorphs of the compound.

As used herein, and unless otherwise specified, the terms "about" and "approximately," when used in connection with doses, amounts, or weight percent of ingredients of a composition or a dosage form, mean a dose, amount, or weight percent that is recognized by those of ordinary skill in the art to provide a pharmacological effect equivalent to that obtained from the specified dose, amount, or weight percent. Specifically, the terms "about" and "approximately," when used in this context, contemplate a dose, amount, or weight percent within 15%, more specifically within 10%, more specifically within 5%, of the specified dose, amount, or weight percent.

As used herein, and unless otherwise specified, the terms "about" and "approximately," when used in connection with a numeric value or range of values which is provided to characterize a particular solid form, e.g., a specific temperature or temperature range, such as, for example, that describing a melting, dehydration, desolvation or glass transition temperature; a mass change, such as, for example, a mass change as a function of temperature or humidity; a solvent or water content, in terms of, for example, mass or a percentage; or a peak position, such as, for example, in analysis by IR or Raman spectroscopy or XRPD; indicate that the value or range of values may deviate to an extent deemed reasonable to one of ordinary skill in the art while still describing the particular solid form. Specifically, the terms "about" and "approximately," when used in this context, indicate that the numeric value or range of values may vary, in particular embodiments, within 20%, 10%, 9%, 8%, 7%, 6%, 5%, 4%, 3%, 2%, 1.5%, 1%, 0.5%, 0.25% of the recited value or range of values. For example, in some embodiments, the value of an XRPD peak position may vary by up to ±0.2 degrees two theta while still describing the particular XRPD peak.

5.2 Compound 1

The solid forms, formulations and methods of use provided herein relate to Compound 1:

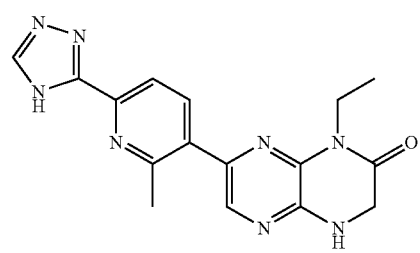

1 having the name 1-ethyl-7-(2-methyl-6-(1H-1,2,4-triazol-3-yl)pyridin-3-yl)-3,4-dihydropyrazino[2,3-b]pyrazin-2(1H)-one, and tautomers.

Tautomers of Compound 1 include the following:

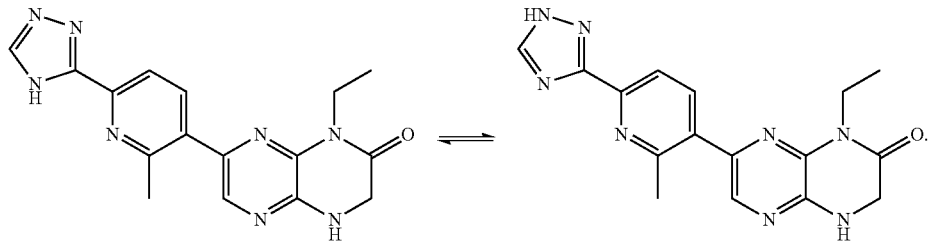 [SMILES: CCN1C(=O)CNc2ncc(-c3ccc(-c4nnc[nH]4)nc3C)nc21 ; CCN1C(=O)CNc2ncc(-c3ccc(-c4nc[nH]n4)nc3C)nc21]

Compound 1 can be prepared using reagents and methods known in the art, including the methods provided in U.S. Pat. No. 8,110,578, filed on Oct. 26, 2009; US Patent Publication Application No. 2011/0137028, filed on Oct. 25, 2010; and U.S. Provisional Patent Application No. 61/813,064, filed on Apr. 17, 2013, the entire contents of each of which are incorporated herein by reference.

It should be noted that if there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

5.3 Solid Forms of Compound 1

In certain embodiments, provided herein are solid forms of Compound 1 or tautomers thereof. In certain embodiments, the solid form is crystalline. In certain embodiments, the solid form is a single-component solid form. In certain embodiments, the solid form is a solvate.

While not intending to be bound by any particular theory, certain solid forms are characterized by physical properties, e.g., stability, solubility and dissolution rate, appropriate for pharmaceutical and therapeutic dosage forms. Moreover, while not wishing to be bound by any particular theory, certain solid forms are characterized by physical properties (e.g., density, compressibility, hardness, morphology, cleavage, stickiness, solubility, water uptake, electrical properties, thermal behavior, solid-state reactivity, physical stability, and chemical stability) affecting particular processes (e.g., yield, filtration, washing, drying, milling, mixing, tableting, flowability, dissolution, formulation, and lyophilization) which make certain solid forms suitable for the manufacture of a solid dosage form. Such properties can be determined using particular analytical chemical techniques, including solid-state analytical techniques (e.g., X-ray diffraction, microscopy, spectroscopy and thermal analysis), as described herein and known in the art.

The solid forms provided herein (e.g., Form 1, Form 2, Form 3, Form 4, Form 5 and amorphous of Compound 1) may be characterized using a number of methods known to a person having ordinary skill in the art, including, but not limited to, single crystal X-ray diffraction, X-ray powder diffraction (XRPD), microscopy (e.g., scanning electron microscopy (SEM)), thermal analysis (e.g., differential scanning calorimetry (DSC), thermal gravimetric analysis (TGA), and hot-stage microscopy), spectroscopy (e.g., infrared, Raman, and solid-state nuclear magnetic resonance), single differential thermal analysis (SDTA), high performance liquid chromatography coupled with mass spectroscopy (HPLC-MS), thermogravimetrical analysis coupled with single differential thermal analysis (TGA-SDTA), and thermogravimetric analysis coupled with mass spectroscopy (TGA-MS). The particle size and size distribution of the solid form provided herein may be determined by conventional methods, such as laser light scattering technique.

The purity of the solid forms provided herein may be determined by standard analytical methods, such as thin layer chromatography (TLC), gel electrophoresis, gas chromatography, high performance liquid chromatography (HPLC), and mass spectrometry (MS).

It should be understood that the numerical values of the peaks of an X-ray powder diffraction pattern may vary slightly from one machine to another or from one sample to another, and so the values quoted are not to be construed as absolute, but with an allowable variability, such as ±0.2 degrees two theta (° 2θ) (see United State Pharmacopoeia, page 2228 (2003)).

5.3.1 Form 1 of Compound 1

In certain embodiments, provided herein is Form 1 of Compound 1.

In one embodiment, Form 1 is an anhydrous form of Compound 1. In another embodiment, Form 1 of Compound 1 is crystalline.

Figure 2:
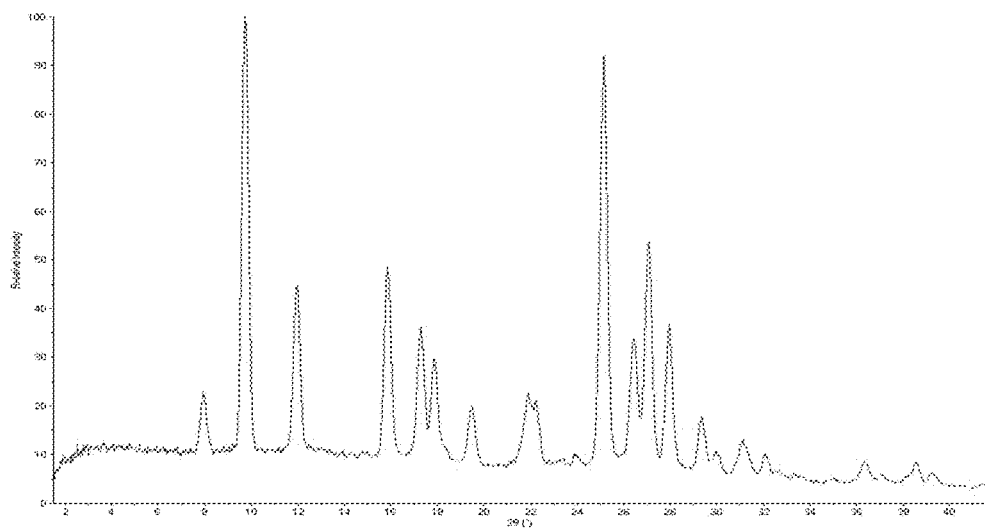
FIG. 2 depicts an X-ray powder diffractogram plot of Form 1 of Compound 1.

In certain embodiments, a solid form provided herein, e.g., Form 1, is substantially crystalline, as indicated by, e.g., X-ray powder diffraction measurements. In one embodiment, Form 1 of Compound 1 has an X-ray powder diffraction pattern substantially as shown in FIG. 2. In one embodiment, Form 1 of Compound 1 has one or more characteristic X-ray powder diffraction peaks at a two-theta angle of approximately 7.94, 9.74, 11.94, 15.86, 17.3, 17.86, 19.46, 25.14, 26.42, 27.06, 27.98 or 29.38 degrees as depicted in FIG. 2. In a specific embodiment, Form 1 of Compound 1 has one, two, three, four, five, six, seven or eight characteristic X-ray powder diffraction peaks at a two-theta angle of approximately 9.74, 11.94, 15.86, 17.3, 25.14, 26.42, 27.06 or 27.98 degrees. In another embodiment, Form 1 of Compound 1 has one, two, three or four characteristic X-ray powder diffraction peaks at a two-theta angle of approximately 9.74, 15.86, 25.14 or 27.06 degrees. In another embodiment, Form 1 of Compound 1 has one, two, three, four, five, six, seven, eight, nine, ten, eleven or twelve characteristic X-ray powder diffraction peaks as set forth in Table 25.

Figure 3:
FIG. 3 depicts a digital image of Form 1 of Compound 1.

In one embodiment, Form 1 of Compound 1 has a digital image substantially as shown in FIG. 3.

Figure 4:
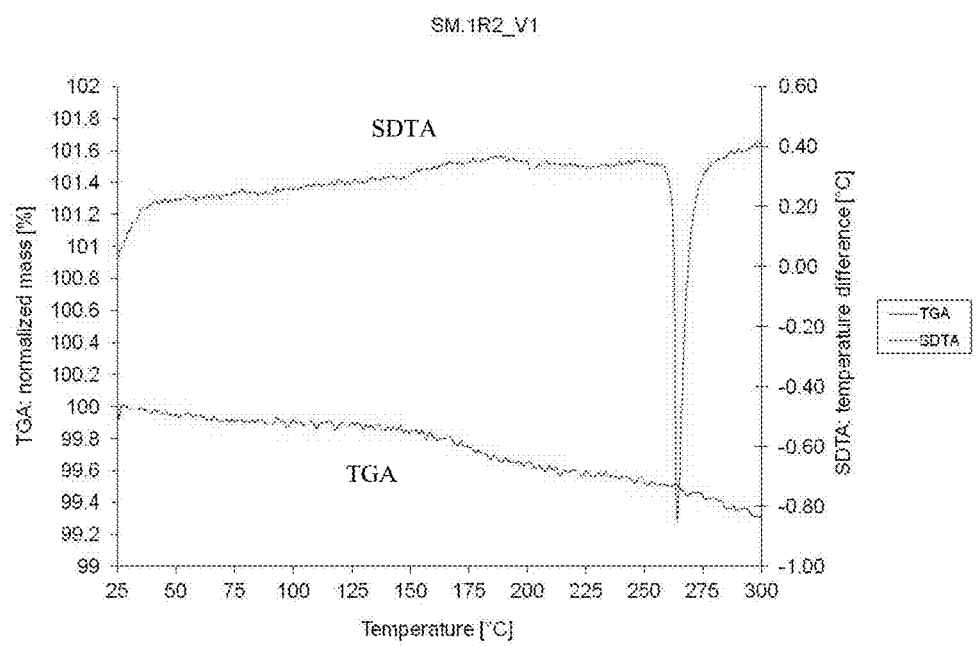
FIG. 4 depicts a thermogravimetrical analysis and single differential thermal analysis of Form 1 of Compound 1.

In one embodiment, provided herein is a crystalline form of Compound 1 having a single differential thermal analysis (SDTA) thermogram as depicted in FIG. 4 comprising an endothermic event between about 240° C. and about 285° C. with a maximum at about 268.9° C. when heated from approximately 25° C. to approximately 300° C. (see Table 24).

Figure 5:
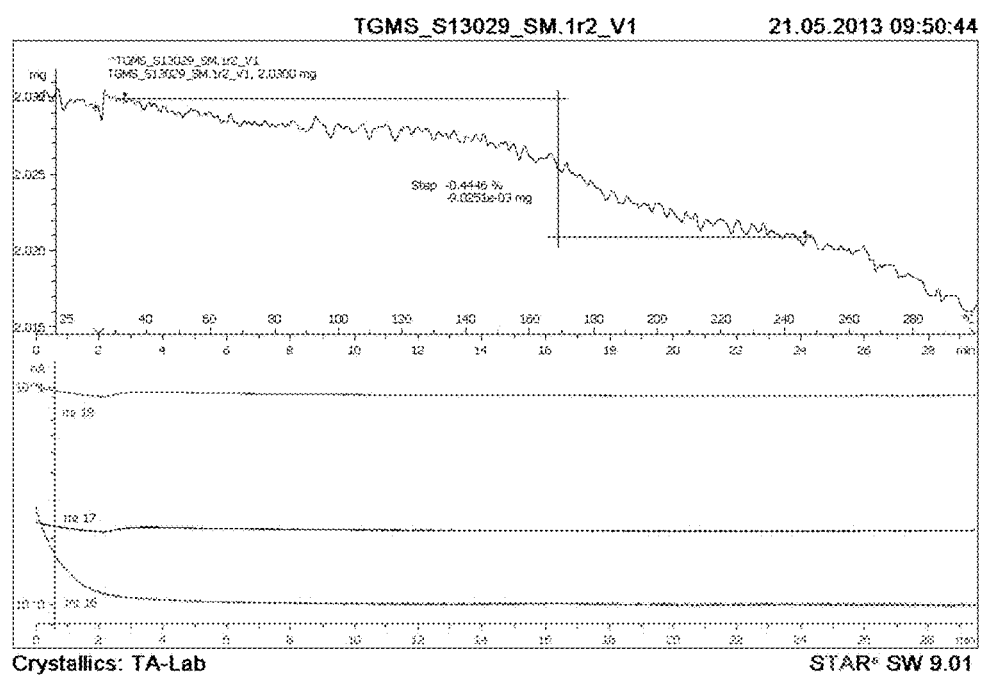
FIG. 5 depicts a thermogravimetric analysis coupled with mass spectroscopy of Form 1 of Compound 1.

In one embodiment, provided herein is a crystalline form of Compound 1 having a thermogravimetric (TGA) thermograph corresponding substantially to the representative TGA thermogram as depicted in FIG. 5. In certain embodiments, the crystalline form exhibits a TGA thermogram comprising a total mass loss of approximately 0.44% of the total mass of the sample between approximately 30° C. and approximately 250° C. when heated from approximately 20° C. to approximately 300° C. Thus, in certain embodiments, the crystalline form loses about 0.44% of its total mass when heated from about ambient temperature to about 300° C.

In still another embodiment, Form 1 of Compound 1 is substantially pure. In certain embodiments, the substantially pure Form 1 of Compound 1 is substantially free of other solid forms, e.g., amorphous form. In certain embodiments, the purity of the substantially pure Form 1 of Compound 1 is no less than about 95% pure, no less than about 96% pure, no less than about 97% pure, no less than about 98% pure, no less than about 98.5% pure, no less than about 99% pure, no less than about 99.5% pure, or no less than about 99.8% pure.

5.3.2 Form 2 of Compound 1

In certain embodiments, provided herein is Form 2 of Compound 1.

In certain embodiments, Form 2 is obtained by crystallization from certain solvent systems, for example, solvent systems comprising one or more of the following solvents or solvent combinations: 1,2-ethanediol and THF. In certain embodiments, Form 2 provided herein is obtained by slurry crystallization, evaporation crystallization or thermocycling crystallization (see Table 23).

In certain embodiments, provided herein are methods for making Form 2 of Compound 1, comprising obtaining a slurry of Form 1 of Compound 1 in a solvent, stirring the slurry, collecting solid from the slurry by filtration (e.g., centrifuge filtration) and optionally washing (e.g., washing with the solvent) and drying. In certain embodiments, provided herein are methods for making Form 2 of Compound 1, comprising obtaining a slurry of Compound 1 in 1,2-ethanediol, stirring the slurry, collecting solid from the slurry by centrifuge filtration and optionally washing with 1,2-ethanediol and drying.

In certain embodiments, provided herein are methods for making Form 2 of Compound 1, comprising dissolving Form 1 of Compound 1 in a solvent to yield a solution, filtering the solution if Form 1 does not dissolve completely, and evaporating the solution under certain air pressure to yield a solid. In certain embodiments, provided herein are methods for making Form 2 of Compound 1, comprising dissolving Form 1 of Compound 1 in 1,2-ethanediol/THF (50/50) to yield a solution, filtering the solution if Form 1 does not dissolve completely, and evaporating the solution under 200 mbar air pressure to yield a solid.

In certain embodiments, provided herein are methods for making Form 2 of Compound 1, comprising 1) obtaining a slurry of Form 1 of Compound 1 in a solvent; 2) heating the slurry until a first temperature (e.g., about 30° C. to about 50° C.); 3) cooling the slurry to a second temperature (e.g., about −5° C. to about 15° C.); 4) keeping the slurry at the second temperature for a period of time; 5) stirring the slurry during steps 1-5; 6) repeating steps 2-5 (e.g., from 6 to 10 times); and 7) filtering the slurry to yield a solid. In certain embodiments, provided herein are methods for making Form 2 of Compound 1, comprising 1) obtaining a slurry of Form 1 of Compound 1 in 1,2-ethanediol; 2) heating the slurry to about 40° C.; 3) cooling the slurry to about 5° C.; 4) keeping the slurry at about 5° C. for about 30 minutes; 5) stirring the slurry during steps 1-5; 6) repeating steps 2-5 8 times; and 7) filtering the slurry to yield a solid.

In one embodiment, Form 2 is a 1,2-ethanediol solvated form of Compound 1. In one embodiment, Form 2 is a 1,2-ethanediol mono-solvated form of Compound 1. In another embodiment, Form 2 of Compound 1 is crystalline.

Figure 7:
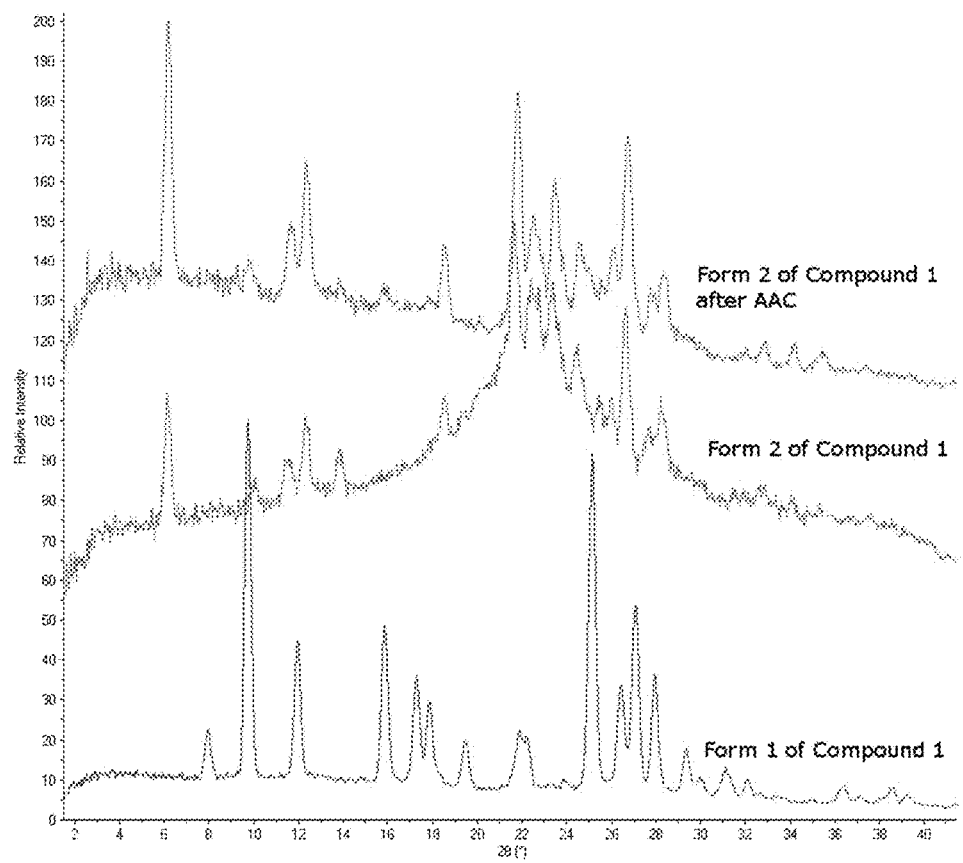
FIG. 7 depicts an X-ray powder diffractogram stack plot of Form 1, Form 2, and Form 2 after exposure to accelerated aging conditions (AAC) of Compound 1.

In certain embodiments, a solid form provided herein, e.g., Form 2, is substantially crystalline, as indicated by, e.g., X-ray powder diffraction measurements. In one embodiment, Form 2 of Compound 1 has an X-ray powder diffraction pattern substantially as shown in FIG. 7 (middle pattern). In one embodiment, Form 2 of Compound 1 has one or more characteristic X-ray powder diffraction peaks at a two-theta angle of approximately 6.18, 10.02, 11.54, 12.34, 13.86, 18.54, 21.74, 22.5, 23.42, 24.54, 25.5, 26.02, 26.7, 27.82, 28.34 or 34.14 degrees as depicted in FIG. 7. In a specific embodiment, Form 2 of Compound 1 has one, two, three, four, five, six, seven or eight characteristic X-ray powder diffraction peaks at a two-theta angle of approximately 6.18, 12.34, 18.54, 21.74, 22.5, 23.42, 26.7 or 28.34 degrees. In another embodiment, Form 2 of Compound 1 has one, two, three or four characteristic X-ray powder diffraction peaks at a two-theta angle of approximately 6.18, 12.34, 21.74 or 26.7 degrees. In another embodiment, Form 2 of Compound 1 has one, two, three, four, five, six, seven, eight, nine, ten, eleven, twelve, thirteen, fourteen, fifteen or sixteen characteristic X-ray powder diffraction peaks as set forth in Table 26.

In one embodiment, Form 2 of Compound 1 has a digital image substantially as shown in FIG. 8A.

Figure 10:
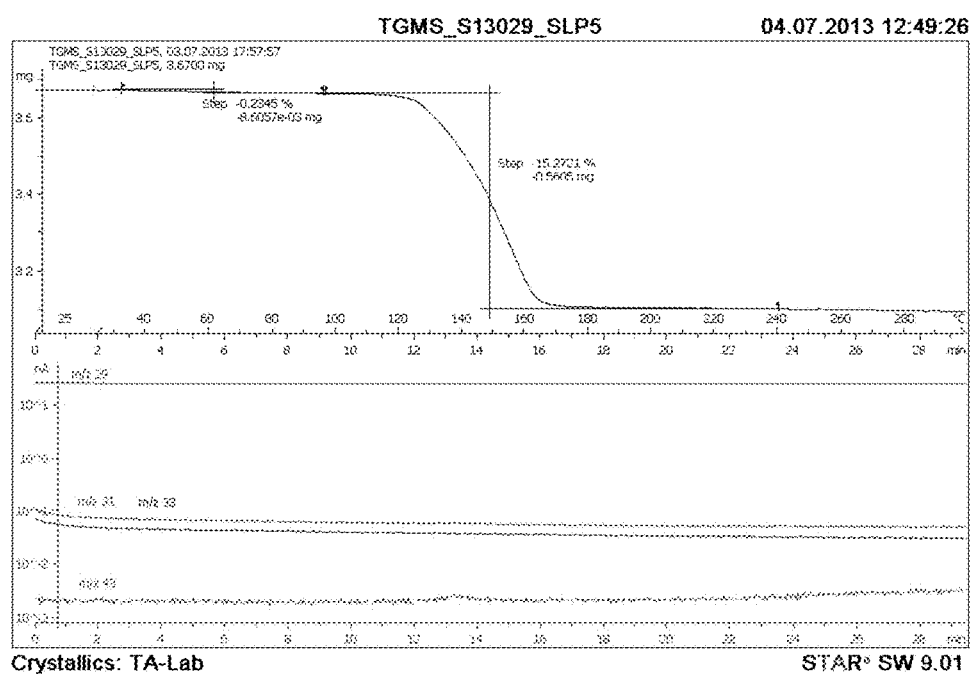
FIG. 10 depicts a thermogravimetric analysis coupled with mass spectroscopy of Form 2 of Compound 1.

In one embodiment, provided herein is a crystalline form of Compound 1 having a thermogravimetric (TGA) thermograph corresponding substantially to the representative TGA thermogram as depicted in FIG. 10. In certain embodiments, the crystalline form exhibits a TGA thermogram comprising a total mass loss of approximately 15.5% of the total mass of the sample between approximately 95° C. and approximately 175° C. when heated from approximately 25° C. to approximately 300° C. Thus, in certain embodiments, the crystalline form loses about 15.5% of its total mass when heated from about ambient temperature to about 300° C. In certain embodiments, the crystalline form contains 1 molar equivalent of solvent in the crystal lattice corresponding to approximately 1 mole of 1,2-ethanediol per mole of Compound 1. The theoretical 1,2-ethanediol content of a 1,2-ethanediol mono-solvate of Compound 1 is 15.6% by weight, matching the TGA weight loss observed. In certain embodiments, the crystalline form is a 1,2-ethanediol monosolvate of Compound 1.

Figure 9:
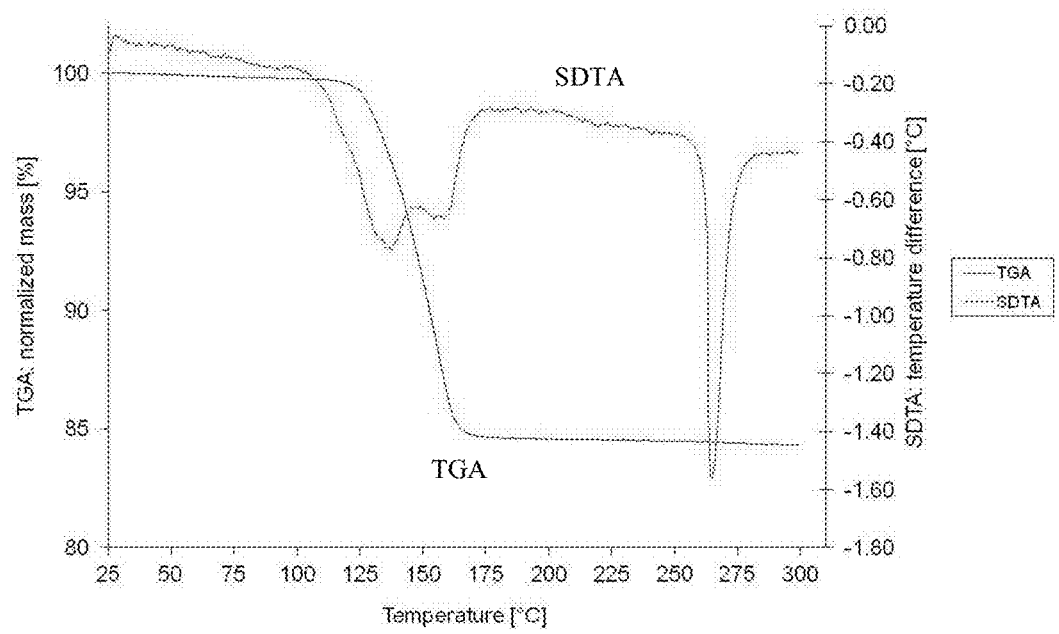
FIG. 9 depicts a thermogravimetrical analysis and single differential thermal analysis of Form 2 of Compound 1.

In one embodiment, provided herein is a crystalline form of Compound 1 having a single differential thermal analysis (SDTA) thermogram as depicted in FIG. 9 comprising an endothermic event between about 95° C. and about 176° C. with a maximum at about 137° C. when heated from approximately 25° C. to approximately 300° C. (see Table 24).

In one embodiment, provided herein is a crystalline form of Compound 1 having a single differential thermal analysis (SDTA) thermogram as depicted in FIG. 9 comprising an endothermic event between about 240° C. and about 285° C. with a maximum at about 264° C. when heated from approximately 25° C. to approximately 300° C. (see Table 24).

In still another embodiment, Form 2 of Compound 1 is substantially pure. In certain embodiments, the substantially pure Form 2 of Compound 1 is substantially free of other solid forms, e.g., amorphous form. In certain embodiments, the purity of the substantially pure Form 2 of Compound 1 is no less than about 95% pure, no less than about 96% pure, no less than about 97% pure, no less than about 98% pure, no less than about 98.5% pure, no less than about 99% pure, no less than about 99.5% pure, or no less than about 99.8% pure.

5.3.3 Form 3 of Compound 1

In certain embodiments, provided herein is Form 3 of Compound 1.

In certain embodiments, Form 3 is obtained by crystallization from certain solvent systems, for example, solvent systems comprising one or more of the following solvents or solvent combinations: 2,2,2-trifluoroethanol (TFE) combined with either water or cyclohexane, chloroform and the solvent mixture of isopropanol and acetone. In certain embodiments, Form 3 is obtained by evaporative crystallization, hot-filtration crystallization, vapor diffusion into liquid crystallization or vapor diffusion onto solid crystallization (see Table 23).

In certain embodiments, provided herein are methods for making Form 3 of Compound 1, comprising mixing Form 1 of Compound 1 with a solvent or solvent mixture, filtering the mixture to yield a solution if Form 1 does not dissolve completely, and evaporating the solution under certain air pressure to yield a solid. In certain embodiments, provided herein are methods for making Form 3 of Compound 1, comprising mixing Form 1 of Compound 1 with a 1:1 solution of TFE and water, filtering the mixture to yield a solution if Form 1 does not dissolve completely, and evaporating the solution of TFE and water under 200 mbar air pressure to yield a solid.

In certain embodiments, provided herein are methods for making Form 3 of Compound 1, comprising obtaining a slurry of Form 1 of Compound 1 in a solvent, heating the slurry to a first temperature (e.g., about 50° C. to about 70° C.), filtering the slurry to yield a solution, cooling down the solution to a second temperature (e.g., about 15° C. to about 35° C.) to yield solid precipitation, and collecting the solid. In certain embodiments, provided herein are methods for making Form 3 of Compound 1, comprising obtaining a slurry of Form 1 of Compound 1 in a 1:1 solution of acetone and isopropanol, heating the slurry to about 60° C., filtering the slurry to yield a solution, cooling down the solution to about 25° C. to yield solid precipitation, and collecting the solid.

In certain embodiments, provided herein are methods for making Form 3 of Compound 1, comprising obtaining a saturated solution of Form 1 of Compound 1 in a solvent, diffusing an anti-solvent into the saturated solution, collecting precipitated solid if there is precipitation, and evaporating the solvent to collect solid if there is no precipitation. In certain embodiments, provided herein are methods for making Form 3 of Compound 1, comprising obtaining a saturated solution of Form 1 of Compound 1 in TFE, diffusing cyclohexane into the saturated solution, collecting precipitated solid if there is precipitation, and evaporating the solvent to collect solid if there is no precipitation.

In certain embodiments, provided herein are methods for making Form 3 of Compound 1, comprising obtaining amorphous form of Compound 1, diffusing a solvent on to the amorphous form of Compound 1 for a period of time (e.g., about 1 week to about 1 month), and collecting the solid. In certain embodiments, provided herein are methods for making Form 3 of Compound 1, comprising obtaining amorphous form of Compound 1 by grinding Form 1 of Compound 1 for about two hours, diffusing chloroform on to the amorphous form of Compound 1 for about two weeks, and collecting the solid.

In one embodiment, Form 3 is a 2,2,2-trifluoroethanol solvated form of Compound 1. In one embodiment, Form 3 is a 2,2,2-trifluoroethanol hemi-solvated form of Compound 1. In another embodiment, Form 3 of Compound 1 is crystalline.

In one embodiment, Form 3 is a chloroform solvated form of Compound 1. In one embodiment, Form 3 is a chloroform hemi-solvated form of Compound 1.

In one embodiment, Form 3 is an acetone solvated form of Compound 1. In one embodiment, Form 3 is an acetone hemi-solvated form of Compound 1.

In one embodiment, Form 3 is an isopropanol solvated form of Compound 1. In one embodiment, Form 3 is an isopropanol hemi-solvated form of Compound 1.

Figure 12:
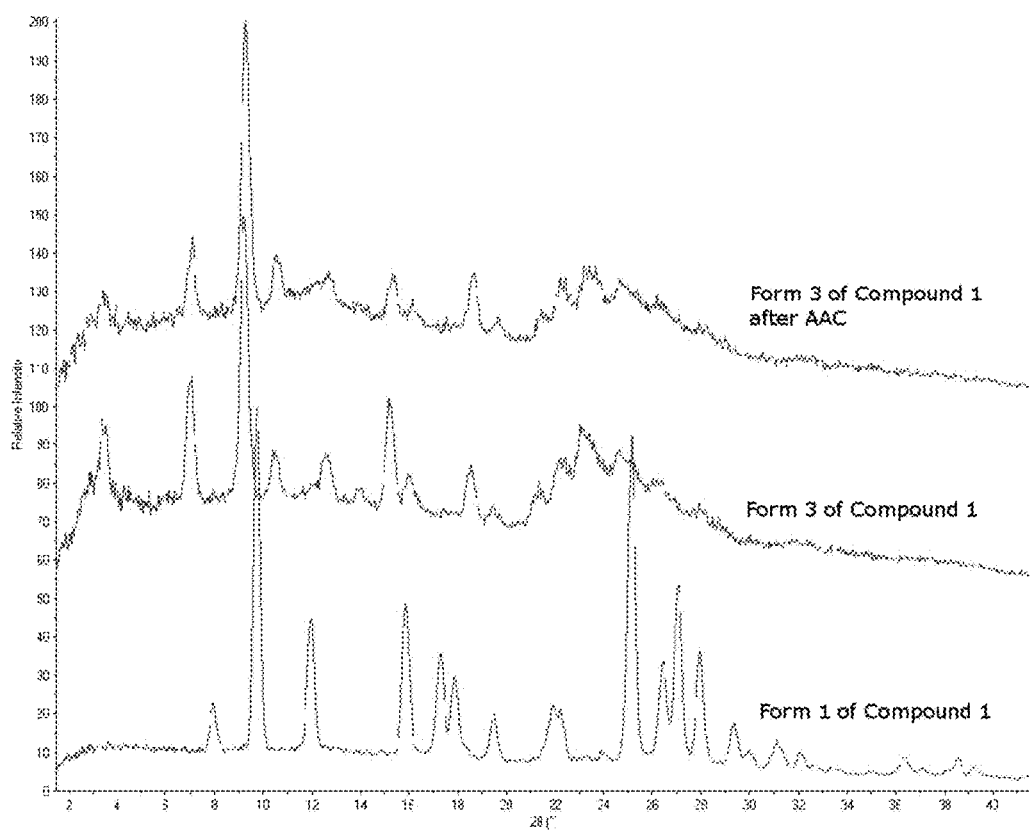
FIG. 12 depicts an X-ray powder diffractogram stack plot of Form 1, Form 3, and Form 3 after exposure to accelerated aging conditions (AAC) of Compound 1.

In certain embodiments, a solid form provided herein (e.g., Form 3) is substantially crystalline, as indicated by, e.g., X-ray powder diffraction measurements. In one embodiment, Form 3 of Compound 1 has an X-ray powder diffraction pattern substantially as shown in FIG. 12 (middle pattern). In one embodiment, Form 3 of Compound 1 has one or more characteristic X-ray powder diffraction peaks at a two-theta angle of approximately 3.5, 7.06, 9.26, 10.5, 12.66, 15.3 or 18.62 degrees as depicted in FIG. 12. In another embodiment, Form 3 of Compound 1 has one, two, three or four characteristic X-ray powder diffraction peaks at a two-theta angle of approximately 3.5, 9.26, 15.3 or 18.62 degrees. In another embodiment, Form 3 of Compound 1 has one, two, three, four, five, six or seven characteristic X-ray powder diffraction peaks as set forth in Table 27.

In one embodiment, Form 3 of Compound 1 has a digital image substantially as shown in FIG. 13A.

Figure 15:
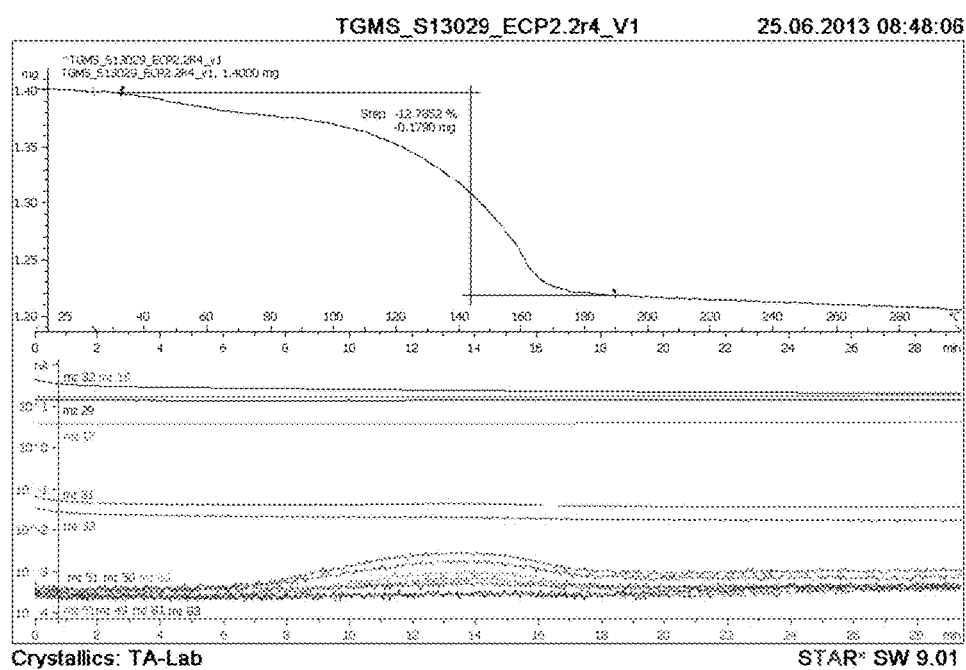
FIG. 15 depicts a thermogravimetric analysis coupled with mass spectroscopy of Form 3 of Compound 1.

In one embodiment, provided herein is a crystalline form of Compound 1 having a thermogravimetric (TGA) thermograph corresponding substantially to the representative TGA thermogram as depicted in FIG. 15. In certain embodiments, the crystalline form exhibits a TGA thermogram comprising a total mass loss of approximately 12.8% of the total mass of the sample between approximately 35° C. and approximately 190° C. when heated from approximately 25° C. to approximately 300° C. Thus, in certain embodiments, the crystalline form loses about 12.8% of its total mass when heated from about ambient temperature to about 300° C. In certain embodiments, the crystalline form contains 0.5 molar equivalents of solvent in the crystal lattice corresponding to approximately 0.5 mole of 2,2,2-trifluoroethanol per mole of Compound 1. The theoretical 2,2,2-trifluoroethanol content of a 2,2,2-trifluoroethanol hemi-solvate of Compound 1 is 11.5% by weight, matching the TGA weight loss observed. In certain embodiments, the crystalline form is a 2,2,2-trifluoroethanol hemi-solvate of Compound 1.

Figure 14:
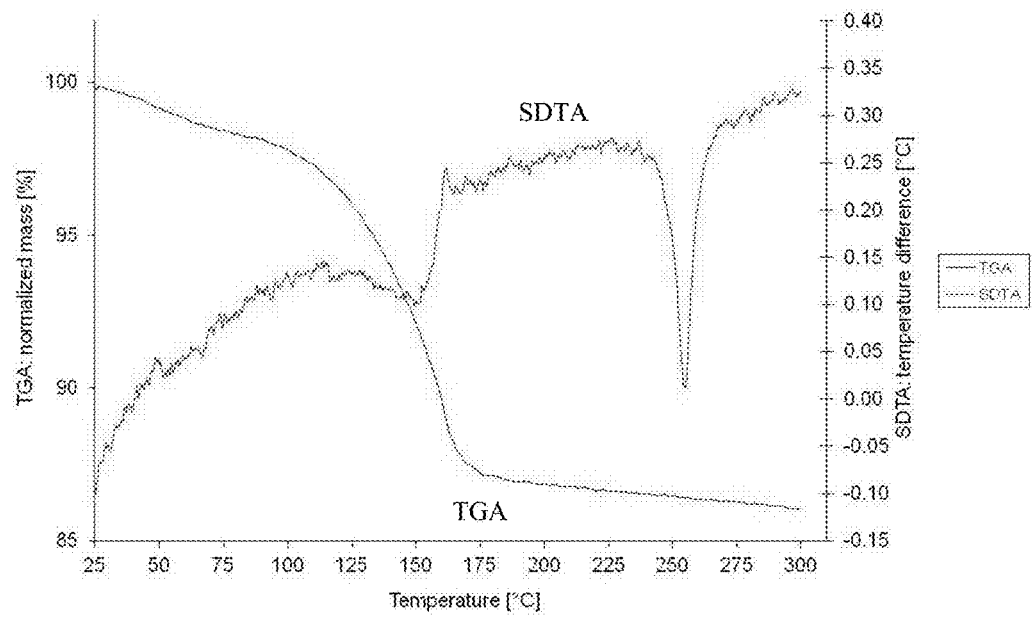
FIG. 14 depicts a thermogravimetrical analysis and single differential thermal analysis of Form 3 of Compound 1.

In one embodiment, provided herein is a crystalline form of Compound 1 having a single differential thermal analysis (SDTA) thermogram as depicted in FIG. 14 comprising an endothermic event between about 110° C. and about 175° C. with a maximum at about 149° C. when heated from approximately 25° C. to approximately 300° C. (see Table 24).

In one embodiment, provided herein is a crystalline form of Compound 1 having a SDTA thermogram comprising an endothermic event as depicted in FIG. 14 between about 225° C. and about 275° C. with a maximum at about 254° C. when heated from approximately 25° C. to approximately 300° C. (see Table 24).

In still another embodiment, Form 3 of Compound 1 is substantially pure. In certain embodiments, the substantially pure Form 3 of Compound 1 is substantially free of other solid forms, e.g., amorphous form. In certain embodiments, the purity of the substantially pure Form 3 of Compound 1 is no less than about 95% pure, no less than about 96% pure, no less than about 97% pure, no less than about 98% pure, no less than about 98.5% pure, no less than about 99% pure, no less than about 99.5% pure, or no less than about 99.8% pure.

5.3.4 Form 4 of Compound 1

In certain embodiments, provided herein is Form 4 of Compound 1.

In certain embodiments, Form 4 is obtained by crystallization from certain solvent systems, for example, solvent systems comprising one or more of the following solvents or solvent combinations: dimethylsulfoxide, water and toluene. In certain embodiments, Form 4 is obtained by anti-solvent crystallization and vapor diffusion into liquid crystallization.

In certain embodiments, provided herein are methods for making Form 4 of Compound 1, comprising dissolving Form 1 of Compound 1 in a solvent, adding an anti-solvent, collecting solid from the solution by filtration, and optionally washing (e.g., washing with the mixture of solvent and anti-solvent at the same ratio of the solution) and drying. In certain embodiments, provided herein are methods for making Form 4 of Compound 1, comprising dissolving Form 1 of Compound 1 in dimethylsulfoxide, adding water, collecting solid from the solution by filtration, and optionally washing with the mixture of dimethylsulfoxide and water at the same ratio of the solution and drying. In certain embodiments, provided herein are methods for making Form 4 of Compound 1, comprising dissolving Form 1 of Compound 1 in dimethylsulfoxide, adding toluene, collecting solid from the solution by filtration, and optionally washing with the mixture of dimethylsulfoxide and toluene at the same ratio of the solution and drying.

In certain embodiments, provided herein are methods for making Form 4 of Compound 1, comprising obtaining a saturated solution of Form 1 of Compound 1 in a solvent, diffusing an anti-solvent into the saturated solution, collecting precipitated solid if there is precipitation, and evaporating the solvent to collect solid if there is no precipitation. In certain embodiments, provided herein are methods for making Form 4 of Compound 1, comprising obtaining a saturated solution of Form 1 of Compound 1 in DMSO, diffusing water into the saturated solution, collecting precipitated solid if there is precipitation, and evaporating the solvent to collect solid if there is no precipitation.

In one embodiment, Form 4 is a dimethylsulfoxide solvated form of Compound 1. In one embodiment, Form 4 is a 0.8 molar equivalent dimethylsulfoxide solvated form of Compound 1. In another embodiment, Form 4 of Compound 1 is crystalline.

Figure 17:
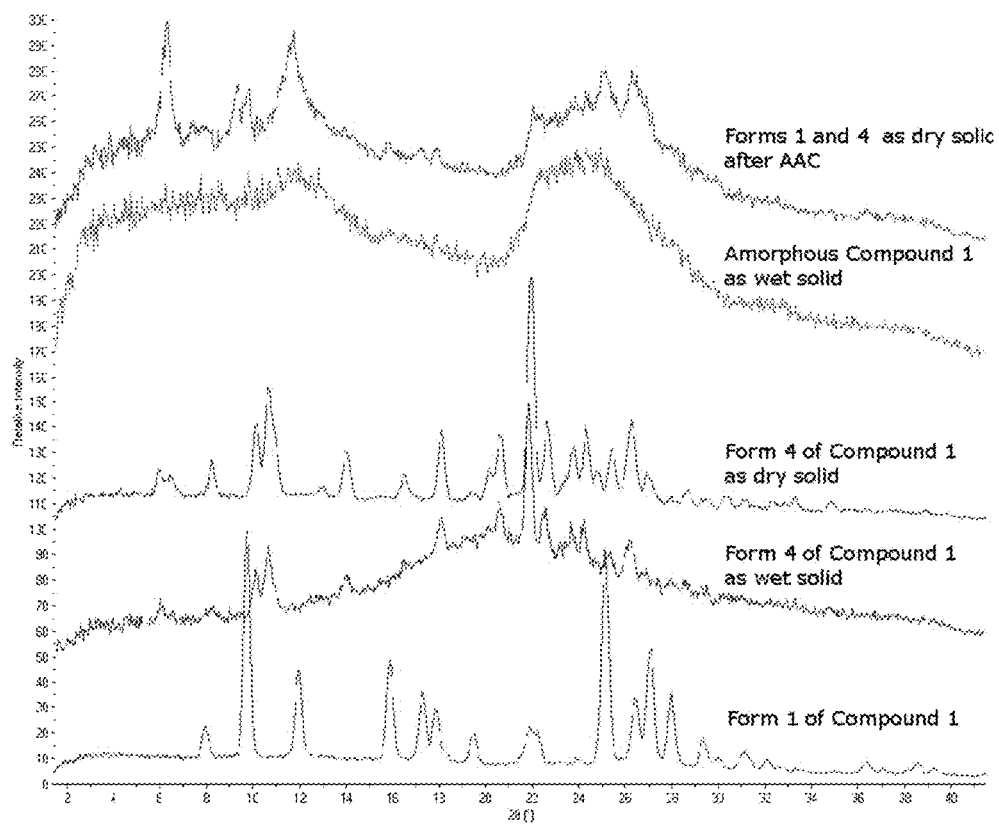
FIG. 17 depicts an X-ray powder diffractogram stack plot of Form 1, Form 4 as wet solid, Form 4 as dry solid, amorphous form of Compound 1 and the mixture of Forms 1 and 4 as dry solid after exposure to accelerated aging conditions (AAC) of Compound 1.

In certain embodiments, a solid form provided herein, e.g., Form 4, is substantially crystalline, as indicated by, e.g., X-ray powder diffraction measurements. In one embodiment, Form 4 of Compound 1 has an X-ray powder diffraction pattern substantially as shown in FIG. 17 (middle pattern). In one embodiment, Form 4 of Compound 1 has one or more characteristic X-ray powder diffraction peaks at a two-theta angle of approximately 8.22, 10.14, 10.66, 14.02, 18.1, 20.62, 21.94, 22.66, 23.78, 24.34, 25.42 or 26.26 degrees as depicted in FIG. 17. In a specific embodiment, Form 4 of Compound 1 has one, two, three, four, five, six, seven or eight characteristic X-ray powder diffraction peaks at a two-theta angle of approximately 10.14, 10.66, 18.1, 20.62, 21.94, 22.66, 24.34 or 26.26 degrees. In another embodiment, Form 4 of Compound 1 has one, two, three or four characteristic X-ray powder diffraction peaks at a two-theta angle of approximately 10.14, 10.66, 21.94 or 26.26 degrees. In another embodiment, Form 4 of Compound 1 has one, two, three, four, five, six, seven, eight, nine, ten, eleven or twelve characteristic X-ray powder diffraction peaks as set forth in Table 28.

In one embodiment, Form 4 of Compound 1 as wet solid has a digital image substantially as shown in FIG. 18A. In one embodiment, Form 4 of Compound 1 as dry solid has a digital image substantially as shown in FIG. 18B.

Figure 20:
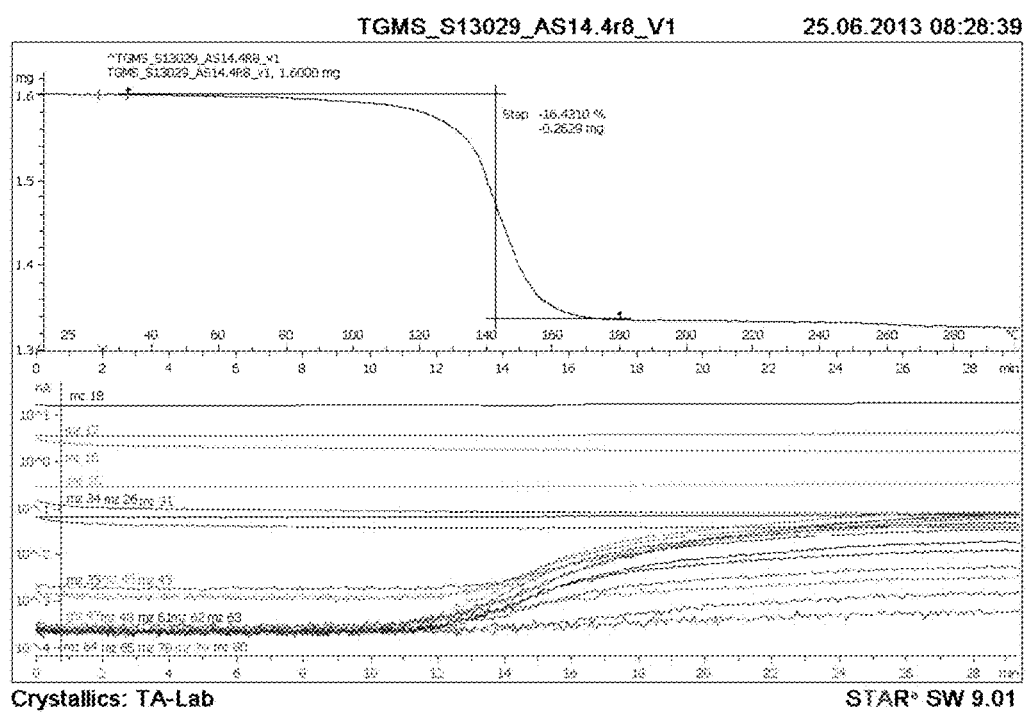
FIG. 20 depicts a thermogravimetric analysis coupled with mass spectroscopy of Form 4 of Compound 1.

In one embodiment, provided herein is a crystalline form of Compound 1 having a thermogravimetric (TGA) thermograph corresponding substantially to the representative TGA thermogram as depicted in FIG. 20. In certain embodiments, the crystalline form exhibits a TGA thermogram comprising a total mass loss of approximately 16.4% of the total mass of the sample between approximately 35° C. and approximately 180° C. when heated from approximately 25° C. to approximately 300° C. Thus, in certain embodiments, the crystalline form loses about 16.4% of its total mass when heated from about ambient temperature to about 300° C. In certain embodiments, the crystalline form contains 0.8 molar equivalents of solvent in the crystal lattice corresponding to approximately 0.8 mole of dimethylsulfoxide per mole of Compound 1. The theoretical dimethylsulfoxide content of a 0.8 molar equivalent dimethylsulfoxide solvate of Compound 1 is 18.9% by weight, matching the TGA weight loss observed. In certain embodiments, the crystalline form is a 0.8 molar equivalent dimethylsulfoxide solvate of Compound 1.

Figure 19:
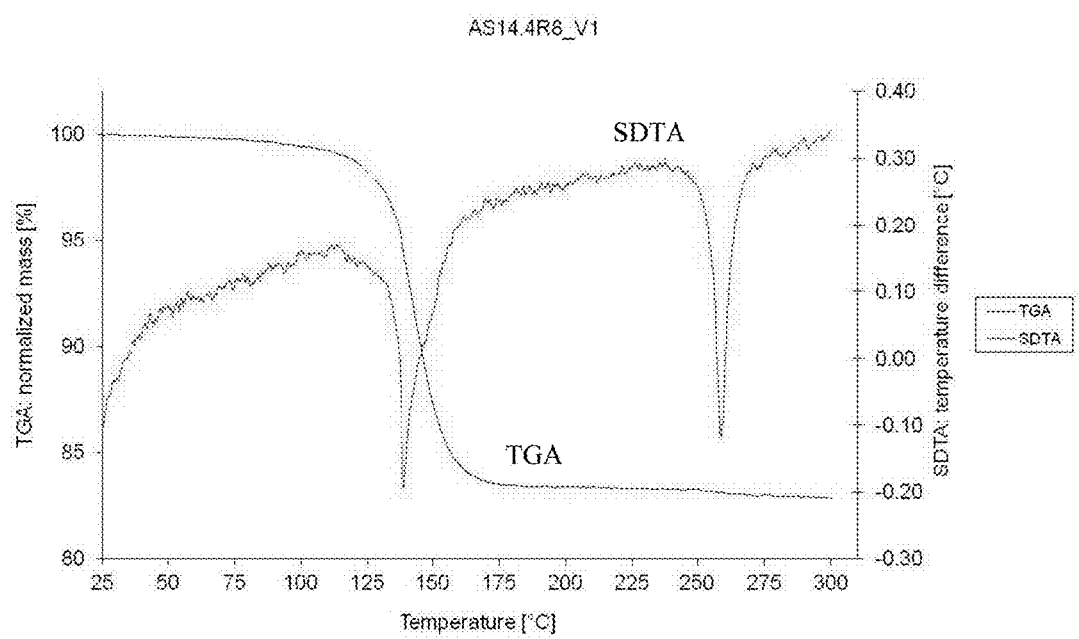
FIG. 19 depicts a thermogravimetrical analysis and single differential thermal analysis of Form 4 of Compound 1.

In one embodiment, provided herein is a crystalline form of Compound 1 having a SDTA thermogram as depicted in FIG. 19 comprising an endothermic event between about 100° C. and about 175° C. with a maximum at about 139° C. when heated from approximately 25° C. to approximately 300° C. (see Table 24).

In one embodiment, provided herein is a crystalline form of Compound 1 having a SDTA thermogram as depicted in FIG. 19 comprising an endothermic event between about 235° C. and about 275° C. with a maximum at about 258° C. when heated from approximately 25° C. to approximately 300° C. (see Table 24).

In still another embodiment, Form 4 of Compound 1 is substantially pure. In certain embodiments, the substantially pure Form 4 of Compound 1 is substantially free of other solid forms, e.g., amorphous form. In certain embodiments, the purity of the substantially pure Form 4 of Compound 1 is no less than about 95% pure, no less than about 96% pure, no less than about 97% pure, no less than about 98% pure, no less than about 98.5% pure, no less than about 99% pure, no less than about 99.5% pure, or no less than about 99.8% pure.

5.3.5 Form 5 of Compound 1

In certain embodiments, provided herein is Form 5 of Compound 1.

In certain embodiments, Form 5 is obtained by crystallization from certain solvent systems, for example, solvent systems comprising one or more of the following solvents or solvent combinations: THF, water, 1,4-dioxane, methanol and ethanol. In certain embodiments, Form 5 is obtained by hot-filtration crystallization, anti-solvent crystallization or evaporative crystallization.

In certain embodiments, provided herein are methods for making Form 5 of Compound 1, comprising obtaining a slurry of Form 1 of Compound 1 in a solvent, heating the slurry to a temperature (e.g., about 50° C. to about 70° C.) for a period of time (e.g., about 10 minutes to about 2 hours), filtering the slurry to yield a solution, cooling down the solution to a temperature (e.g., about 10° C. to about 35° C.), collecting solid from the solution by filtration, and optionally washing (e.g., washing with the solvent) and drying. In certain embodiments, provided herein are methods for making Form 5 of Compound 1, comprising obtaining a slurry of Form 1 of Compound 1 in a solvent mixture of THF and water (50/50), heating the slurry at about 60° C. for about one hour, filtering the slurry to yield a solution, cooling down the solution to about 25° C., collecting solid from the solution by filtration, and optionally washing with the solvent mixture of THF and water (50/50) and drying. In certain embodiments, provided herein are methods for making Form 5 of Compound 1, comprising obtaining a slurry of Form 1 of Compound 1 in a solvent mixture of methanol and water (50/50), heating the slurry at about 60° C. for about one hour, filtering the slurry to yield a solution, cooling down the solution to about 25° C., collecting solid from the solution by filtration, and optionally washing with the solvent mixture of methanol and water (50/50) and drying. In certain embodiments, provided herein are methods for making Form 5 of Compound 1, comprising obtaining a slurry of Form 1 of Compound 1 in a solvent mixture of 1,4-dioxane and water (50/50), heating the slurry at about 60° C. for about one hour, filtering the slurry to yield a solution, cooling down the solution to about 25° C., collecting solid from the solution by filtration, and optionally washing with the solvent mixture of 1,4-dioxane and water (50/50) and drying. In certain embodiments, provided herein are methods for making Form 5 of Compound 1, comprising obtaining a slurry of Form 1 of Compound 1 in a solvent mixture of ethanol and water (50/50), heating the slurry at about 60° C. for about one hour, filtering the slurry to yield a solution, cooling down the solution to about 25° C., collecting solid from the solution by filtration, and optionally washing with solvent mixture of ethanol and water (50/50) and drying.

In certain embodiments, provided herein are methods for making Form 5 of Compound 1, comprising obtaining a saturated solution of Form 1 of Compound 1 in a solvent, diffusing an anti-solvent into the saturated solution, collecting precipitated solid if there is precipitation, and evaporating the solvent to collect solid if there is no precipitation. In certain embodiments, provided herein are methods for making Form 5 of Compound 1, comprising obtaining a saturated solution of Form 1 of Compound 1 in THF, diffusing water into the saturated solution, collecting precipitated solid if there is precipitation, and evaporating the solvent to collect solid if there is no precipitation.

In certain embodiments, provided herein are methods for making Form 5 of Compound 1, comprising mixing Form 5 of Compound 1 with a solvent, filtering the mixture to yield a solution if Form 1 does not dissolve completely, and evaporating the solution under certain air pressure to yield solid. In certain embodiments, provided herein are methods for making Form 5 of Compound 1, comprising mixing Form 1 of Compound 1 with THF/water (50:50), filtering the mixture to yield a solution if Form 1 does not dissolve completely, and evaporating the solution under 200 mbar air pressure to yield solid.

In one embodiment, Form 5 is a hydrated form of Compound 1. In one embodiment, Form 5 is a dihydrated form of Compound 1. In another embodiment, Form 5 of Compound 1 is crystalline.

Figure 22:
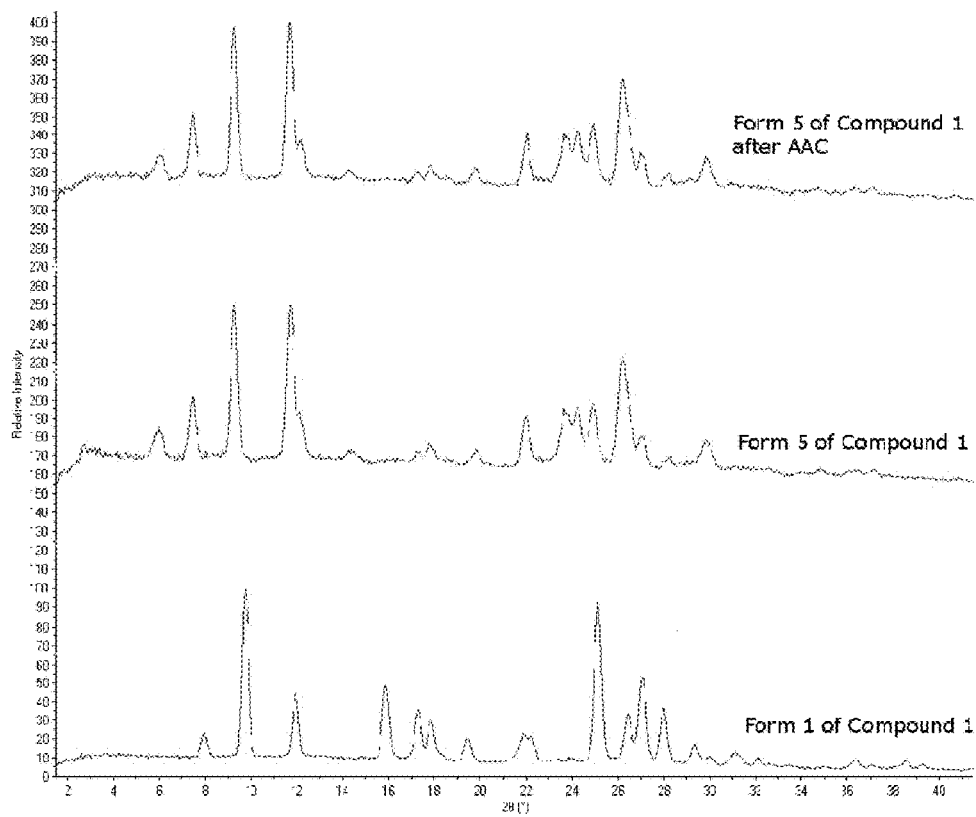
FIG. 22 depicts an X-ray powder diffractogram stack plot of Form 1, Form 5, and Form 5 after exposure to accelerated aging conditions (AAC) of Compound 1.

In certain embodiments, a solid form provided herein, e.g., Form 5, is substantially crystalline, as indicated by, e.g., X-ray powder diffraction measurements. In one embodiment, Form 5 of Compound 1 has an X-ray powder diffraction pattern substantially as shown in FIG. 22 (middle pattern). In one embodiment, Form 5 of Compound 1 has one or more characteristic X-ray powder diffraction peaks at a two-theta angle of approximately 6.02, 7.46, 9.26, 11.7, 12.18, 19.78, 22.02, 23.74, 24.26, 24.94, 26.18, 27.06 or 29.86 degrees as depicted in FIG. 22. In a specific embodiment, Form 5 of Compound 1 has one, two, three, four, five, six, seven or eight characteristic X-ray powder diffraction peaks at a two-theta angle of approximately 7.46, 9.26, 11.7, 22.02, 23.74, 24.26, 24.94 or 26.18 degrees. In another embodiment, Form 5 of Compound 1 has one, two, three or four characteristic X-ray powder diffraction peaks at a two-theta angle of approximately 9.26, 11.7, 24.94 or 26.18 degrees. In another embodiment, Form 5 of Compound 1 has one, two, three, four, five, six, seven, eight, nine, ten, eleven, twelve or thirteen characteristic X-ray powder diffraction peaks as set forth in Table 29.

In one embodiment, Form 5 of Compound 1 has a digital image substantially as shown in FIG. 23A.

Figure 25:
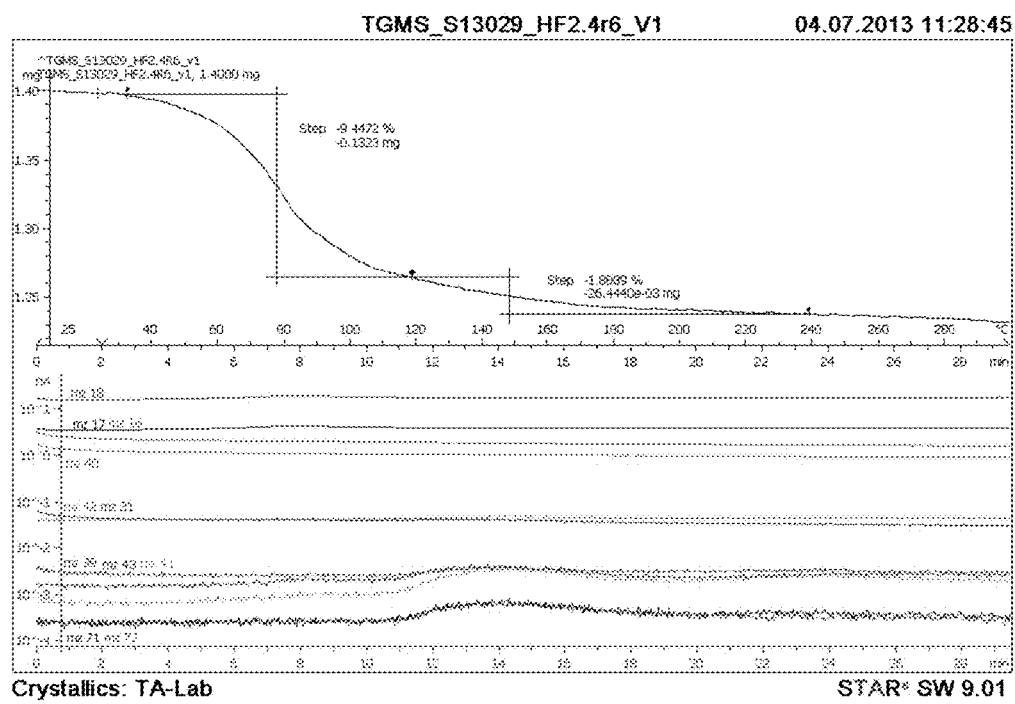
FIG. 25 depicts a thermogravimetric analysis coupled with mass spectroscopy of Form 5 of Compound 1.

In one embodiment, provided herein is a crystalline form of Compound 1 having a thermogravimetric (TGA) thermograph corresponding substantially to the representative TGA thermogram as depicted in FIG. 25. In certain embodiments, the crystalline form exhibits a TGA thermogram comprising a total mass loss of approximately 9.4% of the total mass of the sample between approximately 35° C. and approximately 240° C. when heated from approximately 25° C. to approximately 300° C. Thus, in certain embodiments, the crystalline form loses about 9.4% of its total mass when heated from about ambient temperature to about 300° C. In certain embodiments, the crystalline form contains 2 molar equivalents of solvent in the crystal lattice corresponding to approximately 2 moles of water per mole of Compound 1. The theoretical water content of a dihydrate of Compound 1 is 10.2% by weight, matching the TGA weight loss observed. In certain embodiments, the crystalline form is a dihydrated form of Compound 1.

Figure 24:
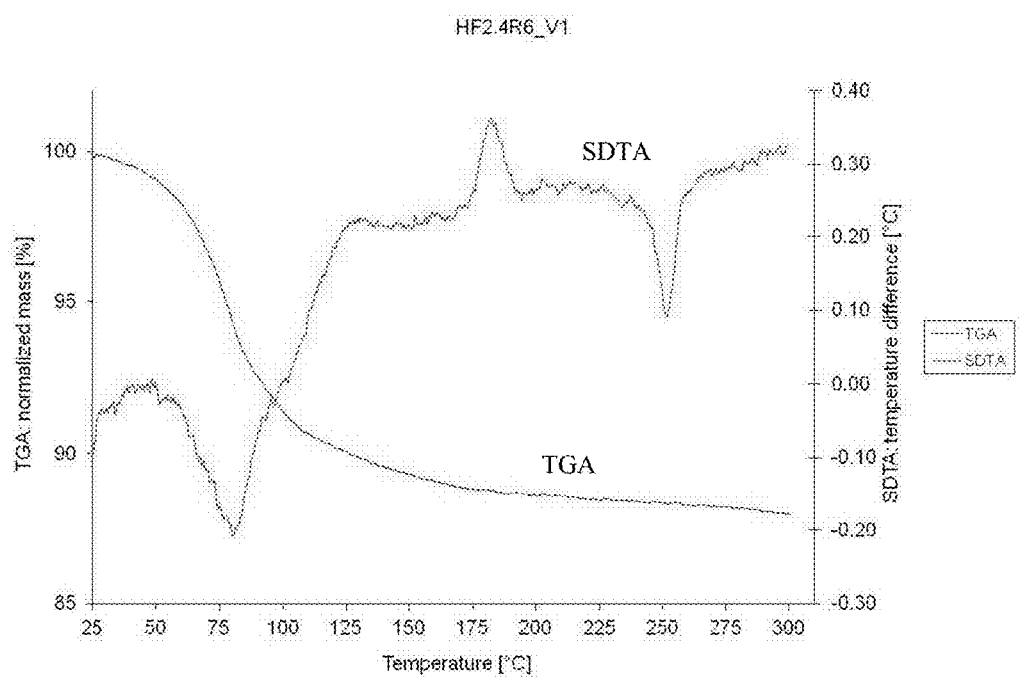
FIG. 24 depicts a thermogravimetrical analysis and single differential thermal analysis of Form 5 of Compound 1.

In one embodiment, provided herein is a crystalline form of Compound 1 having a SDTA thermogram as depicted in FIG. 24 comprising an endothermic event between about 50° C. and about 140° C. with a maximum at about 80° C. when heated from approximately 25° C. to approximately 300° C. (see Table 24).

In one embodiment, provided herein is a crystalline form of Compound 1 having a SDTA thermogram as depicted in FIG. 24 comprising an exothermic event between about 160° C. and about 200° C. with a maximum at about 181° C. when heated from approximately 25° C. to approximately 300° C. (see Table 24).

In one embodiment, provided herein is a crystalline form of Compound 1 having a SDTA thermogram as depicted in FIG. 24 comprising an endothermic event between about 225° C. and about 275° C. with a maximum at about 251° C. when heated from approximately 25° C. to approximately 300° C. (see Table 24).

In still another embodiment, Form 5 of Compound 1 is substantially pure. In certain embodiments, the substantially pure Form 5 of Compound 1 is substantially free of other solid forms, e.g., amorphous form. In certain embodiments, the purity of the substantially pure Form 5 of Compound 1 is no less than about 95% pure, no less than about 96% pure, no less than about 97% pure, no less than about 98% pure, no less than about 98.5% pure, no less than about 99% pure, no less than about 99.5% pure, or no less than about 99.8% pure.

5.3.6 Amorphous Compound 1

In certain embodiments, provided herein is amorphous Compound 1.

In certain embodiments, provided herein are methods for making amorphous Compound 1, comprising 1) equilibrating the temperature of a sample of one of the solid forms of Compound 1 provided herein at room temperature; 2) heating the sample to a first temperature at a first rate; 3) holding the sample isothermally for a period of time; 4) cooling the sample to a second temperature at a second rate; 5) heating the sample to a third temperature at about a third rate; and 6) collecting remaining solids. In one embodiment, the sample is Form 1 of Compound 1. In one embodiment, the first temperature is higher than the melting point of one of the solid forms of Compound 1 provided herein. In one embodiment, the second temperature is lower than room temperature. In another embodiment, the third temperature is higher than the glass transition temperature of the amorphous solid form of Compound 1 provided herein. In another embodiment, the first and third rates are about 10° C./min and the second rate is about 30° C./min, independently from each other. In one embodiment, the period of time at which the sample is held isothermally is about 5 minutes.

In certain embodiments, provided herein are methods for making amorphous Compound 1, comprising 1) equilibrating the temperature of a sample of Form 1 at about 25° C.; 2) heating the sample to about 275° C. at a rate of about 10° C./min; 3) holding the sample isothermally for about 5 minutes; 4) cooling the sample to about −10° C. at a rate of about 30° C./min; 5) heating the sample to about 150° C. at about 10° C. at a rate of about 10° C./min; and 6) collecting remaining solids.

In one embodiment, amorphous Compound 1 has a glass transition temperature (Tg) at about 120° C.

Figure 28:
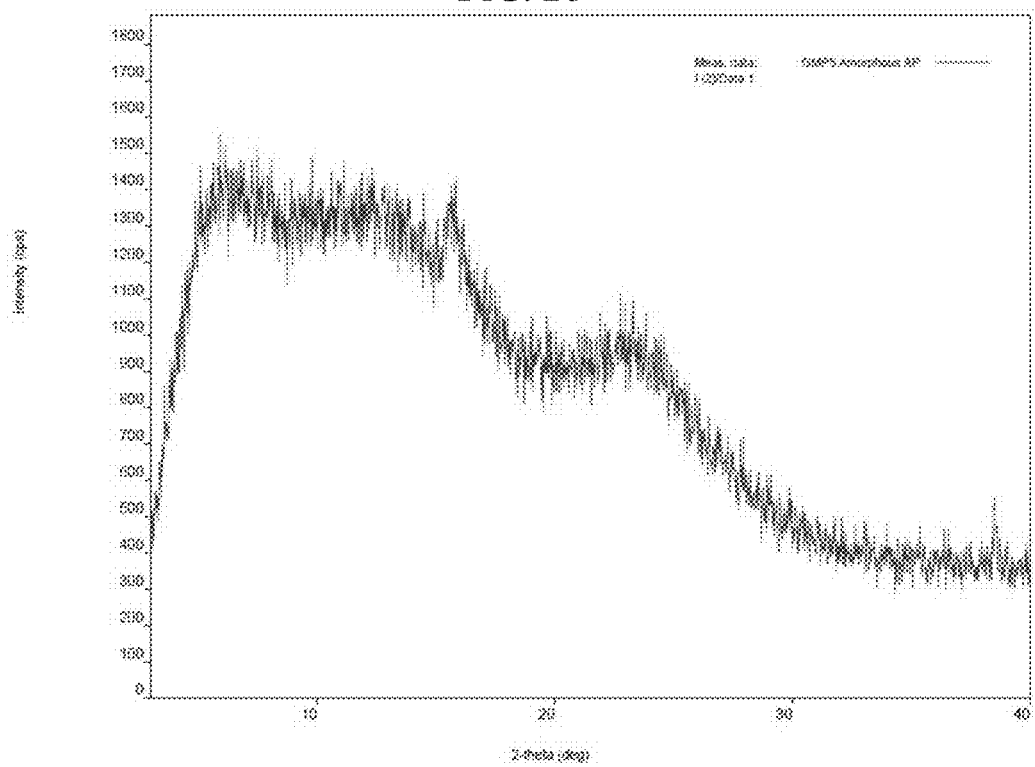
FIG. 28 depicts an X-ray powder diffractogram of amorphous Compound 1.
Figure 29:
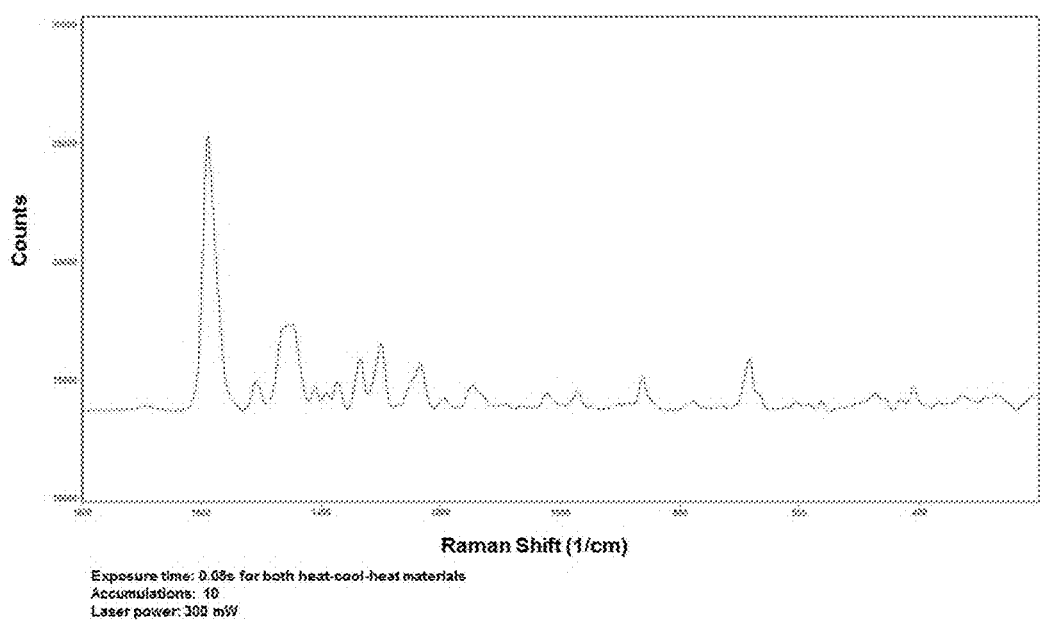
FIG. 29 depicts a Raman spectrum of amorphous Compound 1.

In one embodiment, amorphous Compound 1 has an X-ray powder diffraction pattern substantially as shown in FIG. 28.

Figure 32:
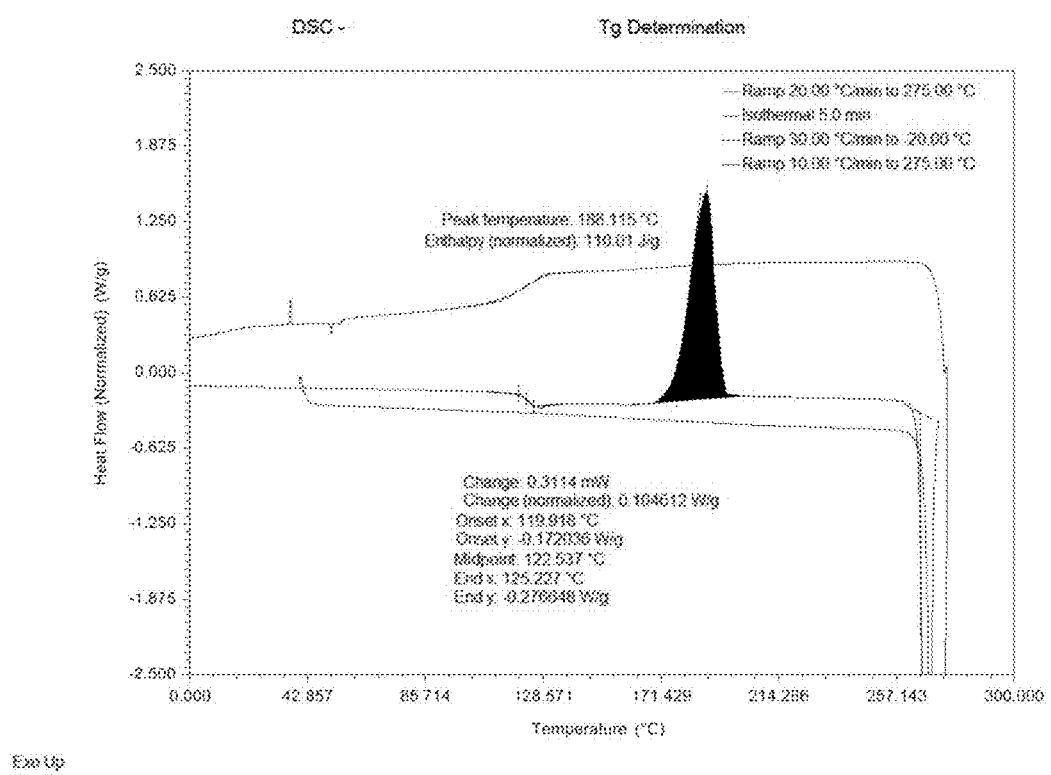
FIG. 32 depicts a differential scanning calorimetry thermogram of amorphous Compound 1 for determination of its glass transition temperature.

In one embodiment, provided herein is an amorphous solid form of Compound 1 having a DSC thermogram as depicted in FIG. 32 comprising an endothermic event between about 160° C. and about 200° C. with a maximum at about 188.1° C. when heated from approximately 25° C. to approximately 300° C. (see FIG. 32).

In still another embodiment, amorphous Compound 1 is substantially pure. In certain embodiments, the substantially pure amorphous Compound 1 is substantially free of other solid forms, e.g., Form 1, Form 2, Form 3, Form 4 or Form 5. In certain embodiments, the purity of the substantially pure amorphous Compound 1 is no less than about 95% pure, no less than about 96% pure, no less than about 97% pure, no less than about 98% pure, no less than about 98.5% pure, no less than about 99% pure, no less than about 99.5% pure, or no less than about 99.8% pure.

5.4 Methods of Use

The solid forms provided herein or combinations of the various solid forms provided herein can be used in the methods provided herein. The solid forms provided herein or combinations of the various solid forms provided herein can be used in the treatment of all diseases, disorders or conditions provided herein.

The solid forms provided herein are for use as a medicament.

Provided herein are methods for treating or preventing a cancer, comprising administering a solid form of Compound 1 provided herein or a pharmaceutical composition thereof to a patient having a cancer.

The solid forms provided herein are for use in a method for treating or preventing cancer, an inflammatory condition, an immunological condition, a neurodegenerative disease, diabetes, obesity, a neurological disorder, an age-related disease, a cardiovascular condition, or a conditions treatable or preventable by inhibition of a kinase pathway. The method comprises administering an effective amount of a crystal form to a subject in need thereof. In one embodiment, the kinase pathway is the TOR kinase pathway.

In some embodiments, the cancer is an advanced unrespectable solid tumor, or a hematologic malignancy. For example, the hematologic malignancy is CLL, NHL, or MM. In some such embodiments, the cancer has progressed on standard anti-cancer therapy, or the patient is not able to tolerate standard anti-cancer therapy. In yet others, the cancer is a cancer for which no approved therapy exists. In some embodiments, the cancer is resistant to standard therapy. In another, the patient has relapsed after standard therapy. In one embodiment, the cancer is a neoplasm metastasis.

In certain embodiments, the cancer is a blood borne tumor.

In certain embodiments, the cancer is a lymphoma, a leukemia or a multiple myeloma.

In certain embodiments, the cancer is non-Hodgkin's lymphoma. In certain embodiments, the non-Hodgkin's lymphoma is diffuse large B-cell lymphoma (DLBCL), follicular lymphoma (FL), acute myeloid leukemia (AML), mantle cell lymphoma (MCL), or ALK+ anaplastic large cell lymphoma. In one embodiment, the non-Hodgkin's lymphoma is advanced solid non-Hodgkin's lymphoma. In one embodiment, the non-Hodgkin's lymphoma is diffuse large B-cell lymphoma (DLBCL).

In certain embodiments, the cancer is a B-cell lymphoma.

In certain embodiments, the B-cell lymphoma is a B-cell non-Hodgkin's lymphoma selected from diffuse large B-cell lymphoma, Burkitt's lymphoma/leukemia, mantle cell lymphoma, mediastinal (thymic) large B-cell lymphoma, follicular lymphoma, marginal zone lymphoma (including extranodal marginal zone B-cell lymphoma and nodal marginal zone B-cell lymphoma), lymphoplamacytic lymphoma/Waldenstrom macroglobulinemia. In some embodiments, the B-cell lymphoma is chronic lymphocytic leukemia/small lymphocytic lymphoma (CLL/SLL). In one embodiment, the B-cell lymphoma is Waldenstrom macroglobulinemia.

In one embodiment, the B-cell non-Hodgkin's lymphoma is refractory B-cell non-Hodgkin's lymphoma. In one embodiment, the B-cell non-Hodgkin's lymphoma is relapsed B-cell non-Hodgkin's lymphoma.

In certain embodiments, the cancer is a T-cell lymphoma.

The B-cell disorders chronic lymphocytic leukemia/small lymphocytic lymphoma (CLL/SLL) represent 2 ends of a spectrum of the same disease process differing in the degree of blood/marrow involvement (CLL) versus lymph node involvement (SLL).

In another embodiment, the cancer is CLL characterized by deletion of chromosome 11q22, loss of ATM expression, mutation of IgVH, wild type IgVH, wild type p53/ATM, mutation of p53 or dysfunctional p53.

In other embodiments, the cancer is a multiple myeloma.

In certain embodiments, the cancer is a cancer of the head, neck, eye, mouth, throat, esophagus, bronchus, larynx, pharynx, chest, bone, lung, colon, rectum, stomach, prostate, urinary bladder, uterine, cervix, breast, ovaries, testicles or other reproductive organs, skin, thyroid, blood, lymph nodes, kidney, liver, pancreas, and brain or central nervous system.

In other embodiments, the cancer is a solid tumor. In certain embodiments, the solid tumor is a relapsed or refractory solid tumor.

In other embodiments, the solid tumor can be an advanced solid tumor.

In other embodiments, the solid tumor can be a neuroendocrine tumor, glioblastoma multiforme (GBM), hepatocellular carcinoma (HCC), breast cancer, colorectal cancer (CRC), salivary cancer, pancreatic cancer, adenocystic cancer, adrenal cancer, esophageal cancer, renal cancer, leiomyosarcoma, paraganglioma, head and neck squamous cell carcinoma, E-twenty six (ETS) overexpressing castration-resistant prostate cancer or E-twenty six (ETS) overexpressing Ewings sarcoma.

In one embodiment, the solid tumor is a neuroendocrine tumor. In certain embodiments, the neuroendocrine tumor is a neuroendocrine tumor of gut origin. In certain embodiments, the neuroendocrine tumor is of non-pancreatic origin. In certain embodiments, the neuroendocrine tumor is non-pancreatic of gut origin. In certain embodiments, the neuroendocrine tumor is of unknown primary origin. In certain embodiments, the neuroendocrine tumor is a symptomatic endocrine producing tumor or a nonfunctional tumor. In certain embodiments, the neuroendocrine tumor is locally unrespectable, metastatic moderate, well differentiated, low (grade 1) or intermediate (grade 2). In certain embodiments, the neuroendocrine tumor is of non-gut origin. In one embodiment, the neuroendocrine tumor of non-gut origin, is rapamycin resistant. In one embodiment, the neuroendocrine tumor of non-gut origin is a bronchial neuroendocrine tumor, or a neuroendocrine tumor with origin in an organ above the diaphragm, for example, a laryngeal neuroendocrine tumor, a pharyngeal neuroendocrine tumor, or a thyroid neuroendocrine tumor. In one embodiment, the neuroendocrine tumor of non-gut origin is a symptomatic endocrine producing tumor or a nonfunctional tumor. In one embodiment, the neuroendocrine tumor of non-gut origin is locally unrespectable, metastatic moderate, well differentiated, low (grade 1) or intermediate (grade 2).

In one embodiment, the solid tumor is non-small cell lung cancer (NSCLC).

In another embodiments the solid tumor is glioblastoma multiforme (GBM).

In another embodiment, the solid tumor is hepatocellular carcinoma (HCC).

In another embodiment, the solid tumor is breast cancer. In one embodiment, the breast cancer is hormone receptor positive. In one embodiment, the breast cancer is estrogen receptor positive (ER+, ER+/Her2 or ER+/Her2+). In one embodiment, the breast cancer is estrogen receptor negative (ER−/Her2+). In one embodiment, the breast cancer is triple negative (TN) (breast cancer that does not express the genes and/or protein corresponding to the estrogen receptor (ER), progesterone receptor (PR), and that does not overexpress the Her2/neu protein).

In one embodiment, the solid tumor is an advanced solid tumor.

In another embodiment, the cancer is head and neck squamous cell carcinoma.

In another embodiment, the cancer is E-twenty six (ETS) overexpressing castration-resistant prostate cancer.

In another embodiment, the cancer is E-twenty six (ETS) overexpressing Ewings sarcoma.

In another embodiment, the cancer is head and neck squamous cell carcinoma (HNSCC) characterized by deletion of chromosome 11q22 or loss of ataxia telangiectasia mutated (ATM) expression.

In another embodiment, the cancer is glioblastoma multiforme (GBM) characterized by 06-methylguanine-DNA methyltransferase (MGMT) methylation.

In other embodiments, the cancer is a cancer associated with the pathways involving mTOR, PI3K, or Akt kinases and mutants or isoforms thereof. Other cancers within the scope of the methods provided herein include those associated with the pathways of the following kinases: PI3Kα, PI3Kβ, P131δ, KDR, GSK3α, GSK3β, ATM, ATX, ATR, cFMS, and/or DNA-PK kinases and mutants or isoforms thereof. In some embodiments, the cancers associated with mTOR/PI3K/Akt pathways include solid and blood-borne tumors, for example, multiple myeloma, mantle cell lymphoma, diffused large B-cell lymphoma, acute myeloid lymphoma, follicular lymphoma, chronic lymphocytic leukemia; and solid tumors, for example, breast, lung, endometrial, ovarian, gastric, cervical, and prostate cancer; glioblastoma; renal carcinoma; hepatocellular carcinoma; colon carcinoma; neuroendocrine tumors; head and neck tumors; and sarcomas, such as Ewing's sarcoma.

In certain embodiments, provided herein are methods for achieving a Response Evaluation Criteria in Solid Tumors (for example, RECIST 1.1) of complete response, partial response or stable disease in a patient having a solid tumor, comprising administering a solid form of Compound 1 provided herein or a pharmaceutical composition thereof to said patient. In certain embodiments, provided herein are methods for achieving a National Cancer Institute-Sponsored Working Group on Chronic Lymphocytic Leukemia (NCI-WG CLL) of complete response, partial response or stable disease in a patient having leukemia, comprising administering a solid form of Compound 1 provided herein or a pharmaceutical composition thereof to said patient. In certain embodiments, provided herein are methods for achieving a Prostate Cancer Working Group 2 (PCWG2) Criteria of complete response, partial response or stable disease in a patient having prostate cancer, comprising administering a solid form of Compound 1 provided herein or a pharmaceutical composition thereof to said patient. In certain embodiments, provided herein are methods for achieving an International Workshop Criteria (IWC) for non-Hodgkin's lymphoma of complete response, partial response or stable disease in a patient having non-Hodgkin's lymphoma, comprising administering a solid form of Compound 1 provided herein or a pharmaceutical composition thereof to said patient. In certain embodiments, provided herein are methods for achieving an International Uniform Response Criteria (IURC) for multiple myeloma of complete response, partial response or stable disease in a patient having multiple myeloma, comprising administering a solid form of Compound 1 provided herein or a pharmaceutical composition thereof to said patient. In certain embodiments, provided herein are methods for achieving a Responses Assessment for Neuro-Oncology (RANO) Working Group for glioblastoma multiforme of complete response, partial response or stable disease in a patient having glioblastoma multiforme, comprising administering a solid form of Compound 1 provided herein or a pharmaceutical composition thereof to said patient.

In certain embodiments, the solid forms provided herein are for use in a method for achieving a Response Evaluation Criteria in Solid Tumors (RECIST 1.1) of complete response, partial response or stable disease in a subject. The methods comprise administering an effective amount of a solid form to a subject having a solid tumor.

In certain embodiments, the solid forms provided herein are for use in a method for improving International Workshop Criteria (IWC) for NHL, International Uniform Response Criteria for Multiple Myeloma (IURC), Eastern Cooperative Oncology Group Performance Status (ECOG) or Response Assessment for Neuro-Oncology (RANO) Working Group for GBM. The method comprises administering an effective amount of a solid form to a subject in need thereof.

In certain embodiments, provided herein are methods for increasing survival without disease progression of a patient having a cancer, comprising administering a solid form of Compound 1 provided herein or a pharmaceutical composition thereof to said patient.

In certain embodiments, provided herein are methods for treating a cancer, the methods comprising administering a solid form of Compound 1 provided herein or a pharmaceutical composition thereof to a patient having a cancer, wherein the treatment results in prevention or retarding of clinical progression, such as cancer-related cachexia or increased pain.

In some embodiments, provided herein are methods for treating a cancer, the methods comprising administering a solid form of Compound 1 provided herein or a pharmaceutical composition thereof to a patient having a cancer, wherein the treatment results in one or more of inhibition of disease progression, increased Time To Progression (TTP), increased Progression Free Survival (PFS), and/or increased Overall Survival (OS), among others.

5.5 Pharmaceutical Compositions

Solid forms of Compound 1 provided herein are useful for the preparation of pharmaceutical compositions, comprising an effective amount of a solid form of Compound 1 and a pharmaceutically acceptable carrier or vehicle. In some embodiments, the pharmaceutical compositions described herein are suitable for oral, parenteral, mucosal, transdermal or topical administration.

In one embodiment, the pharmaceutical compositions provided herein comprise a solid form of Compound 1 and one or more pharmaceutically acceptable excipients or carriers. In one embodiment, the pharmaceutical compositions provided herein comprise Form 1 of Compound 1 and one or more pharmaceutically acceptable excipients or carriers. In one embodiment, the pharmaceutical compositions provided herein comprise Form 2 of Compound 1 and one or more pharmaceutically acceptable excipients or carriers. In one embodiment, the pharmaceutical compositions provided herein comprise Form 3 of Compound 1 and one or more pharmaceutically acceptable excipients or carriers. In one embodiment, the pharmaceutical compositions provided herein comprise Form 4 of Compound 1 and one or more pharmaceutically acceptable excipients or carriers. In one embodiment, the pharmaceutical compositions provided herein comprise Form 5 of Compound 1 and one or more pharmaceutically acceptable excipients or carriers. In one embodiment, the pharmaceutical compositions provided herein comprise amorphous Compound 1 and one or more pharmaceutically acceptable excipients or carriers. In one embodiment, the pharmaceutical compositions provided herein comprise one or more of the following solid forms or solid form combinations: Form 1, Form 2, Form 3, Form 4, Form 5 and amorphous form of Compound 1 and one or more pharmaceutically acceptable excipients or carriers.

In one embodiment, the pharmaceutical compositions provided herein comprise tautomers of one or more solid forms of Compound 1 and one or more pharmaceutically acceptable excipients or carriers.

In one embodiment, the pharmaceutically acceptable excipients and carriers are selected from binders, diluents, disintegrants and lubricants. In another embodiment, the pharmaceutically acceptable excipients and carriers further include one or more antioxidants (e.g. EDTA or BHT).

In certain embodiments, the binders include, but are not limited to, cellulose (e.g., microcrystalline cellulose, such as AVICEL® PH 101, AVICEL® PH112, and AVICEL® PH 102) and starch (e.g., pregelatinized starch (STARCH 1500®)). In one embodiment, the binder is cellulose. In another embodiment, the binder is microcrystalline cellulose. In yet another embodiment, the binder is AVICEL® PH 101. In yet another embodiment, the binder is AVICEL® PH 102. In yet another embodiment, the binder is starch. In yet another embodiment, the binder is pregelatinized starch. In still another embodiment, the binder is STARCH 1500®.

In certain embodiments, the diluents include, but are not limited to, lactose (e.g., lactose monohydrate (FAST FLO® 316) and lactose anhydrous), cellulose (e.g., microcrystalline cellulose, such as AVICEL® PH 101 and AVICEL® PH 102), and mannitol. In one embodiment, the diluent is lactose. In another embodiment, the diluent is lactose monohydrate. In yet another embodiment, the diluent is FAST FLO® 316. In yet another embodiment, the diluent is lactose anhydrous. In yet another embodiment, the diluent is cellulose. In yet another embodiment, the diluent is microcrystalline cellulose. In yet another embodiment, the diluent is AVICEL® PH 101. In still another embodiment, the diluent is AVICEL® PH 102).

In certain embodiments, the disintegrants include, but are not limited to, starch (e.g., corn starch) and carboxymethyl cellulose (e.g., croscarmellose sodium, such as AC-DI-SOL®), and sodium starch glycolate. In one embodiment, the disintegrant is starch. In another embodiment, the disintegrant is corn starch. In yet another embodiment, the disintegrant is carboxymethyl cellulose. In yet another embodiment, the disintegrant is croscarmellose sodium. In still another embodiment, the disintegrant is AC-DI-SOL®.

In certain embodiments, the lubricants include, but are not limited to, starch (e.g., corn starch), magnesium stearate, and stearic acid. In one embodiment, the lubricant is starch. In another embodiment, the lubricant is corn starch. In yet another embodiment, the lubricant is magnesium stearate. In still another embodiment, the lubricant is stearic acid.

In another embodiment, the pharmaceutical compositions provided herein comprise a solid form of Compound 1 and one or more pharmaceutically acceptable excipients or carriers, each independently selected from carboxymethyl cellulose, cellulose, lactose, magnesium stearate, starch, and stearic acid.

In one embodiment, the pharmaceutical compositions provided herein comprise about 2.5-10% by weight of a solid form of Compound 1, about 70-90% by weight of diluent(s)/binder(s), about 1-5% by weight of disintegrant(s), and about 0.1-2% by weight of lubricant(s).

In another embodiment, the pharmaceutical compositions provided herein comprise about 10% by weight of a solid form of Compound 1, about 59.85% by weight of mannitol, about 25% by weight of microcrystalline cellulose, about 3% by weight of sodium starch glycolate, about 1% by weight of silicon dioxide, about 0.5% by weight of stearic acid, and about 0.65% by weight of magnesium stearate.

In another embodiment, the pharmaceutical compositions provided herein comprise about 10% by weight of a solid form of Compound 1, about 59.45% by weight of mannitol, about 25% by weight of microcrystalline cellulose, about 3% by weight of sodium starch glycolate, about 1% by weight of silicon dioxide, about 0.5% by weight of stearic acid, about 0.4% BHT, and about 0.65% by weight of magnesium stearate.

In another embodiment, the pharmaceutical compositions provided herein comprise about 10% by weight of a solid form of Compound 1, about 59.35% by weight of mannitol, about 25% by weight of microcrystalline cellulose, about 3% by weight of sodium starch glycolate, about 1% by weight of silicon dioxide, about 0.5% by weight of stearic acid, about 0.5% disodium EDTA, and about 0.65% by weight of magnesium stearate.

In another embodiment, the pharmaceutical compositions provided herein comprise about 10% by weight of a solid form of Compound 1, about 58.95% by weight of mannitol, about 25% by weight of microcrystalline cellulose, about 3% by weight of sodium starch glycolate, about 1% by weight of silicon dioxide, about 0.5% by weight of stearic acid, about 0.5% disodium EDTA, about 0.4% BHT, and about 0.65% by weight of magnesium stearate.

In certain embodiments, provided herein are pharmaceutical compositions comprising an opaque coating. Without being limited by theory, it was found that a more opaque coating protected the drug product from degradation. In some embodiments, the pharmaceutical composition is formulated as a tablet. In some such embodiments, the tablet is film coated. In some embodiments, the tablet is film coated to a weight gain of 1-8%. In others, the film coating is about 5% by weight of the tablet.

In certain embodiments, provided herein are pharmaceutical compositions, wherein the amounts of the recited components can independently be varied by 1%, 2%, 3%, 4%, 5%, 6%, 7%, 8%, 9%, 10%, 15%, 20% or 25%.

The pharmaceutical compositions provided herein can be provided in a unit-dosage form or multiple-dosage form. A unit-dosage form, as used herein, refers to physically discrete unit suitable for administration to a human and animal subject, and packaged individually as is known in the art. Each unit-dose contains a predetermined quantity of an active ingredient(s) sufficient to produce the desired therapeutic effect, in association with the required pharmaceutical carriers or excipients. Examples of a unit-dosage form include an individually packaged tablet or capsule. A unit-dosage form may be administered in fractions or multiples thereof. A multiple-dosage form is a plurality of identical unit-dosage forms packaged in a single container to be administered in segregated unit-dosage form.

In another embodiment, provided herein are unit dosage formulations that comprise between about 0.1 mg and about 2000 mg, about 1 mg and 200 mg, about 35 mg and about 1400 mg, about 125 mg and about 1000 mg, about 250 mg and about 1000 mg, or about 500 mg and about 1000 mg solid form of Compound 1, or a solid form thereof.

In a particular embodiment, provided herein are unit dosage formulation comprising about 0.1 mg, about 0.25 mg, about 0.5 mg, about 1 mg, about 2 mg, about 2.5 mg, about 5 mg, about 7.5 mg, about 8 mg, about 10 mg, about 15 mg, about 20 mg, about 25 mg, about 30 mg, about 35 mg, about 40 mg, about 45 mg, about 50 mg, about 60 mg, about 70 mg, about 75 mg, about 100 mg, about 125 mg, about 140 mg, about 150 mg, about 175 mg, about 200 mg, about 250 mg, about 280 mg, about 300 mg, about 350 mg, about 400 mg, about 500 mg, about 560 mg, about 600 mg, about 700 mg, about 750 mg, about 800 mg, about 1000 mg or about 1400 mg of a solid form of Compound 1. In a particular embodiment, provided herein are unit dosage formulations that comprise about 2.5 mg, about 5 mg, about 7.5 mg, about 8 mg, about 10 mg, about 15 mg, about 20 mg, about 25 mg, about 30 mg, about 40 mg, about 45 mg, about 50 mg, about 60 mg or about 100 mg of a solid form of Compound 1 or a tautomer thereof. In a particular embodiment, provided herein are unit dosage formulations that comprise about 1 mg, about 2 mg, about 5 mg, about 7.5 mg and about 10 mg.

In some embodiments, a unit dosage form comprising Compound 1, or a tautomer thereof can be administered once daily (QD), twice daily (BID), three times daily, four times daily or more often.

In certain embodiments, provided herein are methods for preparing a composition provided herein, comprising: (i) weighing out the desired amount of a solid form of Compound 1 (e.g., Form 1, Form 2, Form 3, Form 4, Form 5 or amorphous) and the desired amount of excipients (such as lactose monohydrate, croscarmellose sodium and/or microcrystalline cellulose); (ii) mixing or blending the solid form of Compound 1 and the excipients; (iii) passing the mixture of the solid form of Compound 1 and excipients through a screen (such as a 25 mesh screen); (iv) mixing or blending the solid form of Compound 1 and the excipients after passage through the screen; (v) weighing out the desired amount of lubricating agents (such as stearic acid and magnesium stearate); (vi) passing the lubricating agents through a screen (such as a 35 mesh screen); (vii) mixing or blending the solid form of Compound 1, the excipients and the lubricating agents; (viii) compressing the mixture of the solid form of Compound 1, the excipients and the lubricating agents (such as into a tablet form); and optionally (ix) coating the compressed mixture of the solid form of Compound 1 thereof, the excipients and the lubricating agents with a coating agent (such as Opadry pink, yellow or beige). In certain embodiments, the methods for preparing a composition provided herein are carried out in the dark, under yellow light or in the absence of UV light.

In certain embodiments, the pharmaceutical compositions provided herein comprise Form 1 of Compound 1, including substantially pure Form 1.

In certain embodiments, the pharmaceutical compositions provided herein comprise Form 2 of Compound 1, including substantially pure Form 2.

In certain embodiments, the pharmaceutical compositions provided herein comprise Form 3 of Compound 1, including substantially pure Form 3.

In certain embodiments, the pharmaceutical compositions provided herein comprise Form 4 of Compound 1, including substantially pure Form 4.

In certain embodiments, the pharmaceutical compositions provided herein comprise Form 5 of Compound 1, including substantially pure Form 5.

In certain embodiments, the pharmaceutical compositions provided herein comprise amorphous Compound 1, including substantially pure amorphous Compound 1.

6. EXAMPLES

The following Examples are presented by way of illustration, not limitation. The following abbreviations are used in descriptions and examples:

2MXETOH: 2-Methoxyethanol
AAC: Accelerated aging conditions (48 hours at 40° C. and 75% RH)
ACN: Acetonitril
Am: Amorphous
AmPhos: p-Dimethylamino phenylditbutylphosphine
API: Active Pharmaceutical Ingredient
AS: ID for anti-solvent crystallization experiment
Boc: tert-Butoxycarbonyl
dba: Dibenzylidene acetone
DCM: Dichloromethane
DIPEA: N,N-Diisopropylethylamine
DMF: N,N-Dimethylformide
DMSO: Dimethylsulfoxide
DSC: Differential Scanning calorimetry
ECP: ID for evaporative experiment
EDTA: Ethylenediamine tetraacetate
ESI: Electrospray ionization
EtOH: Ethanol
FTIR: Fourier Transform Infra Red Spectroscopy
GRP: Grinding experiment
HF: ID for hot-filtration crystallization experiment
HPLC: High performance liquid chromatography
IPA: 2-Propanol
LCMS: Liquid Chromatography with Mass Spectroscopy
MeOH: Methanol
mp: Melting point
MS: Mass spectrometry
Ms: Mesylate or methanesulfonyl
MTBE: tert-Butyl methyl ether
MTBE: methyl tert-butyl ether
NBS: N-Bromosuccinimide
NMP: N-Methyl-2-pyrrolidone
NMP: N-methylpyrrolidinone
NMR: Nuclear magnetic resonance
PSU: ID for cooling-evaporative crystallization experiment
QSA: ID for Phase 1 experiments
RH: Relative Humidity
RT: Room Temperature
S: Solvent
SDTA: Single Differential Thermal Analysis
SLP: ID for slurry experiment
SM: Starting material
TA: Thermal Analysis
TCP: ID for thermocycling and reflux experiment
Tf: triflate or trifluoromethanesulfonyl
TFA: Trifluoroacetic acid
TFE: 2,2,2-Trifluoroethanol
TGA: Thermogravimetric Analysis
TGA-MS/TG-MS: Thermogravimetric Analysis coupled with Mass Spectroscopy
THF: Tetrahydrofuran
TLC: Thin layer chromatography
VDL: ID for vapor diffusion into solutions experiment
VDS: ID for vapor diffusion onto solids experiment
XRPD: X-Ray Powder Diffraction 6.1 Solid Forms 6.1.1 Polymorph Screen A polymorph screen of Compound 1 was performed to investigate whether different solid forms could be generated under various conditions, such as different solvents, temperature and humidity changes.

The solvents used in the polymorph screen were either HPLC or reagent grade, including acetone, acetonitrile (ACN), n-butanol (n-BuOH), absolute ethanol (EtOH), ethanol/water (1:1), methanol (MeOH), 2-propanol (IPA), ethyl acetate (EtOAc), methylene chloride (DCM), methyl ethyl ketone (MEK), methyl t-butyl ether (MTBE), heptane, toluene, tetrahydrofuran (THF), dimethyl sulfoxide (DMSO), N-methylpyrrolidone (NMP), N,N-dimethylformamide (DMF) and water.

All of the solid samples generated in the polymorph screen were analyzed by XRPD. XRPD analysis was conducted on a Crystallics T2 high-throughput X-ray powder diffractometer using Cu Kα radiation at 1.54 Å. The instrument was equipped with a fine focus X-ray tube. The voltage and amperage of the X-ray generator were set at 45 kV and 40 mA, respectively. The divergence slits were set at 4 mm and 2 mm and the measuring slits were set at 0.5 mm and 0.2 mm. Diffracted radiation was measured using a Peltier-cooled Si (Li) solid-state detector. A theta-two theta continuous scan at 2.40°/minutes (0.5 sec/0.02° step) from 1.5° to 41.5° 2θ was used. A sintered alumina standard was used to check the peak positions.

DSC analyses were performed on a DSC822e instrument (Mettler-Toledo GmbH, Switzerland). Indium was used as the calibration standard. Approximately 2-5 mg of sample was placed into a DSC pan. The sample was heated under nitrogen at a rate of 10° C./min, up to a final temperature of 300° C. Melting points were reported as the extrapolated onset temperatures.

TGA analyses were performed on a TA instrument Q5000 Thermogravimetric Analyzer. Calcium oxalate was used for a performance check. Approximately 5-20 mg of accurately weighed sample was placed on a pan and loaded into the TGA furnace. The sample was heated under nitrogen at a rate of 10° C./min, up to a final temperature of 300° C.

TGA/SDTA analyses were performed on a TGA/SDTA851e instrument (Mettler-Toledo GmbH, Switzerland). The TGA/SDTA851e instrument was calibrated for temperature with indium and aluminium. Samples were weighed into 100 μl aluminium crucibles and sealed. The seals were pin-holed and the crucibles heated in the TGA from 25 to 300° C. at a heating rate of 10° C./min. Dry $N_2$ gas was used for purging.

Morphology analysis of the samples was carried out on an Olympus microscope. Small amounts of samples were dispersed in mineral oil on a glass slide with cover slips and viewed with 20× or 50× magnification.

Hygroscopicity was determined on a Surface Measurement Systems DVS. Typically a sample size of 2-10 mg was loaded into the DVS instrument sample pan and the sample was analyzed on a DVS automated sorption analyzer at room temperature. The relative humidity was increased from 0% to 90% RH at 10% RH step then 95% RH. The relative humidity was then decreased in a similar manner to accomplish a full adsorption/desorption cycle. For selected hydrated forms, the analysis started at 50% RH and increased to 90% RH at 10% RH step. The relative humidity was then decreased in a similar manner to 0% RH followed by increasing to 50% RH.

High Performance Liquid Chromatography (HPLC) was performed according to the conditions in Table 1 and gradient program in Table 2.

TABLE 1

High Performance Liquid Chromatography (HPLC) experiemental conditions

| Manufacturer | Agilent |
|---|---|
| HPLC | HP1200sl |
| UV-detector | HP DAD |
| MS-detector | HP1100 API-ES MSD VL-type |
| Column | Waters Sunfire C18 (100 × 4.6 mm; 3.5 μm) |
| Column Temperature | 35° C. |
| Mobile Phase A | 10 mM ammonium acetate |
| Mobile Phase B | Acetonitrile 100% |
| Flow Rate | 1.0 ml/min |
| Post time | 1 min |
| UV-Detector | DAD |
| Range | 200-400 nm |
| Wavelength | 254 nm |
| Slit width | 4 nm |
| Time | 0-20 min |
| MS-Detector | MSD |
| Scan | positive |
| Mass Range | 70-1000 amu |
| Fragmentator | 70 |
| Time | 0-12 min |
| Autosampler: | |
| Temperature | Not controlled |
| Injection mode | loop |
| Injection volume | 5 μL |
| Needle wash | 2/3; ACN/H$_2$O (v/v) |
| Dilution solvent | 0.1% TFA water/acetonitrile (v/v = 50/50) |

TABLE 2

High Performance Liquid Chromatography (HPLC) experiemental gradient program

| Time (mins) | % A | % B |
|---|---|---|
| 0 | 90 | 10 |
| 16 | 10 | 90 |
| 20 | 10 | 90 |
| 21 | 90 | 10 |

The compound integrity is expressed as a peak-area percentage, calculated from the area of each peak in the chromatogram, except the 'injection peak', and the total peak-area, as follows:

$$peak-area\ \% = \frac{peak-area}{total-area} * 100\%$$

The peak-area percentage of the compound of interest is employed as an indication of the purity of the component in the sample.

Crystal16® multiple-reactor system (Avantium Technologies) holds 16 (4×4) standard HPLC glass vials (11.5 mm diameter, flat bottomed, 1.8 mL volume). A unit consists of four independently heated aluminum reactor blocks encased in a robust bench top setup. These blocks are electrically heated and cooled by a combination of Peltier elements and a cryostat. In order to prevent condensation of water on the reactor blocks and electronics during runs at temperatures below 10° C., the Crystal16® system provides an inlet for a dry purge gas (typically nitrogen). Operating Parameters are provided in Table 3.

TABLE 3

Operating Parameters of Crystal16 ® multiple-reactor system

| Temperature range | −15° C. to 150° C. |
|---|---|
| Heating/cooling | Individually programmable per reactor block |
| Temperature profile | Unlimited heating/cooling/hold steps per run programmable |
| Temperature control accuracy | 0.1° C. |
| Heating/cooling ramps | Programmable between 0° C. and 20° C./min |
| Stirrer speed (magnetic stirrer bars) | Programmable from 0-1250 rpm |
| Turbidity measurement | Per individual reactor in transmission |

6.1.2 Experiments and Methods
6.1.2.1 Solubility Experiment:

In order to select the screening solvents and to determine the concentration range to be used in the screen, a quantitative solubility assessment was performed on the starting material, Form 1 of Compound 1. A set of 15 solvents was analyzed. For each solvent, a standard 1.8 ml screw cap vial was loaded with about 30 mg of the starting material, Form 1 of Compound 1, 400 μL of solvent and a magnetic stirring bar. The vials were then closed and equilibrated at 25° C. for 24 h while stirring. The resulting mixtures (slurries) were filtered (0.5 micron) and the isolated mother liquors diluted to two dilutions selected according to the calibration curve. Quantities of Compound 1 in the diluted solutions were determined via HPLC analysis. The calibration curve was obtained from two independently prepared stock solutions of Compound 1 in 0.1% TFA in Water/Acetonitrile (50:50).

Subsequent to the solubility determination, the wet solids were harvested and analyzed by XRPD. Moreover, the residual solvent was evaporated from each vial (slurry) under vacuum at ambient temperature. All of the resulting residues were analyzed by XRPD to check for new (crystalline) forms.

In addition to the solubility determination, 15 slurry experiments of Form 1 of Compound 1 were performed with at 50° C. for 24 hours in 15 solvents (same 15 solvents). Table 4 summarizes the experimental conditions. At the end of the slurry time, the solids were separated from the solutions by centrifugation, harvested wet and dried and analyzed by XRPD and digital imaging.

TABLE 4

Experimental conditions for 30 slurry conversion experiments, combined with solubility determination

| Solvent | Sample Mass (mg) | Solvent Volume (μL) | Dissolved | Temperature (° C.) |
|---|---|---|---|---|
| 1,2-Ethanediol | 32.9 | 400 | No | 25 |
| 1,4-Dioxane | 33.0 | 400 | No | 25 |
| Diethyl Ether | 33.5 | 400 | No | 25 |
| Chloroform | 31.1 | 400 | No | 25 |
| 2-Methoxyethanol | 29.3 | 400 | No | 25 |
| Cyclohexane | 30.3 | 400 | No | 25 |
| p-Xylene | 27.5 | 400 | No | 25 |
| Cumene | 29.7 | 400 | No | 25 |
| Isopropyl Acetate | 29.2 | 400 | No | 25 |
| Anisole | 30.8 | 400 | No | 25 |
| Ethyl formate | 32.7 | 400 | No | 25 |
| 1-Propanol | 29.8 | 400 | No | 25 |
| 1,2-Dimethoxyethane | 30.4 | 400 | No | 25 |
| 2-Butanone | 28.6 | 400 | No | 25 |
| Acetonitrile | 30.8 | 400 | No | 25 |
| 1,2-Ethanediol | 46.5 | 400 | No | 50 |
| 1,4-Dioxane | 48.4 | 400 | No | 50 |
| Diethyl Ether | 51.0 | 400 | No | 50 |

TABLE 4-continued

Experimental conditions for 30 slurry conversion experiments, combined with solubility determination

| Solvent | Sample Mass (mg) | Solvent Volume (µL) | Dissolved | Temperature (° C.) |
|---|---|---|---|---|
| Chloroform | 53.0 | 400 | No | 50 |
| 2-Methoxyethanol | 50.0 | 400 | No | 50 |
| cyclohexane | 51.9 | 400 | No | 50 |
| p-Xylene | 41.7 | 400 | No | 50 |
| Cumene | 47.4 | 400 | No | 50 |
| Isopropyl Acetate | 48.1 | 400 | No | 50 |
| Anisole | 51.3 | 400 | No | 50 |
| Ethyl formate | 50.7 | 400 | No | 50 |
| 1-Propanol | 48.2 | 400 | No | 50 |
| 1,2-Dimethoxyethane | 51.5 | 400 | No | 50 |
| 2-Butanone | 46.5 | 400 | No | 50 |
| Acetonitrile | 55.9 | 400 | No | 50 |

6.1.2.2 Feasibility Study

The experimental conditions of the feasibility study with Compound 1 are summarized in Table 5. The freeze drying experiments were performed in 1.8 ml vials. Approximately 20 mg of starting material were weight in a HPLC vial and dissolved in five different solvent mixtures. The starting material, Form 1, did not dissolve in THF/water (90/10 or 50/50) and ethanol/water (90/10); therefore these experimental samples were not freeze-dried. Form 1 dissolved in TFE and TFE/water (90/10). These two experimental samples were freeze-dried in liquid nitrogen, followed by placing the vials in a freeze-dryer for 24 hours. The obtained solid was then harvested and analyzed by XRPD and digital imaging.

Grinding experiments were performed in stainless steel grinding vials, containing 2 stainless steel grinding balls and a frequency of 30 Hz. Following the experiments, XRPD analysis was performed to assess the crystallinity of the materials.

TABLE 5

Conditions applied for the feasibility study on Form 1

| Sample Mass (mg) | Solvent | Solvent Volume (µL) | Solubility (mg/mL) | Dissolved | Comments |
|---|---|---|---|---|---|
| 24.8 | THF/water (90/10) | 1000 | <25 | No | Freeze drying |
| 24.2 | Ethanol/water (90/10) | 400 | <60 | No | Freeze drying |
| 25.1 | THF/Water (50/50) | 1000 | <25 | No | Freeze drying |
| 20.7 | TFE/water (90/10) | 1000 | 21 | Yes | Freeze drying |
| 21.9 | TFE | 1000 | 22 | Yes | Freeze drying |
| 20.0 | None | | | | Grinding 1 hour |
| 20.0 | None | | | | Grinding 2 hours |

6.1.2.3 Physical Stability Study at Room Temperature and Different RH

Physical stability studies over a prolonged period of time (e.g., 4 weeks) were conducted in desiccators at defined relative humidity (0%, 50%, 75% and 100%). At regular intervals (e.g., 3 days, 1 week, 2 weeks, 3 weeks and 4 weeks), the materials were analyzed by XRPD. To determine if the material absorb water molecules under different relative humidity levels, four more additional vials were placed in the desiccators to weight them back periodically and determine the change in mass (see Table 7 and Table 8). The materials used in desiccators to reach the defined relative humidity are presented in Table 6.

TABLE 6

Preparation of the different humidity ranges

| Relative Humidity at RT | Method |
|---|---|
| 0% | $P_2O_5$ (powder) |
| 50% | $MgNO_3$ (saturated solution) |
| 75% | NaCl (saturated solution) |
| 100% | Climate chamber with water vapors |

TABLE 7

Initial experimental conditions for the four vials used to determine the water uptake

| Relative Humidity | Empty vial weight (mg) | Empty vial weight + Starting material (mg) | Starting material weight (mg) |
|---|---|---|---|
| 0% | 2297.5 | 2318.2 | 20.7 |
| 50% | 2314.1 | 2334.5 | 20.4 |
| 75% | 2285.5 | 2306.3 | 20.8 |
| 100% | 2333.3 | 2354.2 | 20.9 |

TABLE 8

Experimental conditions for the 20 stability tests

| Relative humidity | Time | Starting material weight (mg) |
|---|---|---|
| 0% | 3 days | 5.7 |
| | 1 weeks | 4.5 |
| | 2 weeks | 6.2 |
| | 3 weeks | 4.8 |
| | 4 weeks | 6.2 |
| 50% | 3 days | 6.3 |
| | 1 weeks | 5.1 |
| | 2 weeks | 4.6 |
| | 3 weeks | 5.2 |
| | 4 weeks | 5.5 |
| 75% | 3 days | 4.6 |
| | 1 weeks | 4.4 |
| | 2 weeks | 5.4 |
| | 3 weeks | 5.1 |
| | 4 weeks | 5.2 |
| 100% | 3 days | 5.3 |
| | 1 weeks | 5.9 |
| | 2 weeks | 5.6 |
| | 3 weeks | 5.3 |
| | 4 weeks | 6.3 |

6.1.2.4 Experimental Methods of the Polymorph Screening:

The screening experiments for Compound 1 comprised 96 experiments at microliter (µL) scale and 125 experiments at milliliter (mL) scale. The following ten crystallization procedures were applied: cooling-evaporation, evaporative, cooling crystallization with hot filtration, crash crystallization with anti-solvent addition, slurry conversion, vapor diffusion into solutions, vapor diffusion onto solid, thermocycling, reflux and grinding.

Cooling-Evaporative Crystallization Experiments at µl Scale:

The 96 cooling-evaporative experiments at µL scale were performed in well plates, employing 12 different solvents and 12 mixtures of solvents in Table 9 and four temperature profiles in Table 9. About 4 mg solid dose of Compound 1 was in each well of the microliter well plate. Subsequently, 80 μL of the screening solvent was added into the well to reach a concentration of 50 mg/ml.

The plates, with each well individually sealed, were placed in a Crystal Breeder to undergo a temperature profile as described in Table 10. The plates were placed under vacuum after completion of the temperature profile. The solvents were evaporated for several days at 200 mbar or 5 mbar and analyzed by XRPD and digital imaging. Following, the solid samples were exposed to accelerated aging conditions (2 days at 40° C./75% RH) and re-analyzed by XRPD and digital imaging.

TABLE 10

Temperature profiles employed for the 96 cooling-evaporative experiments

| Temperature profile # | $T_{start}$ (° C.) | Heating rate (° C./min) | $T_{max}$ (° C.) | Hold time (min) | Cooling rate (° C./h) | $T_{end}$ (° C.) | Age time (h) |
|---|---|---|---|---|---|---|---|
| 1 | 20 | 10.0 | 60 | 60 | 1.0 | 5 | 48 |
| 2 | 20 | 10.0 | 60 | 60 | 20.0 | 5 | 3 |

TABLE 9

Experimental conditions for the 96 μl cooling-evaporation experiments

| Solvent | Temperature Conditions | | | |
|---|---|---|---|---|
| 1,2-Ethanediol | Temperature Profile #1 | Temperature Profile #2 | Temperature Profile #3 | Temperature Profile #4 |
| Anisole | Temperature Profile #1 | Temperature Profile #2 | Temperature Profile #3 | Temperature Profile #4 |
| 2-Methoxyethanol | Temperature Profile #1 | Temperature Profile #2 | Temperature Profile #3 | Temperature Profile #4 |
| Acetonitrile/Anisole (50/50) | Temperature Profile #1 | Temperature Profile #2 | Temperature Profile #3 | Temperature Profile #4 |
| 1,2-Dimethoxyethane/1-Pentanol (50/50) | Temperature Profile #1 | Temperature Profile #2 | Temperature Profile #3 | Temperature Profile #4 |
| Isobutanol | Temperature Profile #1 | Temperature Profile #2 | Temperature Profile #3 | Temperature Profile #4 |
| Isopropyl Acetate/2-Methoxyethanol (50/50) | Temperature Profile #1 | Temperature Profile #2 | Temperature Profile #3 | Temperature Profile #4 |
| Water | Temperature Profile #1 | Temperature Profile #2 | Temperature Profile #3 | Temperature Profile #4 |
| 1,4-Dioxane/Water (50/50) | Temperature Profile #1 | Temperature Profile #2 | Temperature Profile #3 | Temperature Profile #4 |
| 1,4-Dioxane | Temperature Profile #1 | Temperature Profile #2 | Temperature Profile #3 | Temperature Profile #4 |
| Water/Ethanol (50/50) | Temperature Profile #1 | Temperature Profile #2 | Temperature Profile #3 | Temperature Profile #4 |
| Isopropyl Acetate | Temperature Profile #1 | Temperature Profile #2 | Temperature Profile #3 | Temperature Profile #4 |
| Water/Methanol (50/50) | Temperature Profile #1 | Temperature Profile #2 | Temperature Profile #3 | Temperature Profile #4 |
| Acetonitrile | Temperature Profile #1 | Temperature Profile #2 | Temperature Profile #3 | Temperature Profile #4 |
| isopropanol/Tetrahydrofuran (50/50) | Temperature Profile #1 | Temperature Profile #2 | Temperature Profile #3 | Temperature Profile #4 |
| Methanol/Acetonitrile (50/50) | Temperature Profile #1 | Temperature Profile #2 | Temperature Profile #3 | Temperature Profile #4 |
| Tetrahydrofuran/Ethanol (50/50) | Temperature Profile #1 | Temperature Profile #2 | Temperature Profile #3 | Temperature Profile #4 |
| Tetrahydrofuran | Temperature Profile #1 | Temperature Profile #2 | Temperature Profile #3 | Temperature Profile #4 |
| Methanol | Temperature Profile #1 | Temperature Profile #2 | Temperature Profile #3 | Temperature Profile #4 |
| Tetrahydrofuran/Chloroform (50/50) | Temperature Profile #1 | Temperature Profile #2 | Temperature Profile #3 | Temperature Profile #4 |
| Methanol/Chloroform (50/50) | Temperature Profile #1 | Temperature Profile #2 | Temperature Profile #3 | Temperature Profile #4 |
| Chloroform | Temperature Profile #1 | Temperature Profile #2 | Temperature Profile #3 | Temperature Profile #4 |
| Acetonitrile/Dichloromethane (50/50) | Temperature Profile #1 | Temperature Profile #2 | Temperature Profile #3 | Temperature Profile #4 |
| Ethyl Formate | Temperature Profile #1 | Temperature Profile #2 | Temperature Profile #3 | Temperature Profile #4 |

TABLE 10-continued

Temperature profiles employed for the 96 cooling-evaporative experiments

| Temperature profile # | $T_{start}$ (° C.) | Heating rate (° C./min) | $T_{max}$ (° C.) | Hold time (min) | Cooling rate (° C./h) | $T_{end}$ (° C.) | Age time (h) |
|---|---|---|---|---|---|---|---|
| 3 | 20 | 10.0 | 60 | 60 | 1.0 | 20 | 48 |
| 4 | 20 | 10.0 | 60 | 60 | 20.0 | 20 | 3 |

6.1.2.5 Cooling Crystallization with Hot Filtration:

The crystallization method with hot filtration comprised 15 solvent mixtures. Supersaturated solutions were prepared by stirring slurries (see Table 12) at 60° C. for one hour and then filtering the slurries. All the solutions were then placed in a Crystal16® system to undergo a cooling profile and aged for 62 h (see Table 11). If solids precipitated after the temperature profile, they were harvested wet and dried and analyzed by XRPD and digital imaging. The experiments with no solid after the temperature profile were left to evaporate under vacuum. The obtained dry solid samples were analyzed by XRPD and digital imaging. All the solid samples were exposed to accelerated aging conditions (2 days at 40° C./75% RH) and re-analyzed by XRPD and digital imaging.

TABLE 11

Cooling profile employed for the hot filtration experiments

| $T_{initial}$ (° C.) | Hold (min) | Cooling rate (° C./h) | $T_{final}$ (° C.) | Hold (hrs) |
|---|---|---|---|---|
| 60 | 60 | 1 | 5 | 62 |

TABLE 12

Experimental conditions and results for the hot filtration experiments

| Exp. No. | Stock solvent description | Solvent volume (μL) | Starting material weight (mg) | Solid after Temperature profile |
|---|---|---|---|---|
| 1 | Acetonitrile/Ethyl Formate | 5000 | 30.0 | No |
| 2 | Tetrahydrofuran/Water | 2000 | 30.0 | Yes |
| 3 | Water/Methanol | 5000 | 30.0 | Yes |
| 4 | N,N-Dimethylformamide/Cumene | 3000 | 30.0 | No |
| 5 | Water/1,4-Dioxane | 3000 | 30.0 | Yes |
| 6 | Isopropanol/Acetone | 5000 | 30.0 | Yes |
| 7 | Ethanol/Water | 5000 | 30.0 | Yes |
| 8 | Ethanol/N-Methyl-2-pyrrolidone | 2000 | 30.0 | No |
| 9 | Tetrahydrofuran/1,2-Dimethoxyethane | 4000 | 28.0 | Yes |
| 10 | Dimethyl Sulfoxide/Water | 5000 | 30.0 | No |
| 11 | Isopropyl Acetate/Diethyl Ether | 5000 | 30.0 | No |
| 12 | 2-Methoxyethanol/Chloroform | 2000 | 32.0 | Yes |
| 13 | Tetrahydrofuran/Acetonitrile | 5000 | 30.0 | Yes |
| 14 | Anisole/Chloroform | 5000 | 30.0 | No |
| 15 | Butanone, 2-/N-Methyl-2-pyrrolidone | 2000 | 30.0 | No |

6.1.2.6 Anti-Solvent Crystallization:

For the crash-crystallization experiments with anti-solvent addition, 15 different crystallization conditions were applied, using the selected solvents and eleven different anti-solvents (see Table 14). Stock solutions were prepared in each solvent (see Table 13). These solutions were saturated with Form 1 of Compound 1 and equilibrated for 24 h before filtering. The stock solutions were then liquid dosed into the experimental vials, followed by the anti-solvent addition. The anti-solvent was added to each solvent vial with a solvent to anti-solvent ratio of 1:0.25. In the case of no precipitation occurred, this ratio was increased to 1:1 or 1:4 with a waiting time of 60 minutes between the additions. After the last addition the samples were left stirring at ambient temperature for 24 hours. The precipitated solids were isolated from the mother liquor and analyzed wet and dried by XRPD and digital imaging. The samples, in which no precipitation occurred, were placed under vacuum and the dried solids were analyzed by XPRD and digital imaging. All the solids were exposed to accelerated aging conditions (2 days at 40° C./75% RH) and re-analyzed by XRPD and digital imaging.

TABLE 13

Stock solution for the anti-solvent addition experiments

| Exp. No. | Solvent(s) | Starting material weight (mg) | Solvent volume (μL) | Solution concentration (mg/mL) |
|---|---|---|---|---|
| 1 | Tetrahydrofuran | 30 | 5000 | 6 |
| 2 | 2-Methoxyethanol | 30 | 5000 | 6 |
| 3 | Tetrahydrofuran | 30 | 5000 | 6 |
| 4 | N-Methyl-2-pyrrolidone | 60 | 500 | 120 |
| 5 | 1,4-Dioxane | 30 | 5000 | 6 |
| 6 | N,N-Dimethylformamide | 30 | 1000 | 30 |
| 7 | N-Methyl-2-pyrrolidone | 60 | 500 | 120 |
| 8 | 1,4-Dioxane | 30 | 5000 | 6 |
| 9 | N-Methyl-2-pyrrolidone | 30 | 500 | 60 |
| 10 | Tetrahydrofuran | 30 | 5000 | 6 |
| 11 | 2-Methoxyethanol | 30 | 5000 | 6 |
| 12 | N,N-Dimethylformamide | 30 | 1000 | 30 |
| 13 | Tetrahydrofuran | 30 | 5000 | 6 |
| 14 | Dimethyl Sulfoxide | 30 | 500 | 60 |
| 15 | Dimethyl Sulfoxide | 30 | 500 | 60 |

TABLE 14

Results and experimental conditions for the anti-solvent addition experiments

| Exp No. | Solvent | Solvent volume (μL) | Anti-solvent | Starting Material wt (mg) | A* | B* | C* | AS:S ratio |
|---|---|---|---|---|---|---|---|---|
| 1 | THF | 5000 | Heptane | 30.0 | Yes | — | — | 0.25 |
| 2 | 2MXETOH | 5000 | Cumene | 30.0 | No | No | No | 4 |
| 3 | THF | 5000 | Cyclohexane | 30.0 | No | Yes | — | 1 |
| 4 | N-Methyl-2-pyrrolidone | 500 | Ethyl formate | 60.0 | No | No | Yes | 4 |
| 5 | 1,4-Dioxane | 5000 | p-Xylene | 30.0 | No | No | Yes | 4 |
| 6 | DMF | 1000 | Isopropylether | 30.0 | No | Yes | — | 1 |
| 7 | NMP | 500 | Cyclohexane | 60.0 | No | Yes | — | 1 |
| 8 | 1,4-Dioxane | 5000 | Heptane | 30.0 | No | Yes | — | 1 |
| 9 | NMP | 500 | TBME | 30.0 | No | No | Yes | 4 |
| 10 | THF | 5000 | 2,2,4-Trimethylpentane | 30.0 | Yes | — | — | 0.25 |
| 11 | 2MXETOH | 5000 | Ethyl acetate | 30.0 | No | No | Yes | 4 |
| 12 | DMF | 1000 | Water | 30.0 | Yes | — | — | 0.25 |
| 13 | THF | 5000 | Water | 30.0 | No | No | No | 4 |
| 14 | DMSO | 500 | Water | 30.0 | Yes | — | — | 0.25 |
| 15 | DMSO | 500 | Toluene | 30.0 | No | No | Yes | 4 |

*A = whether or not any precipitation after addition to 0.25:1 (AS:S); B = whether or not any precipitation after addition to 1:1 (AS:S); C = whether or not any precipitation after addition to 4:1 (AS:S).

6.1.2.7 Slurry Conversion Experiment:

Experiments were carried out by adding about 30 mg of Form 1 of Compound 1 to 500 μL of a test solvent. The resulting mixture was agitated for at least 24 hours at 25° C. Upon reaching equilibrium, the saturated supernatant solution was removed. The solid resulting from the equilibration was filtered and air-dried before analysis.

A total of ten slurry experiments were performed with Form 1 of Compound 1 with ten solvents at ambient temperature for two weeks (see Table 15). After the slurry time, the solids were separated from the solutions by centrifugation, harvested wet and analyzed by XRPD and digital imaging. The solids were then exposed to accelerated aging conditions (2 days at 40° C./75% RH), followed by XRPD re-analysis.

TABLE 15

Experimental conditions of the slurry experiments

| Exp No. | Solvent | Solvent volume (μL) | Starting Material wt (mg) | Concentration (mg/mL) | Dissolved at initial temperature | Solids after two weeks |
|---|---|---|---|---|---|---|
| 1 | Water | 500 | 29.7 | 59.4 | No | Yes |
| 2 | Methanol/Water (50/50) | 500 | 30.0 | 60 | No | Yes |
| 3 | Ethanol/Water (50/50) | 500 | 30.0 | 60 | No | Yes |
| 4 | Acetonitrile | 500 | 30.4 | 60.8 | No | Yes |
| 5 | 1,2-Ethanediol | 500 | 30.5 | 61 | No | Yes |
| 6 | Isopropyl Acetate | 500 | 31.0 | 62 | No | Yes |
| 7 | p-Xylene | 500 | 30.3 | 60.6 | No | Yes |
| 8 | 2-Butanone | 500 | 29.8 | 59.6 | No | Yes |
| 9 | Cumene | 500 | 29.8 | 59.6 | No | Yes |
| 10 | Anisole | 500 | 30.1 | 60.2 | No | Yes |

6.1.2.8 Evaporative Experiments

The 15 evaporative experiments were done by dissolving Form 1 of Compound 1 in 15 different solvent mixtures in Table 16. The starting material, Form 1 of Compound 1 was added into solvent and if the starting material did not dissolve in the solvent completely, the mixtures were filtered and then the clear solutions were evaporated. The solvents were slowly evaporated under vacuum (200 mbar or 5 mbar) until dryness to yield solid. The solid was analyzed by XRPD and digital imaging. The solid was then exposed to accelerated aging conditions (2 days at 40° C./75% RH), followed by XRPD re-analysis and digital imaging.

TABLE 16

Experimental conditions of the evaporative experiments

| Exp No. | Starting Material wt (mg) | Solvent | Solvent volume (μL) | Concentration (mg/mL) | D* |
|---|---|---|---|---|---|
| 1 | 30.2 | Ethanol/Chloroform (50/50) | 5000 | 60.4 | Yes |
| 2 | 31.5 | 2,2,2-trifluoroethanol/Water (50/50) | 5000 | 63 | No |
| 3 | 29.8 | 1,4-Dioxane/Ethyl formate (50/50) | 5000 | 59.6 | No |
| 4 | 28.7 | Methanol/Acetonitrile (50/50) | 5000 | 57.4 | No |

TABLE 16-continued

Experimental conditions of the evaporative experiments

| Exp No. | Starting Material wt (mg) | Solvent | Solvent volume (µL) | Concentration (mg/mL) | D* |
|---|---|---|---|---|---|
| 5 | 26.5 | Acetonitrile/Chloroform (50/50) | 5000 | 53 | No |
| 6 | 30.1 | Water/Tetrahydrofuran (50/50) | 5000 | 60.2 | Yes |
| 7 | 31 | Isopropanol/2-Butanone (50/50) | 5000 | 62 | No |
| 8 | 29.5 | Methanol/1,4-Dioxane (50/50) | 5000 | 59 | Yes |
| 9 | 28.9 | 2-Methoxyethanol/Isopropyl Acetate (50/50) | 5000 | 57.8 | No |
| 10 | 30.4 | Ethanol/Water (50/50) | 5000 | 60.8 | No |
| 11 | 29.4 | Water/NMP (50/50) | 5000 | 58.8 | No |
| 12 | 29.8 | THF/TBME (50/50) | 5000 | 59.6 | No |
| 13 | 30.6 | 1,4-Dioxane/Water (50/50) | 5000 | 61.2 | No |
| 14 | 28.8 | 1,2-Ethanediol/THF (50/50) | 5000 | 57.6 | Yes |
| 15 | 30.1 | Acetone/isopropanol (50/50) | 5000 | 60.2 | No |

*D = whether or not all the starting material dissolved at initial temperature.

6.1.2.9 Vapor Diffusion into Solutions:

For the 15 vapor diffusion into solution experiments, saturated solutions of Form 1 of Compound 1 were exposed to solvent vapors at room temperature for two weeks. Stock solutions were prepared in each solvent. These solutions were saturated with Form 1 of Compound 1 and equilibrated for 24 h before filtering into a set of 8 ml vials. These vials were left open and placed in closed 40 ml vials containing 2 ml of anti-solvent (see Table 17). After two weeks, the samples were checked on solid formation. When solid was formed the solid samples were analyzed wet by XRPD and digital imaging. If no precipitation occurred, the samples were placed under vacuum and the resulted solid samples were analyzed by XRPD and digital imaging. Subsequently, all the solid samples were exposed to accelerated aging conditions (2 days at 40° C./75% RH), followed by XRPD re-analysis and digital imaging.

TABLE 17

Experimental conditions of the vapor diffusion into solution experiments

| Exp No. | Starting Material wt (mg) | Solvent | Solvent volume (µL) | Anti-solvent | S* |
|---|---|---|---|---|---|
| 1 | 29.8 | 2-Methoxyethanol | 5000 | Anisole | No |
| 2 | 30.5 | DMF | 1000 | Acetonitrile | Yes |
| 3 | 30.1 | Tetrahydrofuran | 5000 | Diethyl ether | Yes |
| 4 | 29.9 | Dimethyl Sulfoxide | 600 | Water | Yes |
| 5 | 29.6 | 1,4-Dioxane | 5000 | Cyclohexane | No |
| 6 | 29.9 | DMF | 1000 | n-Pentane | No |
| 7 | 29.7 | NMP | 600 | Ethanol | No |
| 8 | 29.8 | 2,2,2-trifluoroethanol | 1000 | Cyclohexane | No |
| 9 | 30.1 | NMP | 600 | Heptane | No |
| 10 | 29.6 | Dimethyl Sulfoxide | 500 | Isopropyl ether | No |
| 11 | 30.0 | 2-Methoxyethanol | 5000 | Acetone | No |
| 12 | 29.9 | Tetrahydrofuran | 5000 | Chloroform | No |
| 13 | 30.4 | Dimethyl Sulfoxide | 500 | Ethyl acetate | No |
| 14 | 30.5 | Tetrahydrofuran | 5000 | n-Pentane | Yes |
| 15 | 29.9 | 1,4-Dioxane | 5000 | Dichloromethane | No |

*S = whether or not there is any solid formed after two weeks.

6.1.2.10 Vapor Diffusion onto Solids

For the 15 vapor diffusion onto solids experiments, amorphous Compound 1 was prepared by grinding crystalline Compound 1 for two hours. The amorphous material was transferred into 1.8 ml vials, which were left open and placed in closed 40 ml vials containing 2 ml of solvent (see Table 18). The material was exposed to solvent vapors at room temperature for two weeks. After that time, the experiments were harvested and analyzed by XRPD and digital imaging. Following, all the solids were exposed to accelerated aging conditions (40° C. and 75% RH) for two days, followed by XRPD re-analysis and digital imaging.

TABLE 18

Experimental conditions of the vapor diffusion onto solids experiments

| Exp No. | Starting Material wt (mg) | Solvent | Solvent volume (µL) | S* |
|---|---|---|---|---|
| 1 | 30.3 | tert-Butyl methyl ether | 2000 | Yes |
| 2 | 30.2 | 1,2-Ethanediol | 2000 | Yes |
| 3 | 29.8 | Chloroform | 2000 | Yes |
| 4 | 30.3 | Methanol | 2000 | Yes |
| 5 | 30.0 | Ethyl Formate | 2000 | Yes |
| 6 | 29.8 | Cyclohexane | 2000 | Yes |
| 7 | 30.6 | Acetonitrile | 2000 | Yes |
| 8 | 30.3 | Heptane | 2000 | Yes |
| 9 | 29.7 | isopropyl ether | 2000 | Yes |
| 10 | 29.8 | Pentane, n- | 2000 | Yes |
| 11 | 30.3 | Toluene | 2000 | Yes |
| 12 | 29.7 | Isobutyl acetate | 2000 | Yes |
| 13 | 30.5 | 2-Ethoxyethanol | 2000 | Yes |
| 14 | 30.0 | Water | 2000 | Yes |
| 15 | 29.7 | Acetone | 2000 | Yes |

*S = whether or not there was any solid left after two weeks.

6.1.2.11 Thermocycling Experiments

A total of 15 slurries of Compound 1 in solvents were prepared at room temperature (see Table 19). The mixtures were placed in the Crystal Breeder to undergo the temperature profile as follows: a) heated with a heating rate of 5° C./h until reaching 40° C.; b) cooled with a cooling rate of 5° C./h until reaching 5° C.; c) held at 5° C. for 30 min; d) repeated the cycle 8 times; and e) being stirred at 300 rpm during the temperature profile.

After the completion of the cycling program, the solids were separated from the liquids and analyzed wet and dried by XRPD and digital imaging. All the solids were then exposed to accelerated aging conditions (2 days at 40° C./75% RH), followed by XRPD re-analysis and digital imaging.

TABLE 19

Experimental conditions of the thermocycling experiments

| Exp No. | Starting Material wt (mg) | Solvent | Solvent volume (μL) | Concentration (mg/mL) | Dissolved at initial temperature | S* |
|---|---|---|---|---|---|---|
| 1 | 29.7 | tert-Butyl methyl ether | 1000 | 29.7 | No | Yes |
| 2 | 30.8 | Chloroform | 1000 | 30.8 | No | Yes |
| 3 | 29.5 | Methanol | 1000 | 29.5 | No | Yes |
| 4 | 29.5 | 1,2-Dimethoxy-ethane | 1000 | 29.5 | No | Yes |
| 5 | 29.8 | p-Xylene | 1000 | 29.8 | No | Yes |
| 6 | 29.7 | Acetonitrile | 1000 | 29.7 | No | Yes |
| 7 | 30.0 | Water | 1000 | 30 | No | Yes |
| 8 | 29.7 | Acetone | 1000 | 29.7 | No | Yes |
| 9 | 30.0 | 1,4-Dioxane | 1000 | 30 | No | Yes |
| 10 | 30.1 | 1,2-Ethanediol | 1000 | 30.1 | No | Yes |
| 11 | 30.5 | Ethyl Formate | 1000 | 30.5 | No | Yes |
| 12 | 30.6 | 2-Butanone | 1000 | 30.6 | No | Yes |
| 13 | 30.0 | Isopropanol | 1000 | 30 | No | Yes |
| 14 | 30.3 | Tetrahydrofuran | 1000 | 30.3 | No | Yes |
| 15 | 30.1 | Cumene | 1000 | 30.1 | No | Yes |

*S = whether or not there was any solid left after the eight cycles.

6.1.2.12 Reflux Experiments

In the 15 reflux experiments (see Table 21), the starting material, Form 1 of Compound 1, was mixed with selected solvents in 1.8 mL vials to give slurries. The slurries were then kept at a constant temperature (slightly below the corresponding boiling point of the chosen solvent) for one week and afterwards at 5° C. for two days (see Table 20).

TABLE 20

Temperature profile ($T_{profile}$) applied to the reflux experiments

| Exp No. | $T_{start}$ (° C.) | Heating rate (° C./min) | $T_{max}$ (° C.) | Hold time (h) | Cooling rate (° C./h) | $T_{end}$ (° C.) | Age time (h) |
|---|---|---|---|---|---|---|---|
| 1 | 25 | 5 | 50 | 168 | 10 | 5 | 48 |
| 2 | 25 | 5 | 60 | 168 | 10 | 5 | 48 |
| 3 | 25 | 5 | 70 | 168 | 10 | 5 | 48 |
| 4 | 25 | 5 | 80 | 168 | 10 | 5 | 48 |

After the temperature profile the solids were analyzed wet by XRPD and digital imaging. Then all the solids were exposed to accelerated aging conditions (2 days at 40° C./75% RH), followed by XRPD re-analysis and digital imaging.

TABLE 21

Experimental conditions for the reflux experiments

| Exp No. | Starting Material wt (mg) | Solvent | Solvent volume (μL) | Concentration (mg/mL) | Dissolved at initial temperature | S* |
|---|---|---|---|---|---|---|
| 1 | 29.5 | Ethyl formate | 1000 | 29.5 | No | Yes |
| 2 | 29.7 | tert-Butyl methyl ether | 1000 | 29.7 | No | Yes |
| 3 | 30.1 | Acetone | 1000 | 30.1 | No | Yes |
| 4 | 30.0 | Methyl acetate | 1000 | 30 | No | Yes |
| 5 | 29.5 | Chloroform | 1000 | 29.5 | No | Yes |
| 6 | 30.1 | Methanol | 1000 | 30.1 | No | Yes |
| 7 | 29.8 | Tetrahydrofuran | 1000 | 29.8 | No | Yes |
| 8 | 30.1 | Isopropyl ether | 1000 | 30.1 | No | Yes |
| 9 | 29.8 | Ethyl acetate | 1000 | 29.8 | No | Yes |
| 10 | 31.3 | 2-Methyl tetrahydrofuran | 1000 | 31.3 | No | Yes |
| 11 | 29.5 | Ethanol | 1000 | 29.5 | No | Yes |
| 12 | 30.6 | 2-Butanone | 1000 | 30.6 | No | Yes |
| 13 | 29.5 | Cyclohexane | 1000 | 29.5 | No | Yes |
| 14 | 29.5 | Acetonitrile | 1000 | 29.5 | No | Yes |
| 15 | 29.5 | Isopropanol | 1000 | 29.5 | No | Yes |

*S = whether or not there was any solid left after $T_{profile}$ in Table 20.

6.1.2.13 Grinding Experiments

In ten grinding experiments (see Table 22), about 30 mg Form 1 of Compound 1 was ground in metal grinding vials charged with two metal grinding balls. Then 10 μl of solvent was added. The samples were ground for 1 hour with a frequency of 30 Hz.

The ground solids were harvested and analyzed by XRPD and digital imaging. Then the solids were exposed to accelerated aging conditions (40° C./75% RH) for two days, followed by XRPD re-analysis and digital imaging.

TABLE 22

Experimental conditions for the grinding experiments

| Exp No. | Starting Material wt (mg) | Solvent | Solvent volume (μL) | Concentration (mg/mL) |
|---|---|---|---|---|
| 1 | 29.9 | Ethanol | 10 | 2990 |
| 2 | 30.3 | 1,2-Ethanediol | 10 | 3030 |
| 3 | 30.7 | Acetonitrile | 10 | 3070 |
| 4 | 30.0 | Isobutanol | 10 | 3000 |
| 5 | 29.6 | Toluene | 10 | 2960 |
| 6 | 29.7 | Isopropyl Acetate | 10 | 2970 |
| 7 | 30.6 | Anisole | 10 | 3060 |
| 8 | 29.8 | Water | 10 | 2980 |
| 9 | 29.9 | Acetone | 10 | 2990 |
| 10 | 30.1 | Cumene | 10 | 3010 |

Provided herein are five crystalline forms identified by the polymer screen. Form 1 was found to be a stable anhydrous crystalline form that melts at approximated 268.9° C. Form 2, a 1,2-ethanediol mono-solvated form of Compound 1, was prepared at least when 1,2-ethanediol was used as solvent in a slurry conversion experiment. Form 3, a 2,2,2-trifluorotoluene hemi-solvated form of Compound 1, was prepared from at least one evaporative experiment in TFE/water (50:50). Form 4, a 0.8 molar equivalent DMSO solvated form of Compound 1, was prepared at least from anti-solvent crystallization by using DMSO as solvent and water as anti-solvent. Form 5, a dihydrated form of Compound 1, was prepared in hot-filtration experiments at least when water was used as part of the crystallization solvent. A summary of the experimental conditions which the new solid forms were produced is presented in Table 23. A summary of physical data of solid forms is presented in Table 24.

TABLE 23

Summary of experimental conditions of the solid forms

| Form | Crystallization Method | Solvent |
|---|---|---|
| 2 | Evaporative | 1,2-ethanediol |
|  | Slurry |  |
|  | Thermocycling |  |
| 3 | Evaporative | 2,2,2-trifluoroethanol |
|  | Hot-filtration | Isopropanol/acetone (50:5) |
|  | Vapor diffusion into liquids | 2,2,2-trifluoroethanol (s), cyclohexane (AS) |
|  | Vapor diffusion onto solids | Chloroform |
| 4 | Anti-solvent | DMSO (S), water (AS) |
|  | Anti-solvent | DMSO (S), toluene (AS) |
|  | Vapor diffusion into liquids | DMSO (S), water (AS) |
| 5 | Hot-filtration | THF/water (50:50) |
|  | Hot-filtration | Water/methanol (50:50) |
|  | Hot-filtration | Water/1,4-dioxane (50:50) |
|  | Hot-filtration | Ethanol/water (50:50) |
|  | Anti-solvent | THF (S), water (AS) |
|  | Evaporative | Water/THF (50:50) |

TABLE 24

Physical Characterization of Solid Forms of Compound 1

| Form | Form Nature | Endotherms (° C.) | Purity (% by HPLC) | Physical stability (existing forms after 48 h 40° C./75% RH) |
|---|---|---|---|---|
| 1 | Anhydrate | 268.9 | 99.9 | Stable |
| 2 | Solvate (15.5% of 1,2-ethanediol - 1 molecule of 1,2-ethanediol per molecule of API) | 95-176 (broad), 264 | 100 | Form 2 |
| 3 | Solvate (12.8% of TFE - 0.5 molecule of TFE per molecule of API) | 149 (broad), 254 | 91.7 | Form 3 |
| 4 | Solvate (16.4% of DMSO - 0.8 molecule of DMSO per molecule of API) | 139 (broad), 258 | 93.6 | Forms 1 + 4 |
| 5 | Hydrate (9.4% of water - 1.9 molecules of water per molecule of API) | 80 (broad), 181 (exo), 251 | 90.1 | Form 5 |

6.1.2.14 Form 1

The XRPD pattern, crystal habit, TGA, SDTA, TGA-MS, HPLC and MS of Form 1 of Compound 1 are shown in FIGS. 2-6.

FIG. 2 provides an XRPD pattern of Form 1 of Compound 1. A list of X-Ray Diffraction Peaks for Form 2 of Compound 1 is provided below in Table 25.

TABLE 25

X-Ray Diffraction Peaks for Form 1 of Compound 1

| Two-theta angle (°) | d Space (Å) | Relative Intensity (%) |
|---|---|---|
| 7.94 | 11.12 | 11.54 |
| 9.74 | 9.07 | 87.52 |
| 11.94 | 7.4 | 33.02 |
| 15.86 | 5.58 | 37.83 |
| 17.3 | 5.12 | 26.24 |
| 17.86 | 4.96 | 20.51 |
| 19.46 | 4.56 | 11.69 |
| 25.14 | 3.54 | 79.73 |
| 26.42 | 3.37 | 25.15 |
| 27.06 | 3.29 | 44.83 |
| 27.98 | 3.19 | 26.77 |
| 29.38 | 3.04 | 10.14 |

FIG. 3 is a digital image of Form 1 of Compound 1.

FIGS. 4 and 5 provide TGA/SDTA signal and TGA-MS data, respectively, of Form 1.

The TGA thermogram of Form 1 in FIG. 4 does not shows any significant mass loss when heated from 25° C. to 300° C. The SDTA data of Form 1 in FIG. 4 shows a melting event at 268.9° C., corresponding to the melting point of Form 1 of Compound 1.

The TGA thermogram of Form 1 in FIG. 5 comprises a total mass loss of approximately 0.44% of the total mass of the sample between approximately 30° C. and approximately 250° C. when heated from approximately 25° C. to approximately 300° C. Thus, Form 1 loses about 0.44% of its total mass when heated from about ambient temperature to about 300° C. These observations suggest that Form 1 is anhydrous crystalline material.

Figure 6:
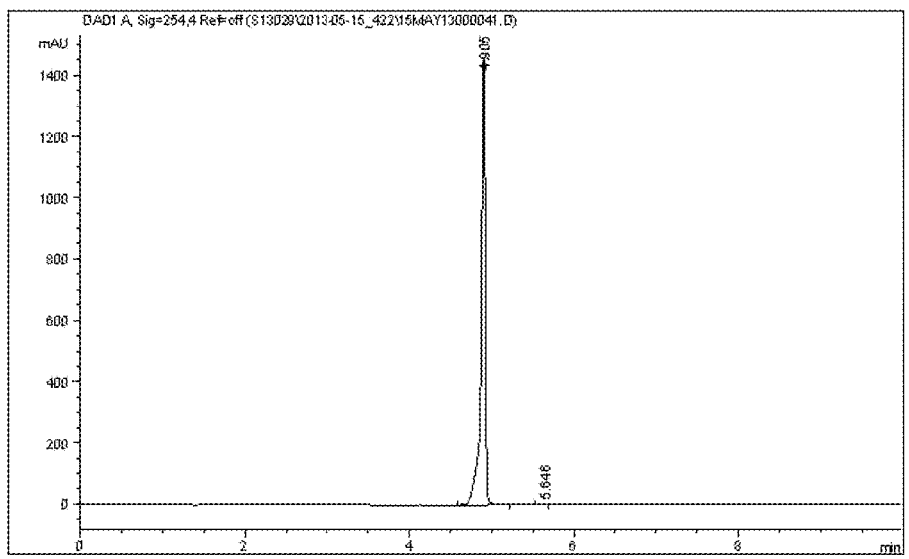
FIG. 6 depicts high performance liquid chromatography coupled with mass spectrometry of Form 1 of Compound 1.

FIG. 6 provides HPLC and MS data of Form 1. The peak retention time is 4.9 minutes and indicates the sample purity is 99.90% (area %).

6.1.2.15 Form 2

The XRPD pattern, crystal habit, TGA, SDTA, TGA-MS, HPLC and MS of Form 2 of Compound 1 are shown in FIGS. 7-11. Form 2 was prepared in slurry conversion experiments when 1,2-ethanediol was used as solvent. Form 2 appears stable under accelerated aging conditions (2 days at 40° C./75% RH).

FIG. 7 provides an overlay of XRPD patterns (from bottom to top) of: starting material (Form 1 of Compound 1), Form 2 as obtained from slurry conversion experiment in 1,2 ethanediol and Form 2 after exposure to accelerated aging conditions (AAC). A list of X-Ray Diffraction Peaks for Form 2 of Compound 1 is provided below in Table 26.

TABLE 26

X-Ray Diffraction Peaks for Form 2 of Compound 1

| Two-theta angle (°) | d Space (Å) | Relative Intensity (%) |
|---|---|---|
| 6.18 | 14.28 | 86.62 |
| 10.02 | 8.82 | 17.74 |
| 11.54 | 7.66 | 28.21 |
| 12.34 | 7.16 | 49.02 |
| 13.86 | 6.38 | 19.58 |
| 18.54 | 4.78 | 32.73 |
| 21.74 | 4.08 | 71.24 |
| 22.5 | 3.95 | 35.65 |
| 23.42 | 3.79 | 47.77 |
| 24.54 | 3.62 | 30.05 |
| 25.5 | 3.49 | 12.63 |
| 26.02 | 3.42 | 20.22 |
| 26.7 | 3.33 | 81.52 |
| 27.82 | 3.2 | 15.25 |
| 28.34 | 3.15 | 34.21 |
| 34.14 | 2.62 | 16.39 |

FIG. 8A is a digital image of Form 2 of Compound 1. FIG. 8B is a digital image of Form 2 of Compound 1 after exposure to accelerated aging conditions.

FIGS. 9 and 10 provide TGA/SDTA signal and TGA-MS data, respectively, of Form 2 as obtained from a slurry conversion experiment in 1,2-ethanediol.

The TGA thermogram of Form 2 in FIG. 9 shows a mass loss corresponding to a broad endothermic event observed in the SDTA signal between 95 and 176° C. with a maximum at about 137° C., which may be the desolvation of Form 2 of Compound 1. After the desolvation, the SDTA data of Form 2 in FIG. 9 shows a melting event at 264° C., corresponding to the melting point of Form 1 of Compound 1.

The TGA thermogram of Form 2 in FIG. 10 comprises a total mass loss of approximately 15.5% of the total mass of the sample between approximately 95° C. and approximately 175° C. when heated from approximately 25° C. to approximately 300° C. Thus, Form 2 loses about 15.5% of its total mass when heated from about ambient temperature to about 300° C. The thermal data indicates that Form 2 contains 1 molar equivalent of solvent in the crystal lattice corresponding to approximately 1 mole of 1,2-ethanediol per mole of Compound 1. The theoretical 1,2-ethanediol content of a 1,2-ethanediol mono-solvate of Compound 1 is 15.6% by weight, matching the TGA weight loss observed. These observations suggest that Form 2 is a 1,2-ethanediol mono-solvate of Compound 1.

FIG. 11 provides HPLC and MS data of Form 2 as obtained from the slurry conversion experiment in 1,2-ethanediol. The peak retention time is 4.8 minutes and indicates the sample purity is 100% (area %).

6.1.2.16 Form 3

The XRPD pattern, crystal habit, TGA, SDTA, TGA-MS, HPLC and MS of Form 3 of Compound 1 are shown in FIGS. 12-16. Form 3 was produced in a variety of crystallization solvents, including: 2,2,2-trifluoroethanol (TFE) combined with either water or cyclohexane, chloroform and the solvent mixture of isopropanol and acetone. Most of the Form 3 samples showed a yellowish color. The samples used for further analyses were prepared in the evaporative experiment in TFE/water (50:50).

FIG. 12 provides an overlay of XRPD patterns (from bottom to top) of: starting material (Form 1 of Compound 1), Form 3 as obtained from evaporative experiment in TFE/water (50:50) and Form 3 after exposure to accelerated aging conditions (AAC: 2 days at 40° C./75% RH). A list of X-Ray Diffraction Peaks for Form 3 of Compound 1 is provided below in Table 27.

TABLE 27

X-Ray Diffraction Peaks for Form 3 of Compound 1

| Two-theta angle (°) | d Space (Å) | Relative Intensity (%) |
| --- | --- | --- |
| 3.5 | 25.21 | 29.74 |
| 7.06 | 12.51 | 16.87 |
| 9.26 | 9.54 | 79.97 |
| 10.5 | 8.42 | 11.23 |
| 12.66 | 6.98 | 13.38 |
| 15.3 | 5.78 | 19.31 |
| 18.62 | 4.76 | 20.63 |

FIG. 13A is a digital image of Form 3 of Compound 1. FIG. 13B is a digital image of Form 3 of Compound 1 after exposure to accelerated aging conditions.

FIGS. 14 and 15 provide TGA/SDTA signal and TGA-MS data, respectively, of Form 3 as obtained from an evaporative experiment in TFE/water (50:50).

The TGA thermogram of Form 3 in FIG. 14 shows a mass loss corresponding to a broad endothermic event observed in the SDTA signal between 110° C. and 175° C. with a maximum at about 149° C., which may be the desolvation of Form 3. After the desolvation, the SDTA data of Form 3 in FIG. 14 shows a melting event at 254° C., corresponding to the melting point of the starting material, Form 1 of Compound 1. The temperature difference of the melting of the anhydrous Form 1 ($T_{peak}$ 264° C.) and after desolvation of Form 3 ($T_{peak}$ 254° C.) can be attributed to the partial degradation observed in the HPLC analysis. The chemical purity of Form 3 sample was determined by HPLC in FIG. 16 to be 91.8%.

The TGA thermogram of Form 3 in FIG. 15 comprises a total mass loss of approximately 12.8% of the total mass of the sample between approximately 40° C. and approximately 190° C. when heated from approximately 25° C. to approximately 300° C. Thus, Form 3 loses about 12.8% of its total mass when heated from about ambient temperature to about 300° C. The thermal data indicates that Form 3 contains 0.5 molar equivalents of solvent in the crystal lattice corresponding to approximately 0.5 mole of 2,2,2-trifluoroethanol per mole of Compound 1. The theoretical 2,2,2-trifluoroethanol content of a 2,2,2-trifluoroethanol hemi-solvate of Compound 1 is 11.5% by weight, matching the TGA weight loss observed. These observations suggest that Form 3 is a 2,2,2-trifluoroethanol hemi-solvate of Compound 1.

Figure 16:
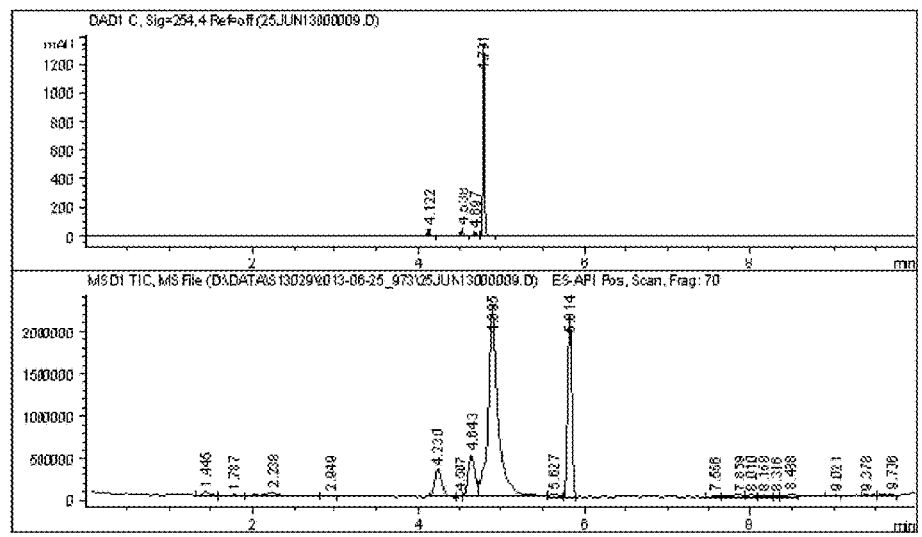
FIG. 16 depicts high performance liquid chromatography coupled with mass spectrometry of Form 3 of Compound 1.

FIG. 16 provides HPLC and MS data of Form 3 as obtained from an evaporative experiment in TFE/water (50:50). The peak retention time is 4.8 minutes with a sample purity of 91.8% (area %).

6.1.2.17 Form 4

The XRPD pattern, crystal habit, TGA, SDTA, TGA-MS, HPLC and MS of Form 4 of Compound 1 are shown in FIGS. 17-21. Form 4 was prepared by anti-solvent crystallization with DMSO as solvent and water as anti-solvent. Form 4 is physically unstable and converses to Form 1 or mixtures of Forms 1 and 4 upon exposure to accelerated aging conditions. Most likely after long term stability conditions, full conversion to Form 1 may occur.

FIG. 17 provides an overlay of XRPD patterns (from bottom to top) of: starting material, Form 1 of Compound 1; Form 4 as wet solid obtained from an anti-solvent experiment using DMSO as solvent and water as anti-solvent; Form 4 as dried solid obtained from an anti-solvent experiment using DMSO as solvent and water as anti-solvent; Amorphous Form of Compound 1 as wet solid from an anti-solvent experiment using DMSO as solvent and water as anti-solvent after exposure to accelerated aging conditions (AAC: 2 days at 40° C./75% RH); mixture of Forms 1 and 4 as dried solid obtained after exposure to accelerated aging conditions (AAC). A list of X-Ray Diffraction Peaks for Form 4 of Compound 1 is provided below in Table 28.

TABLE 28

X-Ray Diffraction Peaks for Form 4 of Compound 1

| Two-theta angle (°) | d Space (Å) | Relative Intensity (%) |
| --- | --- | --- |
| 8.22 | 10.74 | 12.38 |
| 10.14 | 8.71 | 28.85 |
| 10.66 | 8.29 | 42.92 |
| 14.02 | 6.31 | 19.57 |
| 18.1 | 4.9 | 25.78 |
| 20.62 | 4.3 | 24.43 |

TABLE 28-continued

X-Ray Diffraction Peaks for Form 4 of Compound 1

| Two-theta angle (°) | d Space (Å) | Relative Intensity (%) |
|---|---|---|
| 21.94 | 4.05 | 84.94 |
| 22.66 | 3.92 | 27.92 |
| 23.78 | 3.74 | 19.31 |
| 24.34 | 3.65 | 24.73 |
| 25.42 | 3.5 | 18.72 |
| 26.26 | 3.39 | 29.32 |

FIG. 18A is a digital image of Form 4 of Compound 1 as wet solid obtained from an anti-solvent experiment using DMSO as solvent and water as anti-solvent. FIG. 18B is a digital image of Form 4 of Compound 1 as dry solid obtained from an anti-solvent experiment using DMSO as solvent and water as anti-solvent.

FIGS. 19 and 20 provide TGA/SDTA signal and TGA-MS data, respectively, of Form 4 as obtained from an anti-solvent experiment using DMSO as solvent and water as anti-solvent.

The TGA thermogram of Form 4 in FIG. 19 shows a mass loss corresponding to a broad endothermic event observed in the SDTA signal between 100 and 175° C. with a maximum at about 140° C., which may be the desolvation of Form 4. After desolvation, the SDTA shows a melting event at 258° C., corresponding to the melting point of Form 1 of Compound 1. The temperature difference between the melting of the anhydrous Form 1 ($T_{peak}$ 264° C.) and the melting after desolvation of Form 4 ($T_{peak}$ 258° C.) can be attributed to the partial degradation observed in the HPLC analysis. The chemical purity of Form 4 sample was determined by HPLC in FIG. 21 to be 93.6%.

The TGA thermogram of Form 4 in FIG. 20 comprises a total mass loss of approximately 16.4% of the total mass of the sample between approximately 35° C. and approximately 180° C. when heated from approximately 25° C. to approximately 300° C. Thus, Form 4 loses about 16.4% of its total mass when heated from about ambient temperature to about 300° C. The thermal data indicate that Form 4 contains 0.8 molar equivalents of solvent in the crystal lattice corresponding to approximately 0.8 mole of dimethylsulfoxide per mole of Compound 1. The theoretical dimethylsulfoxide content of a 0.8 molar equivalent dimethylsulfoxide solvate of Compound 1 is 18.9% by weight, matching the TGA weight loss observed. These observations suggest that Form 4 is a dimethylsulfoxide solvate of Compound 1.

Figure 21:
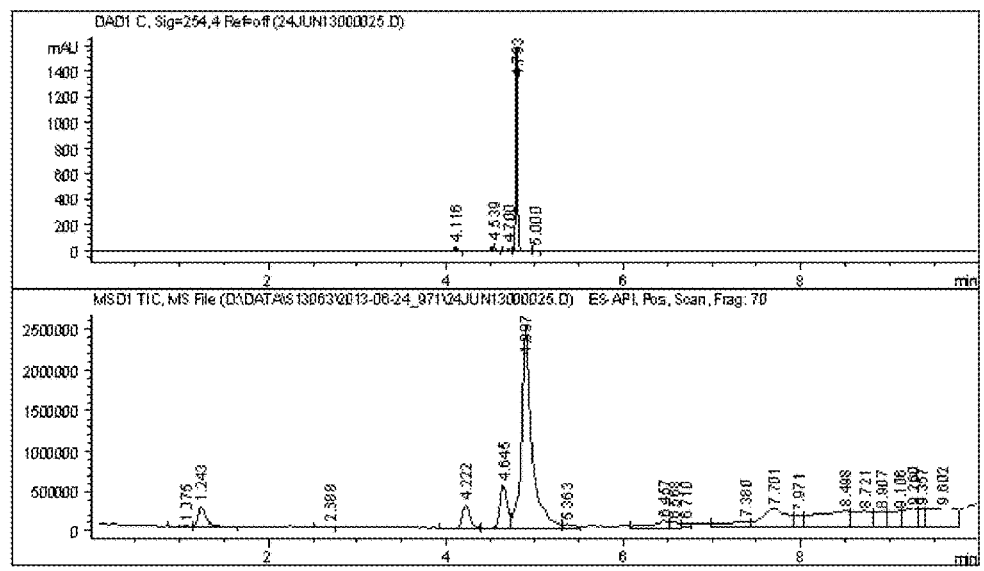
FIG. 21 depicts high performance liquid chromatography coupled with mass spectrometry of Form 4 of Compound 1.

FIG. 21 provides HPLC and MS data of Form 4 as obtained from an anti-solvent experiment using DMSO as solvent and water as anti-solvent. The peak retention time is 4.8 minutes with a sample purity of 93.6% (area %).

6.1.2.18 Form 5

The XRPD pattern, crystal habit, TGA, SDTA, TGA-MS, HPLC and MS of Form 5 of Compound 1 are shown in FIGS. 22-26. Form 5 was prepared in hot-filtration experiments in THF/water (50:50). Form 5 appears stable for at least two days under accelerated aging conditions.

FIG. 22 provides an overlay of XRPD patterns (from bottom to top) of: starting material, Form 1 of Compound 1; Form 5 of Compound 1; and Form 5 of Compound 1 after exposure to accelerated aging conditions (AAC: 2 days at 40° C./75% RH). A list of X-Ray Diffraction Peaks for Form 5 of Compound 1 is provided below in Table 29.

TABLE 29

X-Ray Diffraction Peaks for Form 5 of Compound 1

| Two-theta angle (°) | d Space (Å) | Relative Intensity (%) |
|---|---|---|
| 6.02 | 14.66 | 13 |
| 7.46 | 11.84 | 31.65 |
| 9.26 | 9.54 | 76.44 |
| 11.7 | 7.55 | 79.47 |
| 12.18 | 7.26 | 19.72 |
| 19.78 | 4.48 | 8.74 |
| 22.02 | 4.03 | 24.68 |
| 23.74 | 3.74 | 26.68 |
| 24.26 | 3.66 | 28.87 |
| 24.94 | 3.57 | 32.55 |
| 26.18 | 3.4 | 55.24 |
| 27.06 | 3.29 | 16.87 |
| 29.86 | 2.99 | 16.03 |

FIG. 23A is a digital image of Form 5 of Compound 1. FIG. 23B is a digital image of Form 5 of Compound 1 after exposure to accelerated aging conditions.

FIGS. 24 and 25 provide TGA/SDTA signal and TGA-MS data, respectively, of Form 5 obtained from a hot-filtration experiment in THF/water (50:50).

The TGA thermogram of Form 5 in FIG. 24 shows a mass loss corresponding to a broad endothermic event observed in the SDTA signal at $T_{peak}$ 80° C. which is likely related to the dehydration process, followed by re-crystallization at 181° C. and melting of Form 1 at 251° C. The large difference of the melting temperature of Form 1 here compared to that of the starting material Form 1 (264° C.) can be attributed to the different history of the two solids. Note that Form 5 was produced only when water was used in mixture with other solvents, e.g., THF, 1,4-dioxane, methanol and ethanol. The slurry experiment in water for two weeks at room temperature produced the anhydrous starting material, Form 1. This observation might be explained by the fact that Form 1 of Compound 1 is practically insoluble in water. Some dissolution of the starting material is needed to produce the dihydrated Form 5, which is provided by the organic solvent (THF, 1,4-dioxane, methanol or ethanol), followed by precipitation of Form 5. The chemical purity of Form 5 sample was determined by HPLC in FIG. 26 to be 90.1%.

The TGA thermogram of Form 5 in FIG. 25 comprises a total mass loss of approximately 9.4% of the total mass of the sample between approximately 35° C. and approximately 240° C. when heated from approximately 25° C. to approximately 300° C. Thus, Form 5 loses about 9.4% of its total mass when heated from about ambient temperature to about 300° C. The thermal data indicates that Form 5 contains 2 molar equivalents of solvent in the crystal lattice corresponding to approximately 2 moles of water per mole of Compound 1. The theoretical water content of a dihydrate of Compound 1 is 10.2% by weight, matching the TGA weight loss observed. These observations suggest that Form 5 is a dihydrated form of Compound 1.

Figure 26:
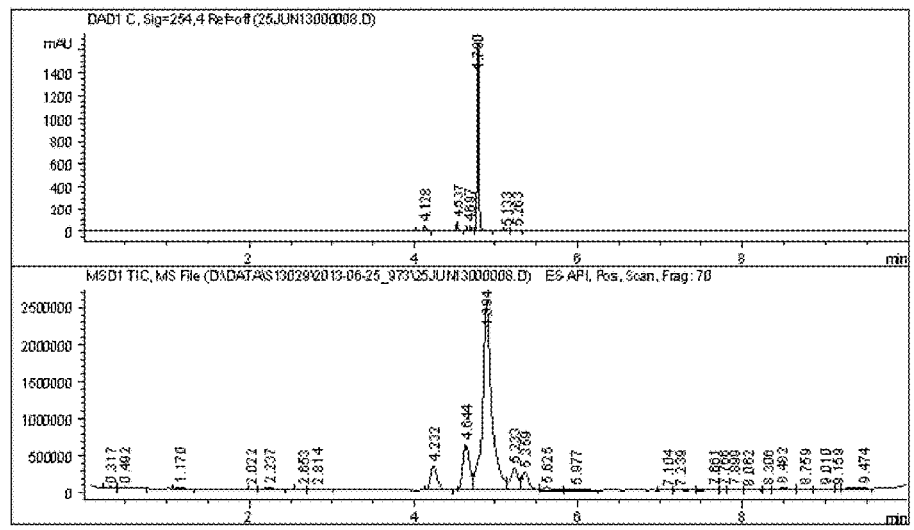
FIG. 26 depicts high performance liquid chromatography coupled with mass spectrometry of Form 5 of Compound 1.

FIG. 26 provides HPLC and MS data of Form 5 as solid obtained from a hot-filtration experiment in THF/water (50:50). The peak retention time is 4.8 minutes with a sample purity of 89.9% (area %).

6.1.2.19 Amorphous Form

The DSC, XRPD pattern, Raman spectrum, NMR, HPLC and MS of amorphous Compound 1 are shown in FIGS. 27-32.

Amorphous Compound 1 was prepared by 1) equilibrating the temperature of a sample of Form 1 at 25° C.; 2) heating up the sample to 275° C. at a rate of 10° C./min; 3)

holding the sample isothermally for 5 minutes; 4) cooling the sample to −10° C. at a rate of 30° C./min; 5) heating the sample to 150° C. at a rate of 10° C./min; and 6) collecting remaining solids.

Figure 27:
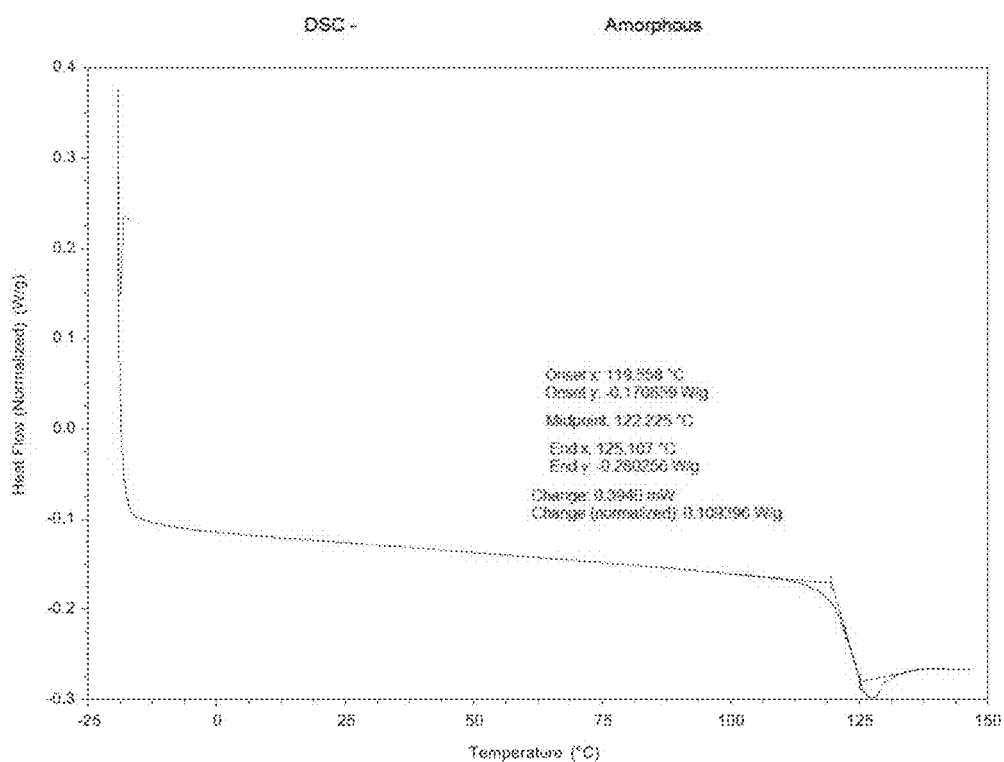
FIG. 27 depicts a differential scanning calorimetry thermogram of amorphous Compound 1.

The differential scanning calorimetry thermal analysis of amorphous Compound 1 in FIG. 27 shows that the glass transition temperature (Tg) of amorphous Compound 1 is at 120° C.

FIG. 28 provides an XRPD pattern of amorphous Compound 1.

Figure 30:
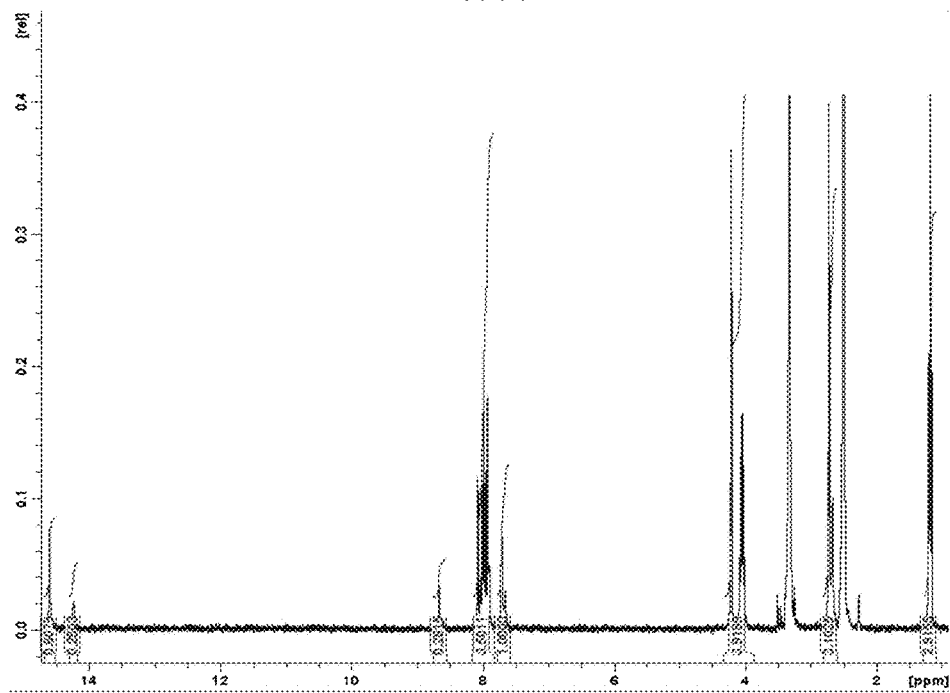
FIG. 30 depicts a proton nuclear magnetic resonance spectrum of amorphous Compound 1.

FIG. 30 provides a proton nuclear magnetic resonance spectrum of amorphous Compound 1.

Figure 31:
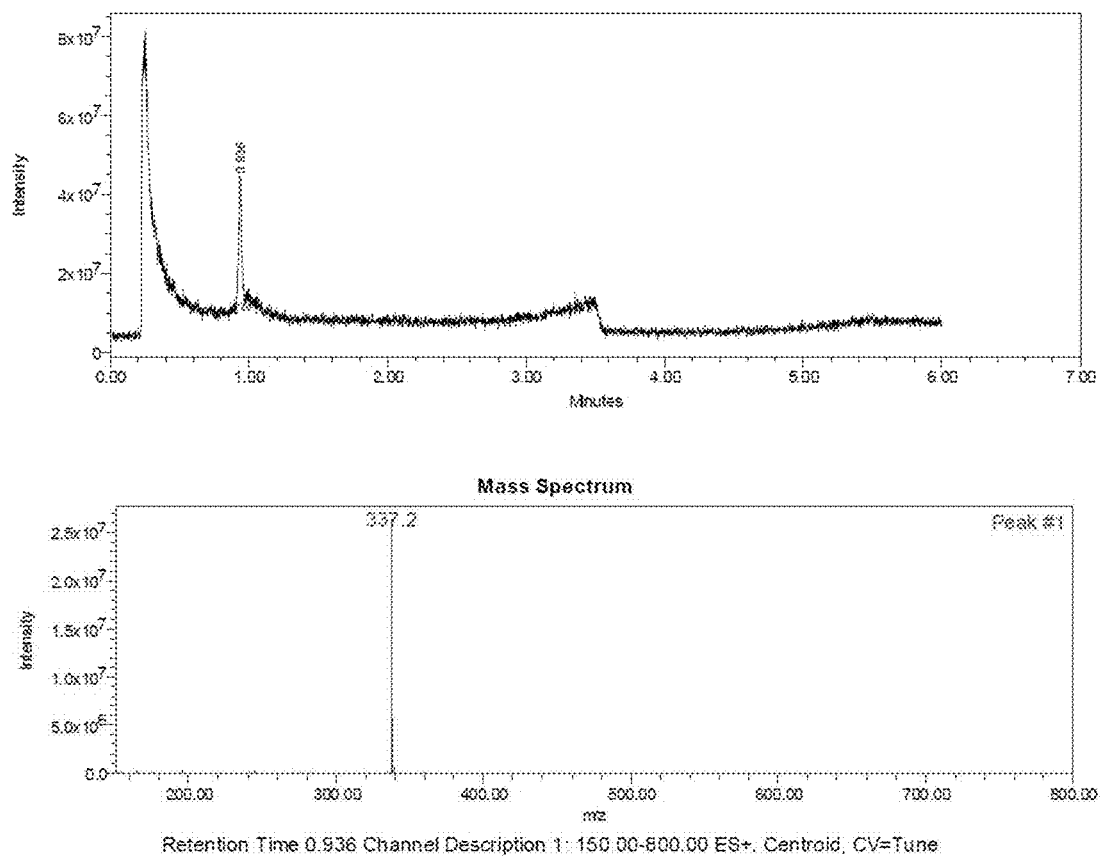
FIG. 31 depicts high performance liquid chromatography coupled with mass spectrometry of amorphous Compound 1.

FIG. 31 provides HPLC and MS data of amorphous Compound 1.

The DSC thermogram of amorphous Compound 1 in FIG. 32 shows a broad endothermic event between 160 and 200° C. with a maximum at about 188.1° C.

6.2 Biological Examples

6.2.1 Biochemical Assays

TOR HTR-FRET Assay. The following is an example of an assay that can be used to determine the TOR kinase inhibitory activity of solid forms of Compound 1. A solid form of Compound 1 is dissolved in DMSO and prepared as 10 mM stocks and diluted appropriately for the experiments. Reagents are prepared as follows:

"Simple TOR buffer" (used to dilute high glycerol TOR fraction): 10 mM Tris pH 7.4, 100 mM NaCl, 0.1% Tween-20, 1 mM DTT. Invitrogen recombinant TOR enzyme (cat# PV4753) is diluted in this buffer to an assay concentration of 0.200 μg/mL.

ATP/Substrate solution: 0.075 mM ATP, 12.5 mM $MnCl_2$, 50 mM Hepes, pH 7.4, 50 mM β-GOP, 250 nM Microcystin LR, 0.25 mM EDTA, 5 mM DTT, and 3.5 μg/mL GST-p70S6.

Detection reagent solution: 50 mM HEPES, pH 7.4, 0.01% Triton X-100, 0.01% BSA, 0.1 mM EDTA, 12.7 μg/mL Cy5-αGST Amersham (Cat#PA92002V), 9 ng/mL α-phospho p70S6 (Thr389) (Cell Signaling Mouse Monoclonal #9206L), 627 ng/mL α-mouse Lance Eu (Perkin Elmer Cat#AD0077).

To 20 μL of the Simple TOR buffer is added 0.5 μL of test solid form in DMSO. To initiate the reaction 5 μL of ATP/Substrate solution is added to 20 μL of the Simple TOR buffer solution (control) and to the compound solution prepared above. The assay is stopped after 60 minutes by adding 5 μL of a 60 mM EDTA solution; 10 μL of detection reagent solution is then added and the mixture is allowed to sit for at least 2 hours before reading on a Perkin-Elmer Envision Microplate Reader set to detect LANCE Eu TR-FRET (excitation at 320 nm and emission at 495/520 nm).

DNA-PK Assay.

DNA-PK assay is performed using the procedures supplied in the Promega DNA-PK assay kit (catalog # V7870). DNA-PK enzyme can be purchased from Promega (Promega cat#V5811).

6.3 Formulation Examples

Certain formulations comprising solid forms of Compound 1 are prepared and tested for a number of physical and chemical properties. Modifications are made and subsequent formulations are also tested, until formulations possessing desirable physical and chemical properties are found. The following example describes these formulations and their testing.

Study 1:

A $2^{3-1}$ study evaluates the effect of diluents, disintegrant and drug loading on tablet physical properties and chemical stability. Examples of formulation compositions are shown in Table 30. Initial tablet development is carried out in normal room UV light.

TABLE 30

Exemplary Formulation Composition Of Various Tablet Formulations

| Solid Form of Compound 1 (mg) | 0.5 | 0.5 | 5 | 5 |
|---|---|---|---|---|
| Microcrystalline Cellulose (mg) | 63.75 | 83.75 | 59.25 | 79.25 |
| Partially pregelatinized corn starch (mg) | | 10 | | 10 |
| Lactose monohydrate, spray dried (mg) | 30 | | 30 | |
| Crospovidone (mg) | | 4 | 4 | |
| Croscarmellose Na (mg) | 4 | | | 4 |
| Silicon dioxide (mg) | 1 | 1 | 1 | 1 |
| Magnesium Stearate (mg) | 0.75 | 0.75 | 0.75 | 0.75 |
| total uncoated tablet (mg) | 100 | 100 | 100 | 100 |
| Opadry II coating (mg) | 4 | 4 | 4 | 4 |
| total coated tablet (mg) | 104 | 104 | 104 | 104 |

Study 2:

A study is conducted to evaluate the effect of antioxidant (e.g., butylated hydroxyl toluene, BHT) and chelating agent (e.g., disodium edentate, $Na_2$-EDTA) on the stability of solid forms of Compound 1 in formulated product. The impact of dosage form (tablet vs capsule) on the stability of solid forms of Compound 1 is evaluated.

Examples of formulation compositions are shown in Table 31. All of the processes are carried out in dark.

TABLE 31

Exemplary Formulation Composition

| | % w/w | | | | | |
|---|---|---|---|---|---|---|
| Ingredients | Capsule | Capsule | Capsule | Capsule | Tablet | Capsule |
| Solid Form of Compound 1 | 0.5 | 0.5 | 0.5 | 0.5 | 0.5 | 0.5 |
| Mannitol (Mannogem EZ) | 84 | 94.1 | — | 93.6 | 83.6 | — |
| MCC PH112 | 10 | — | 94.1 | — | 10 | — |
| Lactose | — | — | — | — | — | 93.6 |
| Sodium starch glycolate | 3 | 3 | 3 | 3 | 3 | 3 |
| stearic acid | 1 | 1 | 1 | 1 | 1 | 1 |
| Butylated hydroxy toluene | | 0.4 | 0.4 | 0.4 | 0.4 | 0.4 |
| $Na_2$- EDTA | 0.5 | — | — | 0.5 | 0.5 | 0.5 |
| Mg stearate | 1 | 1 | 1 | 1 | 1 | 1 |
| Total | 100 | 100 | 100 | 100 | 100 | 100 |

Study 3:

Further study can be conducted to study the influence of coating and desiccant on the stability of Compound 1 tablets. All processes can be carried out under yellow light to prevent any UV light exposure to the Compound 1 formulations.

An exemplary formulation composition is provided in Table 32.

TABLE 32

Exemplary Formulation Composition Of Tablet

| Ingredients | % w/w |
|---|---|
| Solid form of Compound 1 | 0.5 |
| Mannitol (Mannogem EZ) | 83.6 |
| MCC PH112 | 10 |
| Sodium starch glycolate | 3 |
| stearic acid | 1 |
| Butylated hydroxy toluene | 0.4 |
| Na₂-EDTA | 0.5 |
| Mg stearate | 1 |
| Total | 100 |

TABLE 33

Exemplary Tablet Formulations

| Ingredients | % w/w (mg) Batch # 1 | 2 | 3 | 4 |
|---|---|---|---|---|
| Solid form of Compound 1 (active ingredient) | 10 | 10 | 10 | 10 |
| Mannitol (Mannogem EZ) | qs | qs | qs | qs |
| Microcrystalline Cellulose (PH 112) | 25 | 25 | 25 | 25 |
| Sodium Starch Glycolate | 3 | 3 | 3 | 3 |
| Silicon dioxide | 1 | 1 | 1 | 1 |
| Stearic acid | 0.5 | 0.5 | 0.5 | 0.5 |
| Disodium EDTA | | | 0.5 | 0.5 |
| BHT | | 0.4 | | 0.4 |
| Magnesium Stearate | 0.65 | 0.65 | 0.65 | 0.65 |
| Total | 100 | 100 | 100 | 100 |
| Color | Yellow | Yellow | Yellow | Yellow |

Preparation of Tablets:

The blends according to Table 34 to Table 39 are prepared as follows. Microcrystalline cellulose is weighed and added to an amber colored straight sided glass jar. The lid is closed and the jar is shook in order to coat the inside of the jar. Active ingredient (solid form of Compound 1) is added and blended for 10 minutes at 46 rpm using a Turbula mixer. The blend is passed through a 25 mesh screen and blended again for 10 minutes at 46 rpm using a Turbula mixer. The resulting blend is passed through a 35 mesh screen. Remaining excipients are added, except for lubricant (magnesium stearate). The resulting mixture is blended for 10 minutes at 46 rpm using a Turbula mixer. 6 grams of the resulting blend is added an amber glass jar. Lubricant is added and blended for 1 minute and 35 seconds at 46 rpm using a Turbula mixer. For low strength tablet formulations, 140 mg tablets are prepared using a 7.14 mm punch and die. For high strength tablet formulations, 400 mg tablets are prepared using a 10.3 mm punch and die.

TABLE 34

Exemplary Low Strength Tablet Formulation #1

| Ingredient | Source | Amount (weight %) |
|---|---|---|
| Solid form of Compound 1 | | 0.7 |
| microcrystalline cellulose | FMC Biopolymer | 38.1 |
| Mannitol | Roquette | 57.2 |
| sodium carboxymethylcellulose | FMC Biopolymer | 3.0 |
| magnesium stearate | Nitika Chemicals | 1.0 |

TABLE 35

Exemplary Low Strength Tablet Formulation #2

| Ingredient | Source | Amount (weight %) |
|---|---|---|
| Solid form of Compound 1 | | 0.7 |
| microcrystalline cellulose | FMC Biopolymer | 75.3 |
| pregelatinized starch | Colorcon | 20.0 |
| sodium carboxymethylcellulose | FMC Biopolymer | 3.0 |
| magnesium stearate | Nitika Chemicals | 1.0 |

TABLE 36

Exemplary Low Strength Tablet Formulation #3

| Ingredient | Source | Amount (weight %) |
|---|---|---|
| Solid form of Compound 1 | | 0.7 |
| microcrystalline cellulose | FMC Biopolymer | 38.1 |
| Lactose monohydrate | Meggle Pharma | 57.2 |
| sodium carboxymethylcellulose | FMC Biopolymer | 3.0 |
| magnesium stearate | Nitika Chemicals | 1.0 |

TABLE 37

Exemplary High Strength Tablet Formulation #1

| Ingredient | Source | Amount (weight %) |
|---|---|---|
| Solid form of Compound 1 | | 25.0 |
| microcrystalline cellulose | FMC Biopolymer | 28.4 |
| Mannitol | Roquette | 42.6 |
| sodium carboxymethylcellulose | FMC Biopolymer | 3.0 |
| magnesium stearate | Nitika Chemicals | 1.0 |

TABLE 38

Exemplary High Strength Tablet Formulation #2

| Ingredient | Source | Amount (weight %) |
|---|---|---|
| Solid form of Compound 1 | | 25.0 |
| microcrystalline cellulose | FMC Biopolymer | 51.0 |
| pregelatinized starch | Colorcon | 20.0 |
| sodium carboxymethylcellulose | FMC Biopolymer | 3.0 |
| magnesium stearate | Nitika Chemicals | 1.0 |

TABLE 39

Exemplary High Strength Tablet Formulation #3

| Ingredient | Source | Amount (weight %) |
|---|---|---|
| Solid form of Compound 1 | | 25.0 |
| microcrystalline cellulose | FMC Biopolymer | 28.4 |
| Lactose monohydrate | Meggle Pharma | 42.6 |
| sodium carboxymethylcellulose | FMC Biopolymer | 3.0 |
| magnesium stearate | Nitika Chemicals | 1.0 |

The above formulations are subjected to a 6 week stability study.

The embodiments disclosed herein are not to be limited in scope by the specific embodiments disclosed in the examples which are intended as illustrations of a few aspects of the disclosed embodiments and any embodiments that are functionally equivalent are encompassed by the present disclosure. Indeed, various modifications of the embodiments disclosed herein are in addition to those shown and described herein will become apparent to those skilled in the art and are intended to fall within the scope of the appended claims.

A number of references have been cited, the disclosures of which are incorporated herein by reference in their entirety.

What is claimed is:

1. An amorphous form of the compound of formula (I):

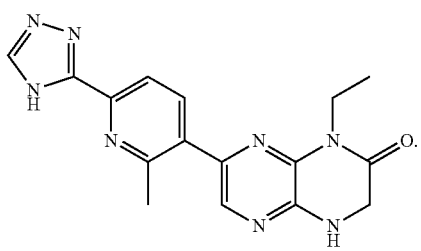

or a tautomer thereof,
wherein the amorphous form has an X-ray powder diffraction pattern as shown in FIG. 28.

2. The amorphous form of claim 1, which has a differential scanning calorimetry thermogram comprising an endotherm between 160° C.±5° C. and 200° C.±5° C. with a maximum at 188.1° C.±5° C.

3. The amorphous form of claim 1, which has a glass transition temperature at 120° C.±5° C.

4. The amorphous form of claim 1, which is pure.

5. A method for modulating target of rapamycin kinase activity in a subject, comprising administering to a subject in need thereof an effective amount of the amorphous form of claim 1.

6. The method of claim 5, wherein the subject suffers from a condition, disorder or disease selected from the group consisting of an inflammatory condition, an immunological condition, a cardiovascular condition, a neurological disorder, a neurodegenerative disease, an age-related disease, diabetes and obesity.

* * * * *